(12) United States Patent
Bailin

(10) Patent No.: US 8,965,496 B2
(45) Date of Patent: Feb. 24, 2015

(54) METHOD FOR DETERMINING THE LOCATION OF REGIONS IN TISSUE RELEVANT TO ELECTRICAL PROPAGATION

(75) Inventor: Steven J. Bailin, Urbandale, IA (US)

(73) Assignee: Steven J. Bailin, Urbandale, IA (US)

( * ) Notice: Subject to any disclaimer, the term of this patent is extended or adjusted under 35 U.S.C. 154(b) by 480 days.

(21) Appl. No.: 13/242,565

(22) Filed: Sep. 23, 2011

(65) Prior Publication Data

US 2012/0078129 A1  Mar. 29, 2012

Related U.S. Application Data

(60) Provisional application No. 61/386,843, filed on Sep. 27, 2010.

(51) Int. Cl.
*A61B 5/044* (2006.01)
*A61B 5/042* (2006.01)
*A61B 5/00* (2006.01)
*A61B 18/14* (2006.01)
*A61B 18/00* (2006.01)

(52) U.S. Cl.
CPC .............. *A61B 5/042* (2013.01); *A61B 5/7203* (2013.01); *A61B 18/1492* (2013.01); *A61B 2018/00357* (2013.01); *A61B 2018/00577* (2013.01)
USPC ........... 600/523; 600/410; 600/423; 600/443; 600/160

(58) Field of Classification Search
CPC .... A61B 5/0536; A61B 6/482; A61B 6/0566; A61B 2576/00; A61B 2017/00115

USPC .......... 600/410, 423, 443, 160, 523
See application file for complete search history.

(56) References Cited

U.S. PATENT DOCUMENTS

| 6,301,496 | B1 * | 10/2001 | Reisfeld ....................... 600/407 |
| 7,774,051 | B2 * | 8/2010 | Voth .............................. 600/523 |
| 2007/0197929 | A1 * | 8/2007 | Porath et al. .................. 600/523 |
| 2009/0192393 | A1 * | 7/2009 | Hayam et al. ................. 600/509 |

FOREIGN PATENT DOCUMENTS

EP  2064990 A1  6/2009

OTHER PUBLICATIONS

Huang , J.L. et al., "Substrate Mapping to Detect Abnormal Atrial Endocardium With Slow Conduction in Patients With Atypical Right Atrial Flutter", Journal of the American College of Cardiology, vol. 48, No. 3 (Aug. 1, 2006), pp. 492-498.

(Continued)

*Primary Examiner* — Catherine Voorhees
*Assistant Examiner* — Natasha Patel
(74) *Attorney, Agent, or Firm* — Knobbe, Martens, Olson & Bear, LLP.

(57) ABSTRACT

A method of displaying an image of the location of one or more low voltage structures in tissue is provided. The method includes receiving electrical mapping data corresponding to a portion of the tissue. The method further includes generating an image using the electrical mapping data. Electrical mapping values within at least one voltage range having two endpoints that bound the upper and lower limits of the voltage range are distinguishable from electrical mapping values outside the at least one voltage range. The two endpoints are selected to distinguish the one or more low voltage structures of the tissue from other portions of the tissue.

32 Claims, 45 Drawing Sheets

(56) References Cited

OTHER PUBLICATIONS

Bailin, Steven J. et al., "Direct visualization of the slow pathway using voltage gradient mapping: a novel approach for successful ablation of atrioventricular nodal reentry tachycardia", Europace, vol. 13, No. 8 (Apr. 19, 2011).

International Search Report dated Jan. 27, 2012, for International Application No. PCT/US2011/053113.

* cited by examiner

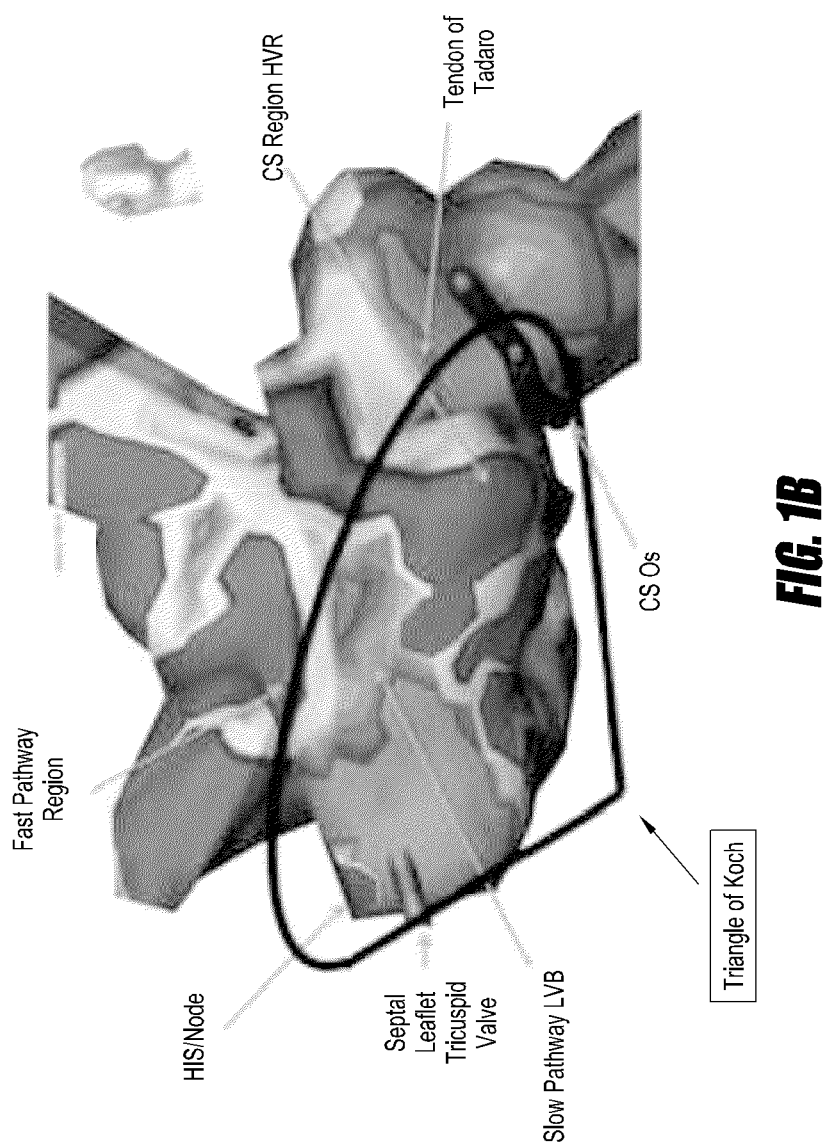

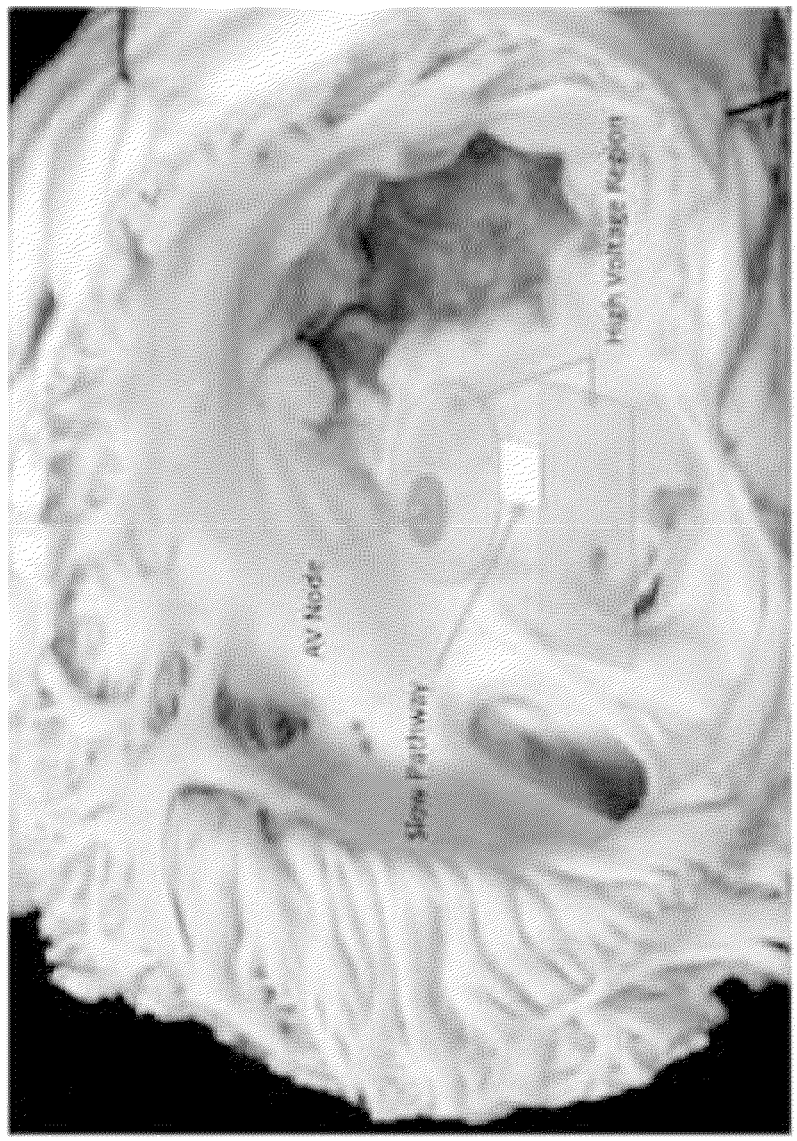

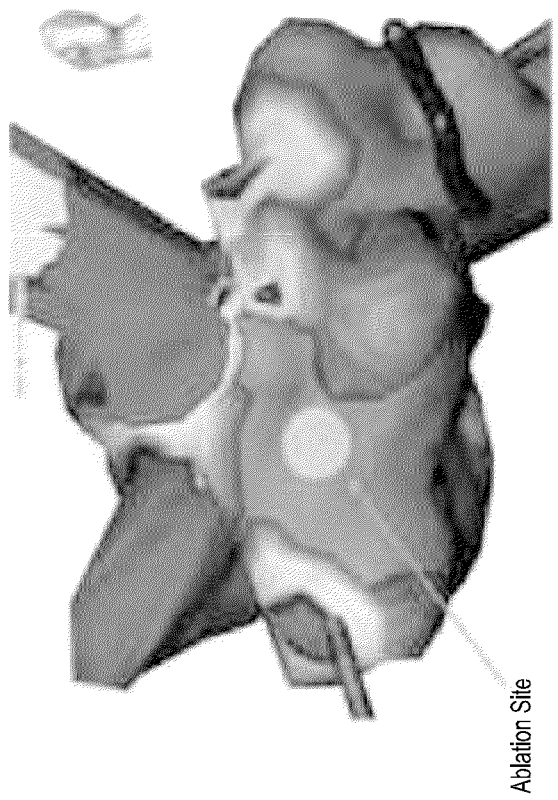

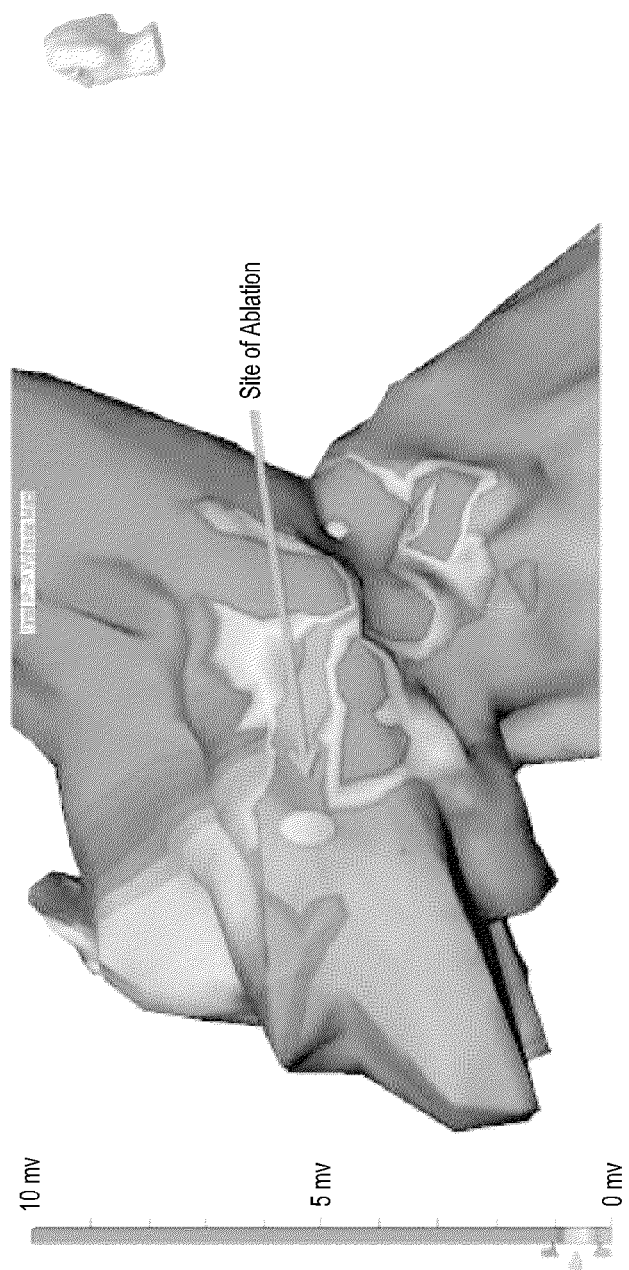

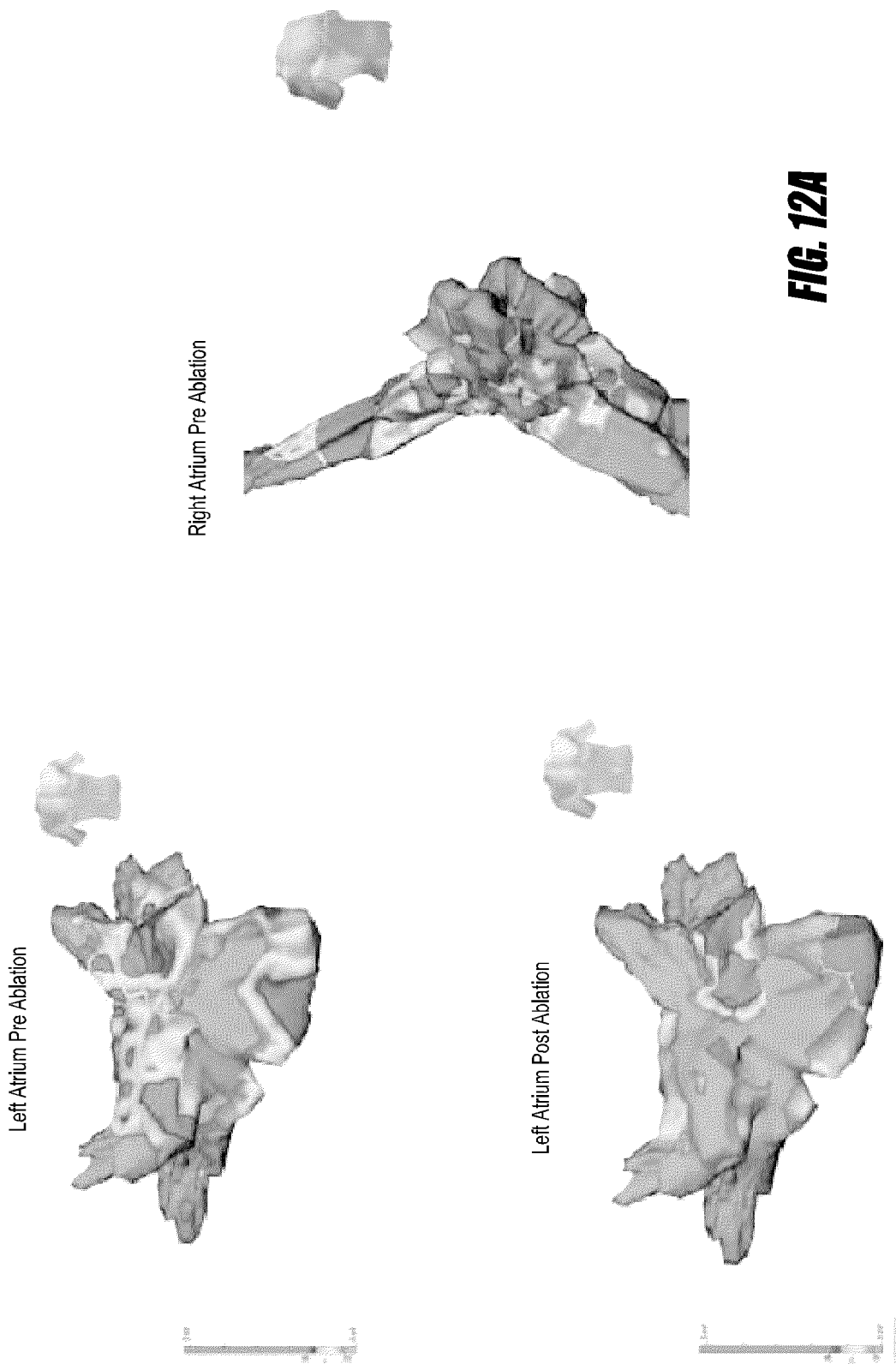

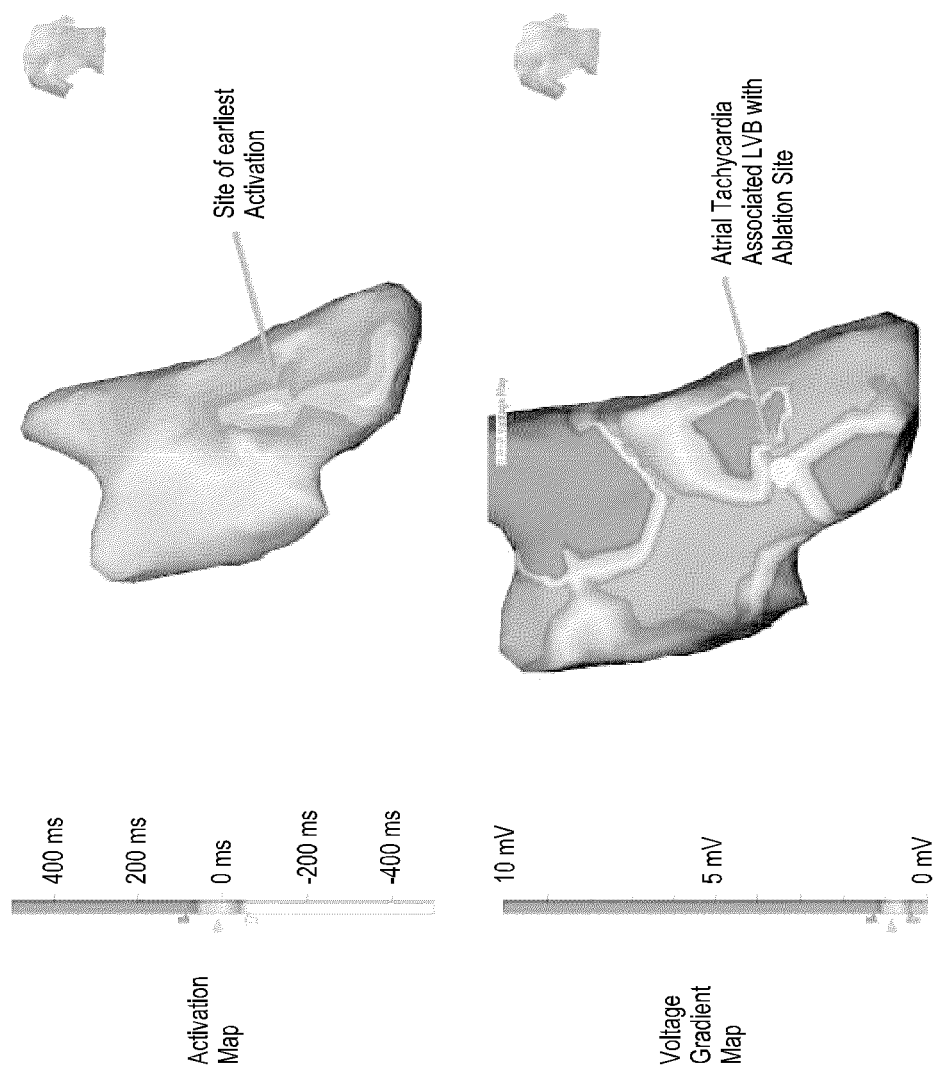

METHOD FOR DETERMINING THE LOCATION OF REGIONS IN TISSUE RELEVANT TO ELECTRICAL PROPAGATION

CLAIM OF PRIORITY

The present application claims the benefit of priority to U.S. Provisional Application No. 61/386,843, filed on Sep. 27, 2010 and incorporated in its entirety by reference herein.

BACKGROUND OF THE INVENTION

1. Field of the Invention

This invention relates generally to methods of diagnosis, evaluation, or treatment of tissue, and more particularly, to methods of utilizing voltage gradient mapping to determine the locations of relevant portions of cardiac tissue for ablative therapy.

2. Background

Atrioventricular nodal reentry tachycardia (AVNRT) is the most common supraventricular tachycardia inducible in the electrophysiology lab (See, e.g., Bastani et al., "Acute and long-term outcome of cryoablation therapy of typical atrioventricular nodal reentrant tachycardia," Europace, 2009 August (8):1077-82; Estner et al., "Acute and long-term results of slow pathway ablation in patients with atrioventricular nodal re-entrant tachycardia—an analysis of the predictive factors for arrhythmia recurrence," Pacing Clin. Electrophysiol, 28:102-10). Since the early 1990's, ablative therapy has proven to be the treatment of choice, beginning with radiofrequency application and more recently cryoablation (See, e.g., Bastani et al.; Fazekas et al., "Treatment of AV-nodal reentry tachycardia by transcatheter radiofrequency ablation," Orv Hetil, 1994 Aug. 20; 135 (34):1853-7). Although the procedure is highly successful with a relatively low complication rate, both complications and unsuccessful procedures remain. Successful ablations are seen in 91% to 99% of patients, with recurrence seen in 5-9% and heart block 1% (See, e.g., Bastani et al.; Zrenner et al., "Transvenous cryoablation versus radiofrequency ablation of the slow pathway for the treatment of atrioventricular nodal re-entrant tachycardia: a prospective randomized pilot study," Eur. Heart J. 2004, 25:2226-31; Silver et al., "Cryoablation of atrioventricular nodal reentrant tachycardia with an 8 mm-tip cryocatheter in pediatric patients: an early experience," Heart Rhythm Society, Scientific Sessions abstract (2008); Clague et al., "Targeting the slow pathway for atrioventricular nodal reentrant tachycardia: initial results and long-term follow-up in 379 consecutive patients," Eur. Heart J., 2001 January, 22 (1):82 (2001); Chan et al., "Treatment of atrioventricular nodal re-entrant tachycardia by cryoablation with a 6 mm-tip catheter vs. radiofrequency ablation," Europace, 2009 August, 11 (8):1065-70). There is a higher chance of recurrence in patients with single AV nodal echo versus patients with complete elimination of the slow pathway at the end of the procedure (See, e.g., Bastani et al.; Estner et al.; Manolis et al., "Radiofrequency ablation of slow pathway in patients with atrioventricular nodal reentrant tachycardia. Do arrhythmia recurrences correlate with persistent slow pathway conduction or site of successful ablation?", Circulation, 1994, 90:2815-19; Baker et al., "Predictors of recurrent atrioventricular nodal reentry after selective slow pathway ablation," Am. J. Cardiol. 1994, 73:765-9; Silva et al., "Relationship between conduction persistence through the slow pathway after atrioventricular nodal reentry tachycardia radiofrequency ablation and its recurrence," Arq. Bras. Cardiol. 1998, 71:117-20; Gupta et al., "Cryoablation compared with radiofrequency ablation for atrioventricular nodal re-entrant tachycardia: analysis of factors contributing to acute and follow-up outcome," Europace, 2006, 8:1022-6). Additionally, multiple AV nodal pathways are observed in approximately 39% of patients with AVNRT (See, e.g., Heinroth et al., "Multiple AV nodal pathways in patients with AV nodal reentrant tachycardia—more common than expected?", Europace, 2002 October, 4 (4):375-82; Tai et al., "Multiple anterograde atrioventricular node pathways in patients with atrioventricular node reentrant tachycardia," J. Am. Coll. Cardiol. 1996, 28:725-31).

Successful slow pathway ablation has previously been based primarily on anatomic and electrophysiological characteristics. The slow pathway has been described as being located along the inferior aspect of Koch's Triangle (see FIG. 1A), toward the tricuspid valve with an atrial voltage ratio $\frac{1}{10}$th to $\frac{1}{2}$ that of the ventricular voltage (See, e.g., Fazekas et al.; Haissaguerre et al., "Elimination of atrioventricular nodal reentrant tachycardia using discrete slow potentials to guide application of radiofrequency energy," Circulation, 1992, 85:164-74; Medkour et al., "Anatomic and Functional Characteristics of a Slow Posterior AV Nodal Pathway: Role in Dual-Pathway Physiology and reentry," Circulation 1998, 98:164-74; Kalbfleisch et al., "Randomized comparison of anatomic and electrogram mapping approaches to ablation of the slow pathway of atrioventricular node reentrant tachycardia," J. Am. Coll. Cardiol. 1994, 23:716-23; Manolis et al, "Arrhythmia recurrences are rare when the site of radiofrequency ablation of the slow pathway is medial or anterior to the coronary sinus os," Europace, 2002, 4:193-9; Wathen et al., "An anatomically guided approach to atrioventricular node slow pathway ablation," Am. J. Cardiol. 1992, 70 (9):886-9). Ablative therapy is applied in the region of the slow pathway until either a junctional response is produced (RF energy), or non-inducibility with, or without, AV Nodal echo beats results (cryoablation or RF energy) (See, e.g., Friedman H. L., "How to ablate atrioventricular nodal reentry using cryoenergy," Heart Rhythm, 2005, 2:893-6; Stabile et al., "The predictive value of junctional beats during the radiofrequency transcatheter ablation of the slow pathway of the nodal reentry circuit," G. Ital. Cardiol. 1999, 29:549-54; De Sisti et al., "Transvenous cryo-ablation of the slow pathway for the treatment of atrioventricular nodal reentrant tachycardia: a single-centre initial experience study," Europace, 2007, 9:401-6; Jentzer et al., "Analysis of junctional ectopy during radiofrequency ablation of the slow pathway in patients with atrioventricular nodal reentrant tachycardia," Circulation 1994, 90:2820-6; Iakobishvili et al., "Junctional rhythm quantity and duration during slow pathway radiofrequency ablation in patients with atrioventricular nodal re-entry supraventricular tachycardia," Europace 2006, 8:588-91). If the ablation lesion was unsuccessful, the catheter is repositioned, superiorly toward the AV Nodal region and the His catheter. Success is measured by the inability to induce AVNRT and/or a change in AV nodal properties (induction of a single echo beat) with an isuprel infusion (See, e.g., Weismüller et al., "Is electrical stimulation during administration of catecholamines required for the evaluation of success after ablation of atrioventricular node re-entrant tachycardias?", J. Am. Coll. Cardiol., 2002, 39:689-94. Unfortunately, in some patients, both anatomic and electrophysiologic criteria may not be sufficient. In such patients, ablations may become prolonged and may have a greater potential for failure or complication.

A number of approaches have been suggested for ablative treatment of atrial fibrillation. Either an anatomic based therapy, focused primarily upon isolation of the pulmonary veins, or targeted ablation of high frequency regions has been reported to have moderate success in paroxysmal and modest success in chronic atrial fibrillation. Because of the chaotic nature of the arrhythmia, conventional activation mapping has not proved helpful. Therefore the reasons for success or failure have remained obscure.

SUMMARY

In certain embodiments, a method of displaying an image of the location of one or more low voltage structures in tissue is provided. The method comprises receiving electrical mapping data corresponding to a portion of the tissue. The method further comprises generating an image using the electrical mapping data. Electrical mapping values within at least one voltage range comprising two endpoints that bound the upper and lower limits of the voltage range are distinguishable from electrical mapping values outside the at least one voltage range. The two endpoints are selected to distinguish the one or more low voltage structures of the tissue from other portions of the tissue.

In certain embodiments, a method for processing data for determining the location of one or more low voltage structures in tissue is provided. The method comprises receiving electrical mapping data corresponding to a portion of the tissue. The method further comprises analyzing the data by distinguishing electrical mapping values within at least one voltage range comprising two endpoints that bound the upper and lower limits of the voltage range from electrical mapping values outside the at least one voltage range. The two endpoints are selected to distinguish the one or more low voltage structures of the tissue from other portions of the tissue.

In certain embodiments, a method of treating tissue is provided. The method comprises receiving electrical mapping data corresponding to a portion of the tissue. The method further comprises analyzing the data by distinguishing electrical mapping values within at least one voltage range comprising two endpoints that bound the upper and lower limits of the voltage range from electrical mapping values outside the at least one voltage range. The two endpoints are selected to distinguish the one or more low voltage structures of the tissue from other portions of the tissue. The method further comprises locating at least a portion of the tissue corresponding to one or more of the low voltage structures.

In certain embodiments, a general-purpose computer is provided that comprises a computer-readable medium having instructions stored thereon which cause the general-purpose computer to receive electrical mapping data corresponding to a portion of the tissue. The instructions further cause the general-purpose computer to analyze the data by distinguishing electrical mapping values within at least one voltage range comprising two endpoints that bound the upper and lower limits of the voltage range from electrical mapping values outside the at least one voltage range. The two endpoints are selected to distinguish the one or more low voltage structures of the tissue from other portions of the tissue.

BRIEF DESCRIPTION OF THE FIGURES

FIG. 1B illustrates the triangle of Koch outlined over a 3-D Voltage Gradient Map. The region of interest containing the slow pathway associated low voltage bridge is contained within this outline.

FIG. 2A illustrates a Type I slow pathway associated low voltage bridges characterized by discrete isolated low voltage connections between the CS Os and the AV Nodal region.

FIG. 3B illustrates an ablation lesion placed within the slow pathway associated low voltage bridge which changes the voltage gradient map following ablation. No low voltage bridge is observed and the high voltage region of the CS Os no longer connects with the AV Nodal region. This finding correlates to a successful slow pathway ablation and inability to re-induce AVNRT or consistent AV Nodal echos.

FIGS. 9A and 9B illustrate Slow Pathway associated with AV Nodal Reentry Tachycardia (AVNRT), for pre-ablation and post-ablation, respectively. Multiple HVRs are observed but a single LVB is found in the region between the CS and the His bundle. Following ablation, no further connection is seen connecting the posterior septum to the His region.

FIG. 12A illustrates LVBs observed within the Left and Right Atrium. These LVBs connect HVRs within the atrium, pulmonary veins, and left atrial appendage. Post ablation of LA LVBs, the left atrial endocardium is significantly altered. A single LVB is seen at the mitral annulus and was subsequently ablated.

FIGS. 13A and 13B illustrate the Superior Vena Cava with LVB input, pre-ablation and post-ablation, respectively. Pre-ablation, the SVC is connected to the Right Atrium by multiple LVBs. Post-ablation of all connecting LVBs successfully isolates the SVC.

FIG. 16A illustrates LVB associated with automatic Left Atrial Tachycardia, with both an activation map and a VGM. The site of earliest activation correlates with the LVB. Ablation of the LVB terminated the tachycardia.

DETAILED DESCRIPTION

Figure 1A:
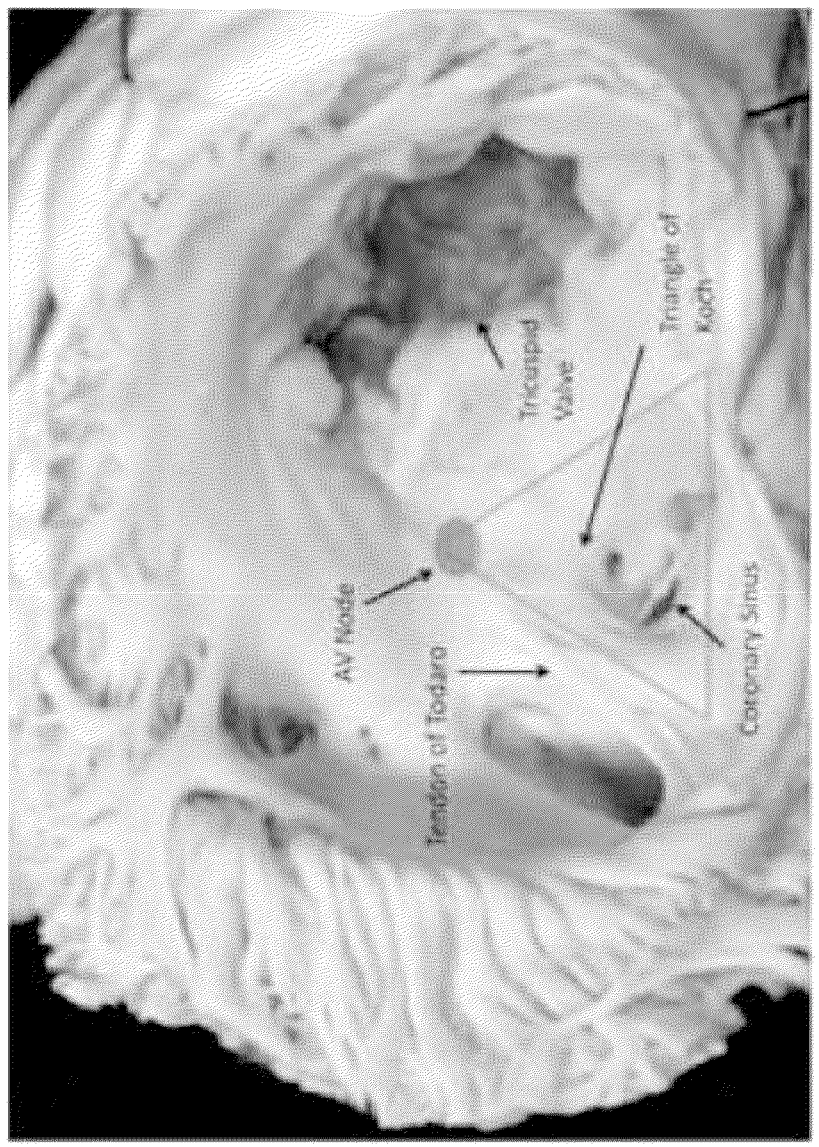
FIG. 1A illustrates the anatomy of the triangle of Koch formed by an area bounded by the Tendon of Todaro, the CS Os, and the septal leaflet of the Tricuspid Valve. The AV Node and bundle of His are located at the apex of Koch's triangle. (Image courtesy of Robert H. Anderson)

Modern mapping procedures have evolved to include information about regional activation and activation movement within cardiac chambers. These representations displayed in three dimensions offer insight into the mechanisms of cardiac arrhythmias. (See, e.g., Knackstedt et al., "Electroanatomic mapping systems in arrhythmias," Europace, 2008 November; 10 Suppl. 3:iii. pp. 28-34; Tai et al., "Noncontact mapping of the heart: how and when to use," J. Cardiovasc. Electrophysiol., 2009 January, 20 (1):123-6; Markides et al., "New mapping technologies: an overview with a clinical perspective," J. Interv. Card. Electrophysiol., 2005 August, 13 Suppl. 1:43-51.) However, determination of critical components of a circuit remains challenging during activation mapping. In reentry circuits, concealed entrainment pacing has been shown to reveal sites that are critical for tachycardia propagation, and can be used for identifying successful ablation sites. (See, e.g., Stevenson et al., "Identification of reentry circuit sites during catheter mapping and radiofrequency ablation of ventricular tachycardia late after myocardial infarction," Circulation, 1993 October, 88 (4 Pt 1):1647-70; Deo et al., "The clinical utility of entrainment pacing," Cardiovasc. Electrophysiol., 2009 April, 20 (4):466-70.) Identification of abnormal substrate by creation of a voltage map reveals regions of non-viable tissue, as well as viable isthmuses that can be helpful to create lines of block for ventricular tachycardia ablation. (See, e.g., Reddy et al., "Short-term results of substrate mapping and radiofrequency ablation of ischemic ventricular tachycardia using a saline-irrigated catheter," J. Am. Coll. Cardiol., 2003 Jun. 18; 41 (12):2228-36; Bogun et al., "Analysis during sinus rhythm of critical sites in reentry circuits of postinfarction ventricular tachycardia," J. Interv. Card. Electrophysiol., 2002 August, 7 (1):95-103.) However, a method that could provide direct visualization of critical connections for the propagation and maintenance of arrhythmias would greatly simplify the analysis and improve the success of ablation therapy.

Identification of the slow pathway in accordance with certain embodiments described herein can directly expedite ablation success and enhance safety. For example, voltage gradient mapping (VGM) can be performed to construct three-dimensional voltage maps of the atrium from intracardiac recordings obtained by contact mapping. As described above, these voltage maps can be constructed using voltage values that are adjusted so as to directly image or visualize the low voltage bridging (e.g., regions of low voltage that connect regions of high voltage together) indicative of the slow pathway within the Triangle of Koch and to aid successful ablation of atrioventricular nodal reentry tachycardia. In certain embodiments described herein, voltage gradient mapping can directly visualize the slow pathway and its anatomical position, and subsequent ablation of the associated low voltage bridge can result in loss of slow pathway function and significant changes in the post-ablation voltage map. Thus, in certain embodiments, voltage gradient mapping can provide the capability to precisely target the slow pathway for successful ablation, even in patients with multiple slow pathways or challenging anatomy.

In certain embodiments, a method for determining the location of one or more low voltage structures in tissue is provided. The method comprises performing electrical mapping to create a reconstruction of a portion of the tissue, wherein the electrical mapping is performed using at least one voltage range comprising two endpoints that bound the upper and lower limits of the voltage range, wherein the two endpoints are selected to distinguish the one or more low voltage structures of the tissue from other portions of the tissue to determine the location of the one or more low voltage structures.

In certain embodiments, the electrical mapping comprises voltage gradient mapping, and the voltage gradient mapping is performed by contact voltage mapping. In certain embodiments, the reconstruction is an image (e.g., a three-dimensional image).

In certain embodiments, the method further comprises determining at least one endpoint of the two endpoints dynamically based on voltages of the tissue being mapped. Determining the at least one endpoint can comprise determining one or more of the following: an average voltage of the tissue being mapped, a maximum voltage of the tissue being mapped, and a minimum voltage of the tissue being mapped. Determining the at least one endpoint can comprise determining both endpoints of the two endpoints dynamically based on voltages of the tissue being mapped.

In certain embodiments, the tissue comprises cardiac tissue, and the one or more low voltage structures comprise one or more low voltage bridges that are indicative of a region for electrical propagation (e.g., a slow pathway) in the cardiac tissue. The portion of the cardiac tissue can comprise the atrial endocardial portion of the cardiac tissue. All portions of the heart may be subject to the method described herein, including but not limited to, the right atrium, right ventricle, left atrium, left ventricle, coronary sinus, pulmonary veins, inferior vena cava, superior vena cava, and other veinous structures, using either endocardial mapping or epicardial mapping. In certain embodiments, the one or more low voltage bridges are within the atrial septum of the cardiac tissue. In certain embodiments, the two endpoints are equal to or between 0.1 mV and 0.6 mV, equal to or between 0.6 mV and 1.2 mV, or equal to or between 1 mV and 5 mV.

In certain embodiments, a method of treating tissue comprises performing the method for determining the location of one or more low voltage structures in tissue, and locating at least a portion of the tissue corresponding to one or more of the low voltage structures. In certain embodiments, the tissue is cardiac tissue and the located portion of tissue comprises one or more low voltage structures comprising a slow pathway. In certain embodiments, the method further comprises ablating at least a portion of the slow pathway.

In certain embodiments, the tissue comprises neurological tissue and the located portion of the tissue comprises seizure and/or trauma foci. In certain other embodiments, the tissue comprises skeletal muscle tissue or smooth muscle tissue (e.g., peristaltic tissue), or retinal tissue.

Certain embodiments described herein are techniques for determining the location of a region for electrical propagation (for example, the slow pathway) in tissue (e.g., cardiac tissue) for diagnosis, evaluation, or treatment of various maladies and/or conditions, including but not limited to, cardiac arrhythmia, including supraventricular tachycardia such as atrioventricular nodal reentry tachycardia (AVNRT), reciprocating tachycardia, atrial flutter, atrial or ventricular tachycardia, and atrial or ventricular fibrillation. Ablative therapy is currently the treatment of choice for AVNRT, using various techniques (e.g., RF or cryoablation) to ablate tissue in the region of the slow pathway. Certain embodiments described herein provide a new method of directly visualizing the location of the relevant region for electrical propagation (e.g., the slow pathway) to better identify where the ablation should be performed.

Certain embodiments described herein comprise one or more general-purpose computers programmed, running software, or otherwise configured to perform the analyses and methods described herein. Such computers can include a computer-readable medium having instructions stored thereon which cause the general-purpose computer to perform one or more of the methods described herein. Such computers can take a wide variety of forms, including network servers, workstations, personal computers, mainframe computers and the like. The code which configures the computer to perform such analyses is typically provided to the user on a computer-readable medium, such as a CD-ROM, DVD, a flash memory drive, or other tangible, non-transitory storage medium. The code that programs the computer may also be downloaded by a user from a network server which is part of a local-area network (LAN) or a wide-area network (WAN), such as the Internet.

The general-purpose computer will typically include one or more input devices, such as a mouse, trackball, touchpad, and/or keyboard, a display, and computer-readable memory media, such as random-access memory (RAM) integrated circuits and a hard-disk drive. It will be appreciated that one or more portions, or all of the code may be remote from the user and, for example, resident on a network resource, such as a LAN server, Internet server, network storage device, etc. In typical embodiments, the computer receives as an input a variety of information concerning the tissue being mapped.

Certain embodiments described herein comprise systems dedicated to performing electrical mapping (e.g., voltage gradient mapping), an example of which includes, but is not limited to, the Ensite Navx™ system of St. Jude Medical. In certain such embodiments, the system is configured to create a three-dimensional reconstruction of the atrial endocardial geometry by contact voltage mapping. Such systems can include circuitry or one or more computers programmed, running software, or otherwise configured to perform the analyses and methods described herein in addition to, or in replacement of, conventional electrical mapping procedures.

The voltage gradient mapping of certain such embodiments is performed by utilizing measured peak-to-peak voltages. Regional peak-to-peak voltages are then compared and small changes in absolute voltage are reflected by color gradients. Existing voltage gradient mapping techniques generally utilize a single set point or voltage to distinguish between viable tissue (having a voltage above the set point) and non-viable tissue (having a voltage below the set point). In contrast, certain embodiments described herein utilize a low voltage range or window having a low set point and a high set point. By examining the tissue having voltages within this low voltage window, the low voltage bridges within the atrial septum in certain embodiments can be directly imaged and these images can be used to locate the region for electrical propagation (e.g., the slow pathway) to be ablated. In certain other embodiments, the region for electrical propagation to be ablated is another region of the cardiac tissue besides the slow pathway.

In certain embodiments, the low set point and the high set point are not selected to distinguish between viable tissue and non-viable tissue. Instead, in certain such embodiments, the low set point and the high set point are selected to distinguish tissue that is relevant to electrical conduction from tissue that is not relevant to electrical conduction. For example, normal tissue would be expected to have relatively high voltage compared to scar or regions of abnormal conduction. These lower voltage regions reflect critical connections for tissue conductance and are generally found connecting regions of higher voltage. As such, low voltage regions are referred to as low voltage bridges.

Various example embodiments utilize voltage windows having voltages in the ranges of 0.1 mV to 0.6 mV, 0.6 mV to 1.2 mV, and 1 mV to 5 mV, and higher. In certain embodiments, the low and high set points can be determined dynamically based on the voltages of the tissue in the region being imaged. For example, at least one of the low and high set points can be determined in response to one or more of the following voltages: the average voltage of the region of tissue, the maximum voltage of the region of tissue, or the minimum voltage of the region of tissue. The voltage adjustments are varied until the underlying tissue substrate is discerned, e.g., identification of low voltage connections within the tissue.

In certain embodiments, the data collection can be automated, in whole or at least in part, using morphology matching. For example, using a surface EKG or other electrode, the operator selects the beat he wishes to study. As such, premature beats, unwanted tachycardia rhythms or measurements from the wrong chamber (atrial or ventricular) may be automatically excluded. During data acquisition, the computer collects data only when the morphology template matches, avoiding data collection when the template does not match. In certain embodiments, this process can exclude premature beats or unwanted tachycardia from being collected.

In certain embodiments, the voltage settings can be automated, in whole or at least in part. For example, the computer can automatically calculate the mean voltage collected and number of electograms recorded per square inch. The voltage display can then be adjusted such that the low voltage is a predetermined percentage of the high voltage (e.g., 20% of the high voltage setting). The high voltage can be selected to represent a percentage of the recorded voltage, (e.g., 80% of the recorded voltage). The percentage of voltage utilized with the high or low voltage setting would be defined to isolate the critical low voltage connection. The actual percentage may therefore vary in accordance to the recorded voltage obtained.

In certain embodiments, the low voltage bridge targeting can be automated, in whole or at least in part. For example, the low voltage bridges can be analyzed to evaluate for electrogram morphology. Electrograms within the low voltage bridge that demonstrate complex features such as multiple peaks, fractionated potentials, high frequency or prolonged activation can be selectively displayed.

In certain embodiments, the non-contact mapping from regional voltage change can be converted to point-to-point absolute voltage recording. In certain such embodiments, such a conversion can provide a real-time voltage gradient map display. For example, the array, Endocardial Solutions, St. Jude Medical, would permit such a modification.

While certain embodiments described above have been used with regard to cardiac tissue and arrhythmia, certain other embodiments can be used with other types of tissue and/or physiologic processes. For example, in certain various embodiments, these other types of tissue can include neurological tissue (e.g., neuro-mapping to locate seizure and/or trauma foci), muscle tissue (e.g., muscle mapping of skeletal and/or smooth muscle, such as the peristaltic tissue of the gastrointestinal tract, for identification of focal tissue abnormalities, thereby permitting treatment via biopsy or therapy), and retinal tissue (e.g., retinal mapping). The principals of voltage gradient mapping would be applied in other electrically active tissue. The definition of critical connections would be determined by adjustment of high and low voltage such that low voltage bridges can be identified.

Example Study 1

In an example study, twelve (12) consecutive patients with AVNRT, and five (5) control patients with accessory pathway mediated tachycardia without AVNRT or dual AV nodal physiology were evaluated by voltage gradient mapping. The slow pathway was indentified in all 17 patients via its corresponding low voltage bridge. Low voltage bridges were not observed in patients without dual AV nodal physiology.

Voltage gradient maps were created using the Ensite Navx™ (SJM) system. The creation of voltage maps has been previously validated. (See, e.g., Cassella et al., "Right ventricular substrate mapping using the Ensite Navx system: Accuracy of high-density voltage map obtained by automatic point acquisition during geometry reconstruction," Heart Rhythm, 2009 November, 6 (11):1598-605, Epub 2009 Jul. 22; Patel et al., "Atrial tachycardia after ablation of persistent atrial fibrillation: identification of the critical isthmus with a combination of multielectrode activation mapping and targeted entrainment mapping," Circ. Arrhyth. Electrophysiol. 2008 April, 1 (1):14-22.) A three-dimensional (3D) reconstruction of the atrial endocardial geometry was created by contact voltage mapping using either a 20-pole electrode catheter (St. Jude Medical Reflexion HD) or a quadrupolar ablation catheter. Peak to peak voltage data was collected during sinus rhythm using a Dx Landmark Map (St. Jude Medical) of the right atrium, paying particular attention to collection of data from the atrial septum within the triangle of Koch. Interpolation was set to 10 mm and the interior/exterior projection set to 7 mm. The voltage high slider was adjusted to 1.5 mV, and the color low slider was adjusted dynamically to reveal low voltage bridges within the atrial septum. On the display, voltage data below the voltage low value was shown as grey, voltage data between the color low and the color high values were displayed as red and yellow, while voltage data above the color high value was displayed as purple. Data points were reviewed within each low voltage bridges to confirm the validity of the recorded data to exclude premature atrial, junctional, or ventricular beats.

Ablation site was selected by low voltage bridge position only, and not based upon anatomic position or AV ratio. After confirmation of the data, ablation of the slow pathway associated low voltage bridges was performed using either Cryo-Max (MDT) or Safire (St. Jude Medical) ablation catheters. Following ablation, a repeat voltage gradient map was performed. The study endpoint was the loss of antegrade slow pathway function and the absence of consistent AV nodal echo beats. Ablation of the slow pathway associated low voltage bridges in 12 patients with tachycardia was successful. The repeat mapping confirmed the absence of low voltage connections previously observed.

The mean patient age was 38 years old, with a range of 12-66 years old. 67% of the patients were female and 33% were male. Acute success was achieved in all patients (12/12). Successful ablation was defined as the absence of antegrade slow pathway function, inability to re-induce AVNRT (with and without isuprel), and absence of consistent AV Nodal echo beats. No complications were observed during this study. No recurrences of AVNRT were noted during a follow-up period of 4 months following ablation.

The mean voltage low setting for visualizing the slow pathway associated low voltage bridge in the study was 0.173 mV (and ranged from 0.06 mV to 0.293 mV). The high voltage was set at a mean of 1.5 mV. The mean surface area data point density was 3.7 data points per $cm^2$ (range 2.0 to 6.7 data points per $cm^2$).

Figure 1C:
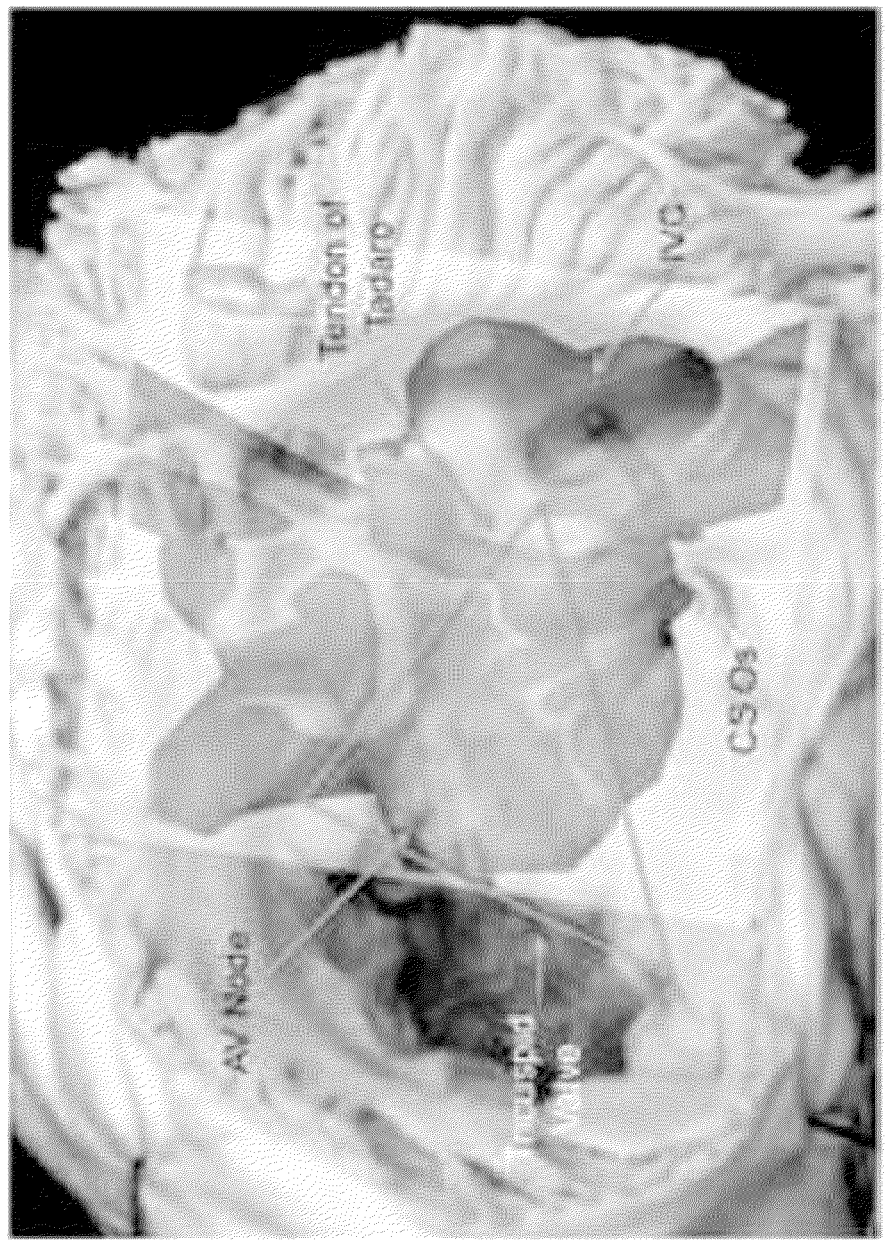
FIG. 1C illustrates the 3-D map of FIG. 1B projected over the anatomic preparation. The AV Nodal region is projected over the apex of Koch's Triangle.

The anatomic structure of the triangle of Koch is displayed in FIG. 1A (adopted from Anderson et al., "Anatomic criteria for identifying the components of the axis responsible for atrioventricular conduction," J. Cardiovasc. Electrophysiol. 2001, 12:1265-1268). To better understand the anatomic relationships associated with the 3D endocardial reconstruction created by voltage gradient mapping, FIG. 1B shows the position of Koch's Triangle outlined on the created voltage map. FIG. 1C superimposes the 3D endocardial voltage gradient map upon the anatomic structures of the right atrial septum.

Figure 2B:
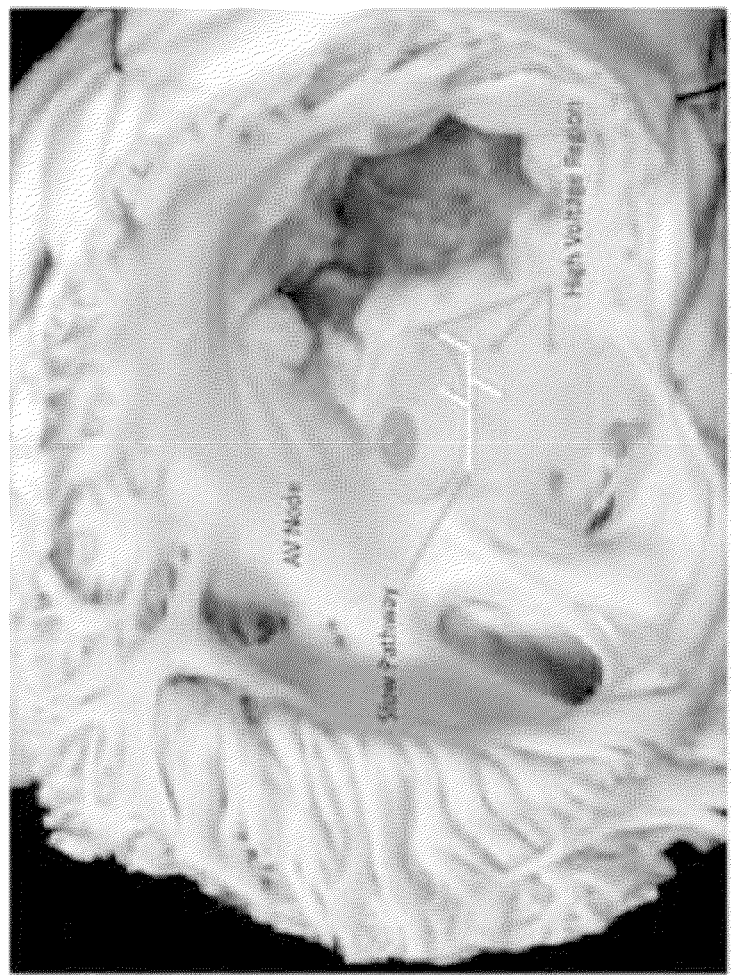
FIG. 2B illustrates a Type II slow pathway associated low voltage bridges characterized by narrow bands of low voltage connecting high voltage regions between the CS Os and the AV Node. This type of connection is less common, and utilizes an understanding of the anatomy of Koch's triangle. The high voltage regions should span from the CS Os to the AV Node.

Several morphologies of slow pathway associated low voltage bridges were observed. The majority of patients (10 of 12 or 83%) had a discrete low voltage bridge that connected the high voltage region of the coronary sinus ostium (CS Os) to the high voltage region of the AV Node/His, which was designated as Type I low voltage bridge connections (see FIG. 2A). In 2 patients (17%), the slow pathway associated low voltage bridge was a narrow region between adjacent high voltage gradient regions, but were always found within the triangle of Koch and was designated as Type II low voltage bridge connections (see FIG. 2B).

Figure 3A:
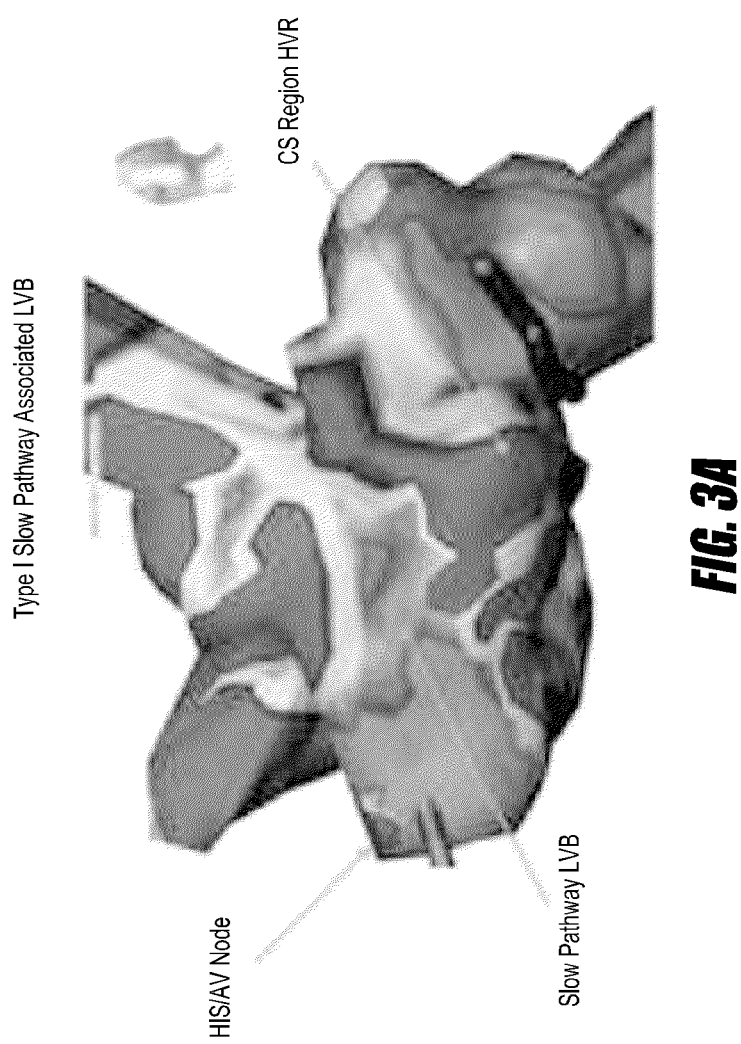
FIG. 3A illustrates a discrete Type I low voltage bridge connection seen in the voltage gradient map recorded at baseline. Here the low voltage bridge is seen spanning the atrial septum from the CS Os to the AV Node.
Figure 3C:
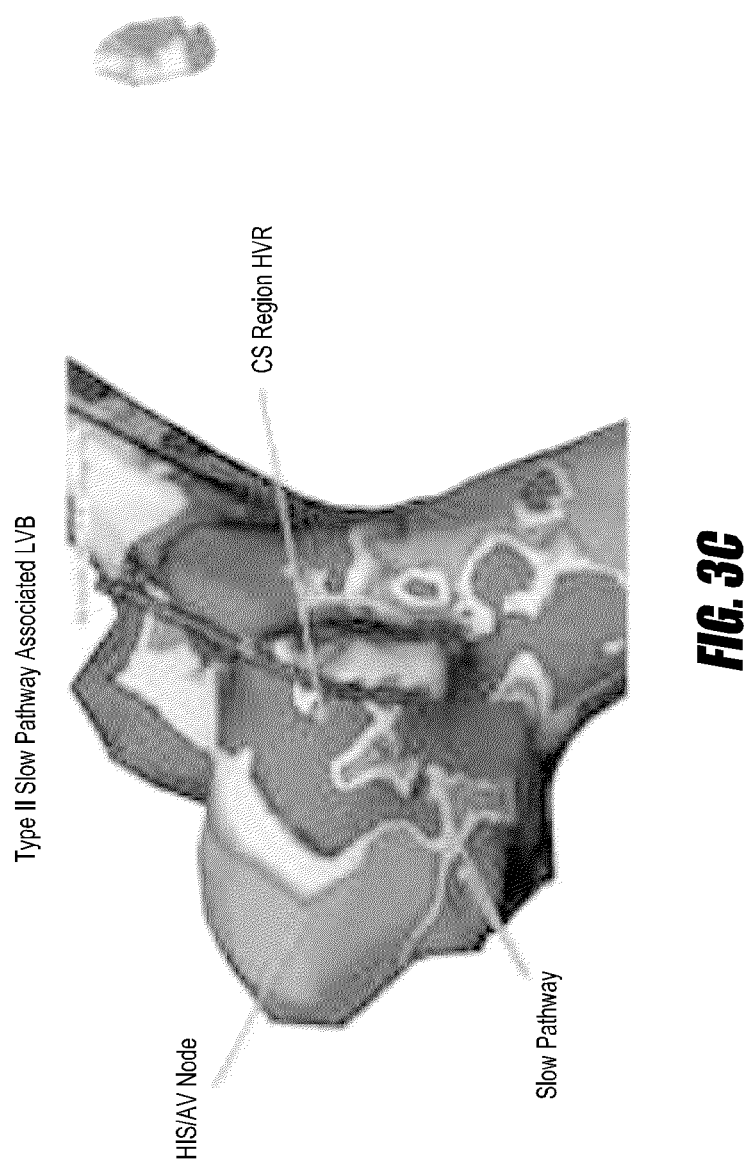
FIG. 3C illustrates a Type II low voltage bridge narrowly connecting two high voltage regions with a small high voltage isthmus. Successful ablation utilizes lesions below and above the high voltage isthmus.
Figure 3D:
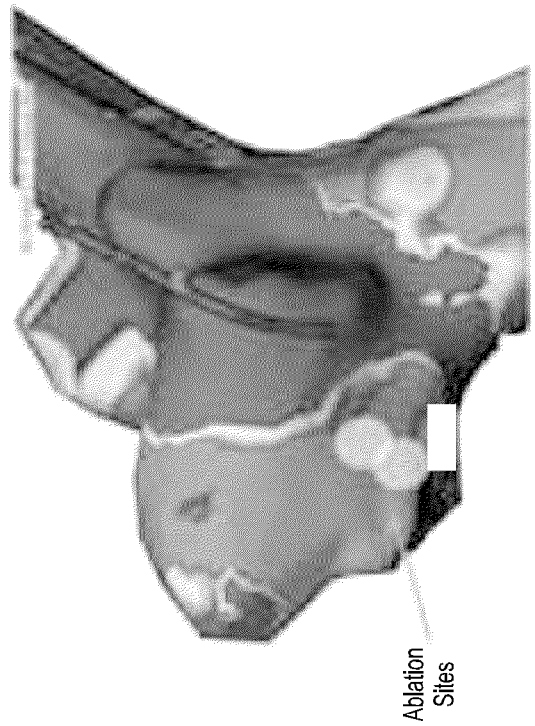
FIG. 3D illustrates that following ablation, no further connection is seen linking the CS Os to the AV Node. No further tachycardia was inducible.
Figure 5A:
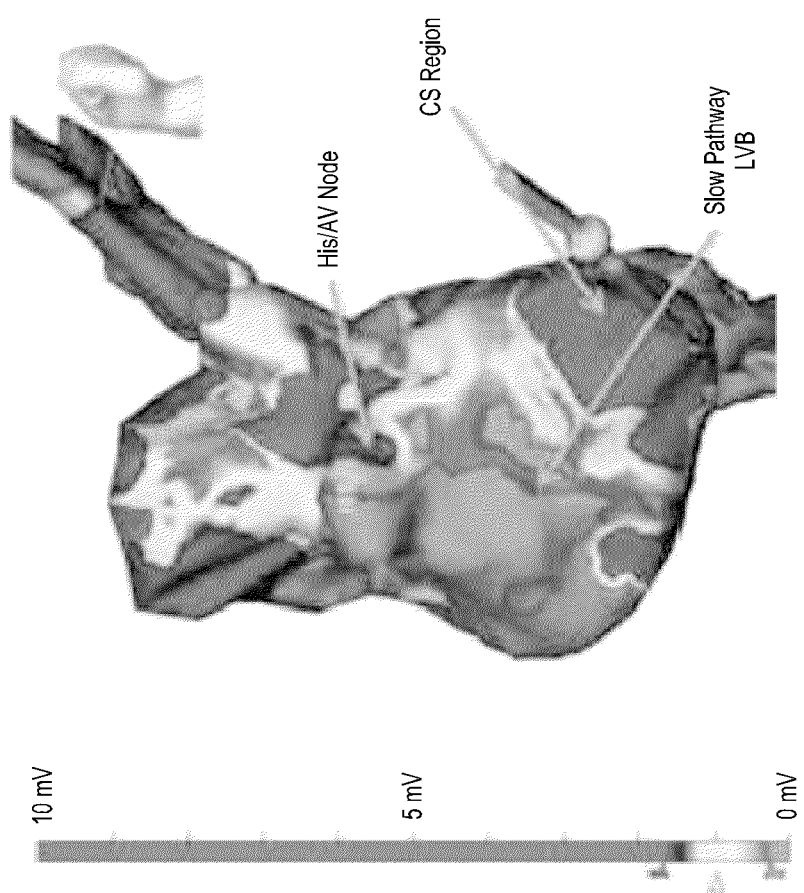
FIG. 5A illustrates a type I slow pathway associated low voltage bridge observed during the initial voltage gradient map.

A clinical example of a type I slow pathway associated low voltage bridge study is displayed in FIG. 5A. Voltage gradient mapping demonstrated a clear visualization of the slow pathway associated low voltage bridge before ablation (FIG. 3A). Following ablation, significant changes within Koch's triangle were observed (FIG. 3B). The absence of the low voltage bridge correlated with successful slow pathway ablation. In FIG. 3C, the slow pathway associated low voltage bridge is seen as a narrow band separating regions of high voltage, and is an example of a type II low voltage bridge connection. Following ablation, the voltage gradient map changed and no viable connection was observed between the CS Os region and the AV Nodal region (FIG. 3D). This finding correlated with successful ablation of the slow pathway.

Figure 4A:
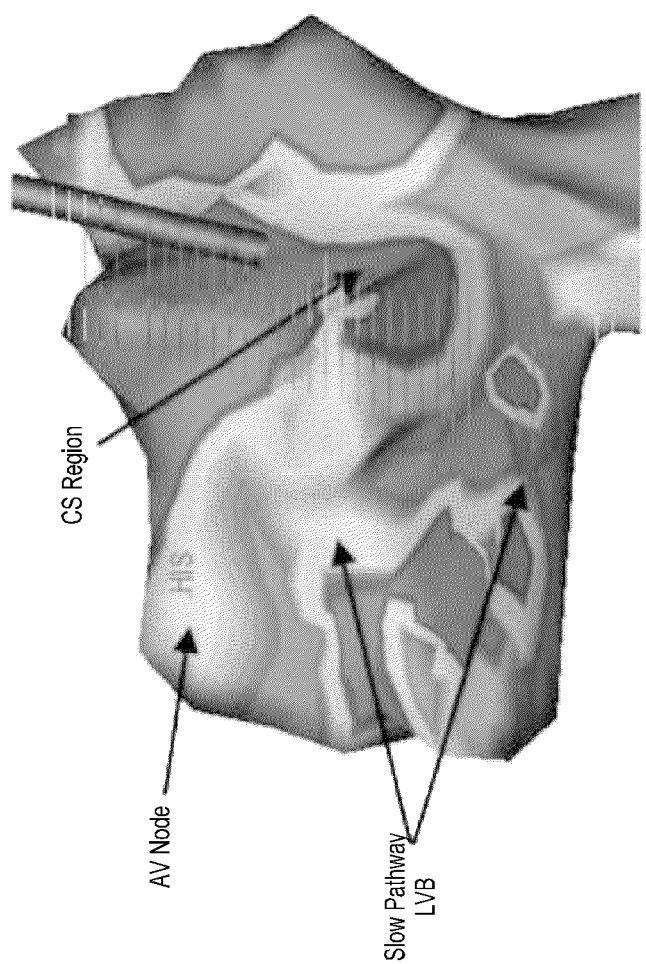
FIG. 4A illustrates a complex voltage gradient map observed in this patient. Several slow pathway associated low voltage bridges are found. Variable AH intervals were found at baseline and successful ablation utilized lesions at both low voltage bridges.
Figure 4B:
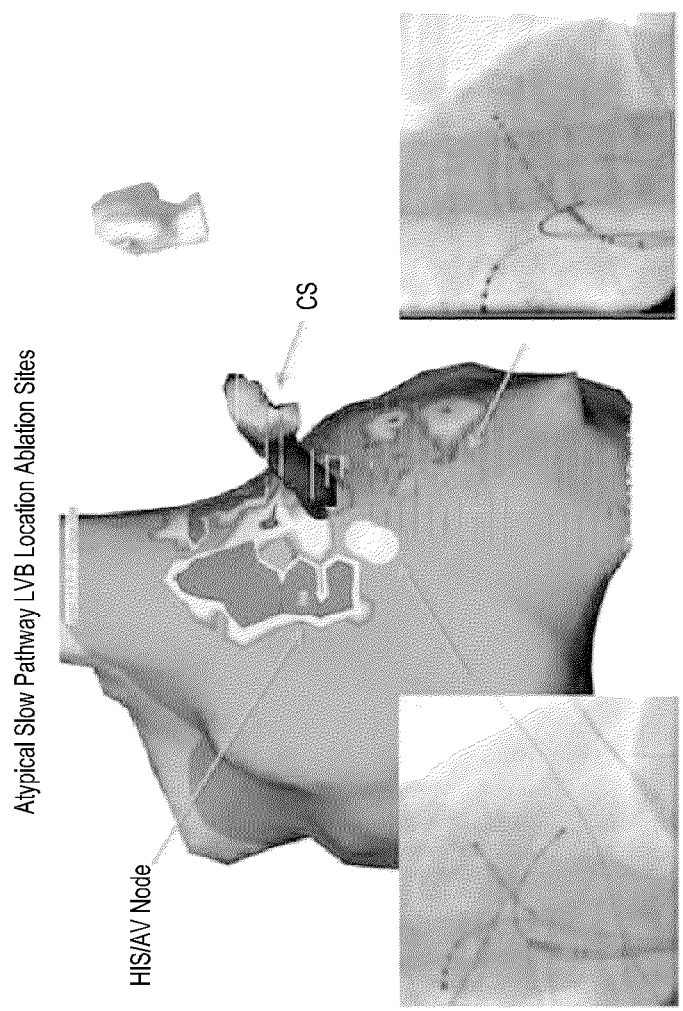
FIG. 4B illustrates voltage gradient mapping that directs placement of cryo lesions in a patient with multiple slow pathways. One slow pathway associated low voltage bridge is found proximal to the AV Node in an unusual anatomic location. Ablations at both sites were used for success, and no further AVNRT was inducible. Corresponding fluoroscopy images are provided.

In some patients, the slow pathway was located in unusual positions. In FIG. 4A, multiple slow pathways were observed within the triangle of Koch. As noted, in this patient, a second slow pathway associated low voltage bridge was located just inferior and proximal to the AV Node. Ablation in this region had an electrogram with A>V, and given proximity to the AV Node, may have presented a challenge for successful ablation without voltage gradient map guidance (FIG. 4B).

In this example study, single slow pathways were found in all Type I low voltage bridge. In these patients, the first lesion was successful in terminating or preventing re-induction of tachycardia. The time to this effect was less than 27 seconds. By contrast, Type II low voltage bridge was associated with multiple slow pathways and prevention of tachycardia required an average of 8.5 lesions. In all patients, the Wenckebach cycle length increased by an average of 96 ms.

A conclusion that low voltage bridges located within the triangle of Koch are indicative of the slow pathway is supported by the following observations from this example study:

1. The Presence of Low Voltage Bridges Correlated with Electrophysiologic Evidence of Slow Pathway Function.

Slow pathway associated low voltage bridge was identified in all patients with inducible AVNRT. Patients with dual AV Nodal physiology without inducible AVNRT also demonstrated the presence of a slow pathway low voltage bridge. The characteristics of the low voltage bridge cannot be used to distinguish clinically relevant slow pathways, e.g., those associated with clinical AVNRT, from those which are incidental findings.

2. The Absence of Posterior Septum Low Voltage Bridge Correlated with the Absence of Slow Pathway Function.

Patients without inducible AVNRT or dual AV Nodal physiology do not have low voltage bridge within the triangle of Koch. See FIG. 3E.

3. In Patients with Dual AV Nodal Physiology, Slow Pathway Refractoriness Correlated with the Disappearance of the Slow Pathway Low Voltage Bridge.

Figure 5B:
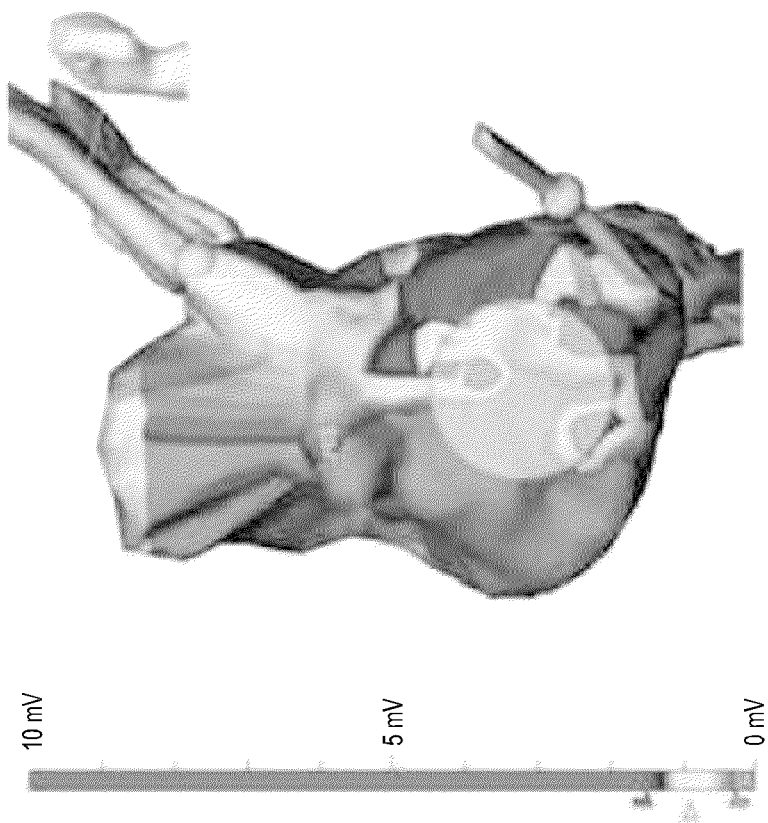
FIG. 5B illustrates that during programmed stimulation, progressive S2 premature stimulation results in refractory slow pathway conduction. As noted in this figure, the slow pathway low voltage bridge is now absent.
Figure 5C:
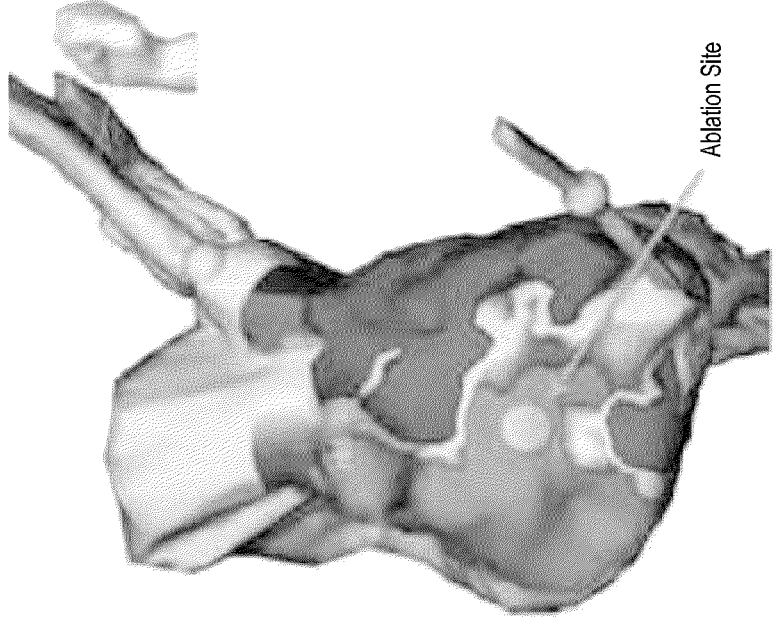
FIG. 5C illustrates that following ablation, the slow pathway low voltage bridge is gone and no further voltage connection is seen connecting the CS Os to the AV Node.
Figure 5C:
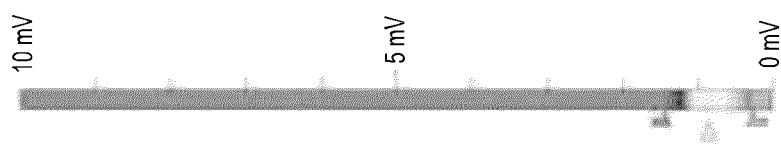

During atrial premature stimulation, mapping within Koch's triangle demonstrated a loss of the slow pathway associated low voltage bridge when the slow pathway refractory period is reached (FIG. 5A, 5B, 5C)

4. Ablation of the Slow Pathway Low Voltage Bridge Resulted in Termination of AVNRT and Inability to Reinduce AVNRT.

The lack of inducibility correlated with absence of slow pathway low voltage bridge following successful ablation. The high voltage regions of the CS Os and the AV Node are electrically altered and demonstrate an absence of low voltage bridge connection following ablation.

5. A Consistent Isolated AV Nodal Echo was Associated with an Incomplete Low Voltage Bridge Ablation.

Figure 6A:
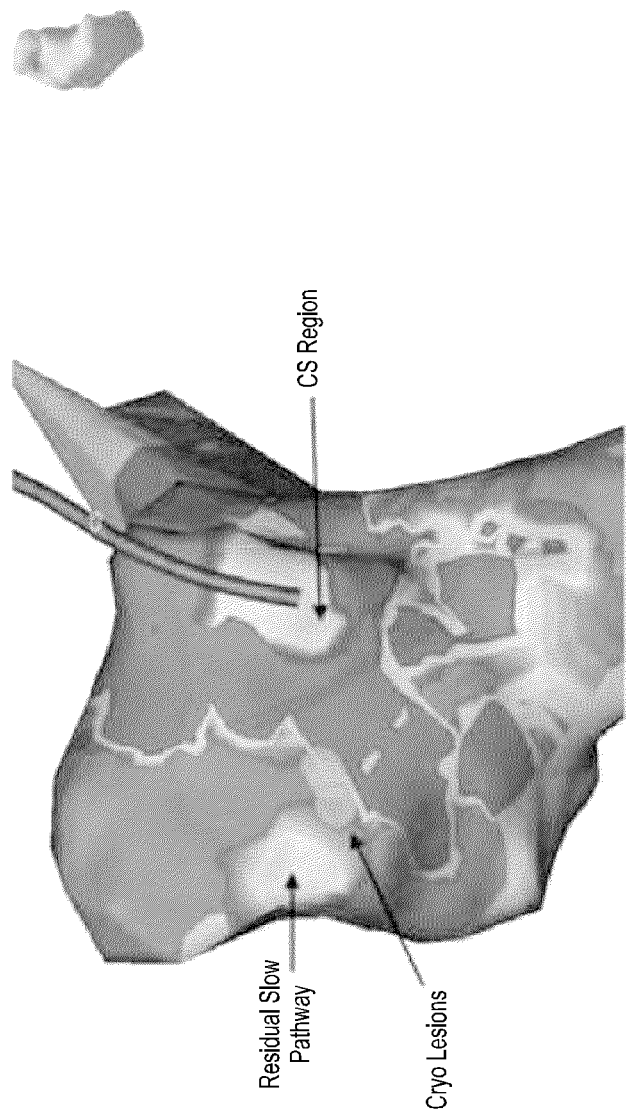
FIGS. 6A and 6B illustrate that after initial ablation, residual slow pathway function was observed. Consistent single AV Nodal echos were found during programmed stimulation. Remapping found a residual slow pathway. Further ablation at that site prevented further nodal echos.
Figure 6B:
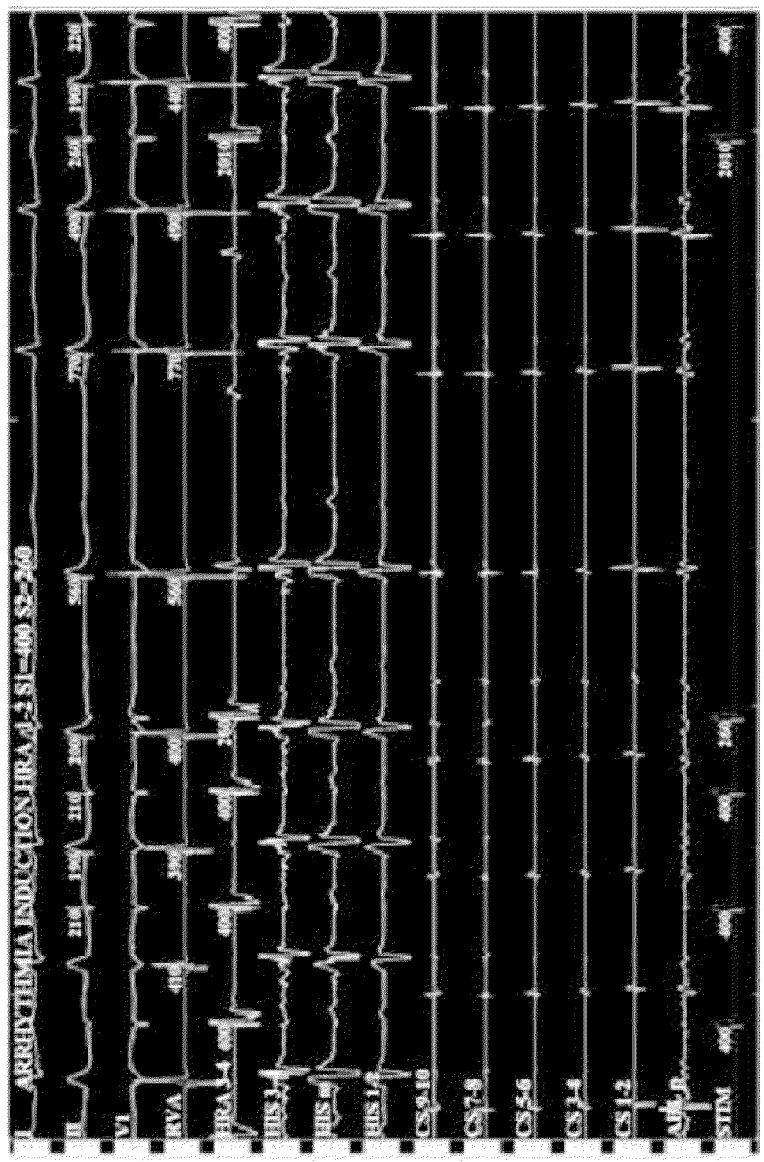

In such cases, a residual low voltage bridge connection persisted (FIG. 6A, 6B). Following further voltage gradient map directed ablation, successful ablation demonstrated the absence of both the slow pathway associated low voltage bridge and consistent AV Nodal echos. The presence of consistent single AV Nodal echo following ablation may also represent the presence of a second, separate, and distinct slow pathway low voltage bridge, which requires further voltage gradient map guided ablation.

6. Slow Pathway Low Voltage Bridge Electrograms Often Agreed with Conventional Electrophysiologic Criteria and May Demonstrate Complex Atrial Signals that have been Previously Associated with Slow Pathway Potentials.

Figure 7:
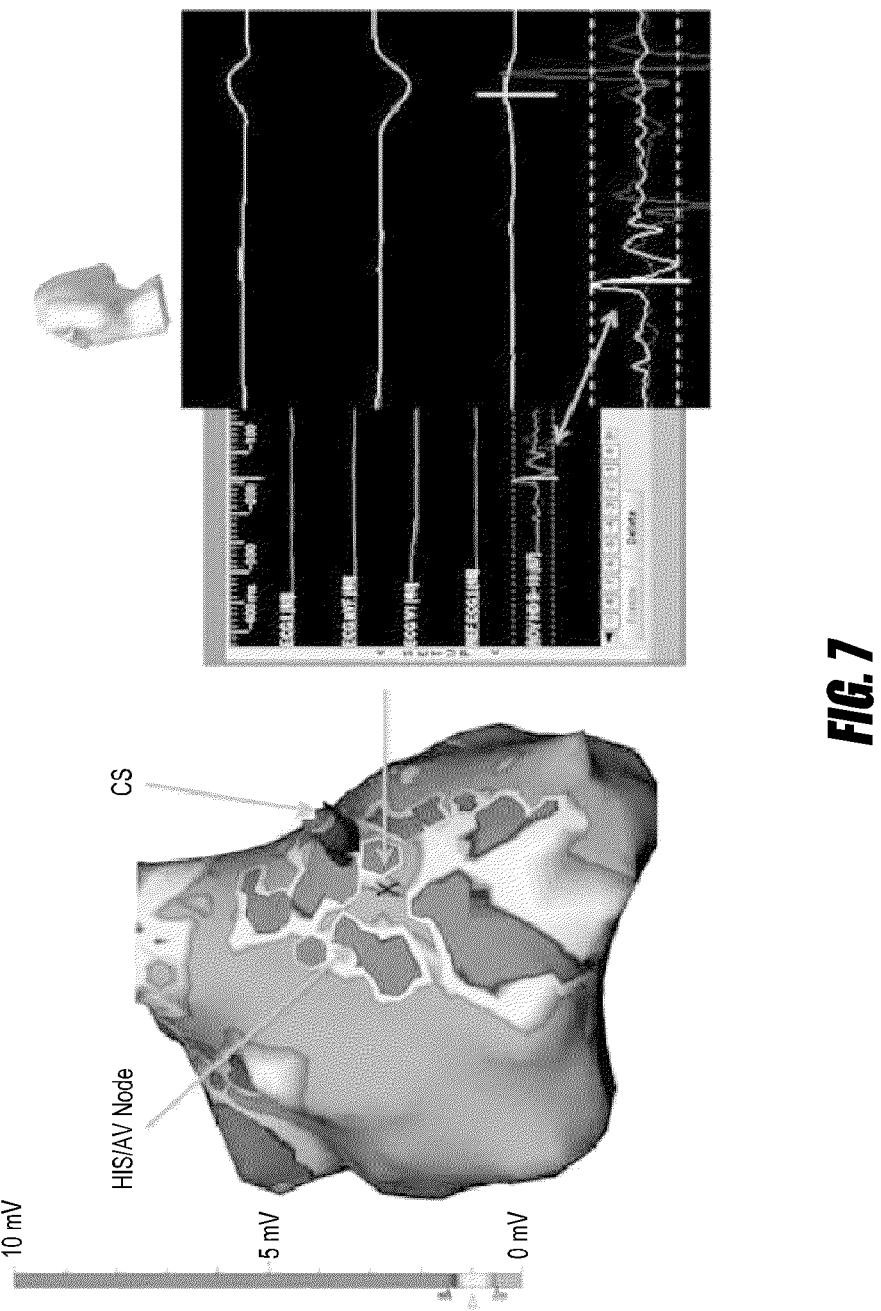
FIG. 7 illustrates a typical slow pathway potential recorded from a point within a low voltage bridge (at point X). Ablation at this site was successful.

By evaluating the electrograms within and immediately outside the low voltage bridge, AV ratios can be assessed. In most cases, a slow pathway potential was observed and these are consistent with those described by Haissaguerre et al. (FIG. 7).

In this example study, a method for direct visualization of the slow pathway by using voltage gradient mapping and low voltage bridge identification was used. One advantage of this approach in certain embodiments is the ability to precisely target the slow pathway within the triangle of Koch, as well as, to provide a definitive endpoint for ablation in patients where the tachycardia may not be inducible. While conventional approaches for AV nodal modification have proven to be successful, multiple slow pathways, anatomic challenges, and interprocedure recurrences, may complicate and prolong such procedures. Additionally, there is an increased risk for damage to the AV node with a conventional step-wise approach to targeting the slow pathway. Commonly, if the initial lesion is unsuccessful, the ablation catheter is advanced toward the apex of the triangle of Koch, increasing the risk of heart block associated with energy application. Definitive identification of the slow pathway location would minimize such a risk, since the catheter is positioned in response to the low voltage bridge rather than empiric anatomic location or electrogram characteristics.

In this example study, the critical slow pathway connections within the triangle of Koch were correctly identified in all patients. While a dedicated multipolar mapping catheter can be used, it is important to note that this technique can also be used with a standard quadrupolar ablation catheter, significantly decreasing both the cost and the time required to create the voltage gradient maps. Therefore, the additional time required to create the voltage gradient map may be offset by the increased efficiency and safety of this technique for slow pathway ablation. Further studies can assess the value of routine voltage gradient mapping during AVNRT ablation.

Figure 3E:
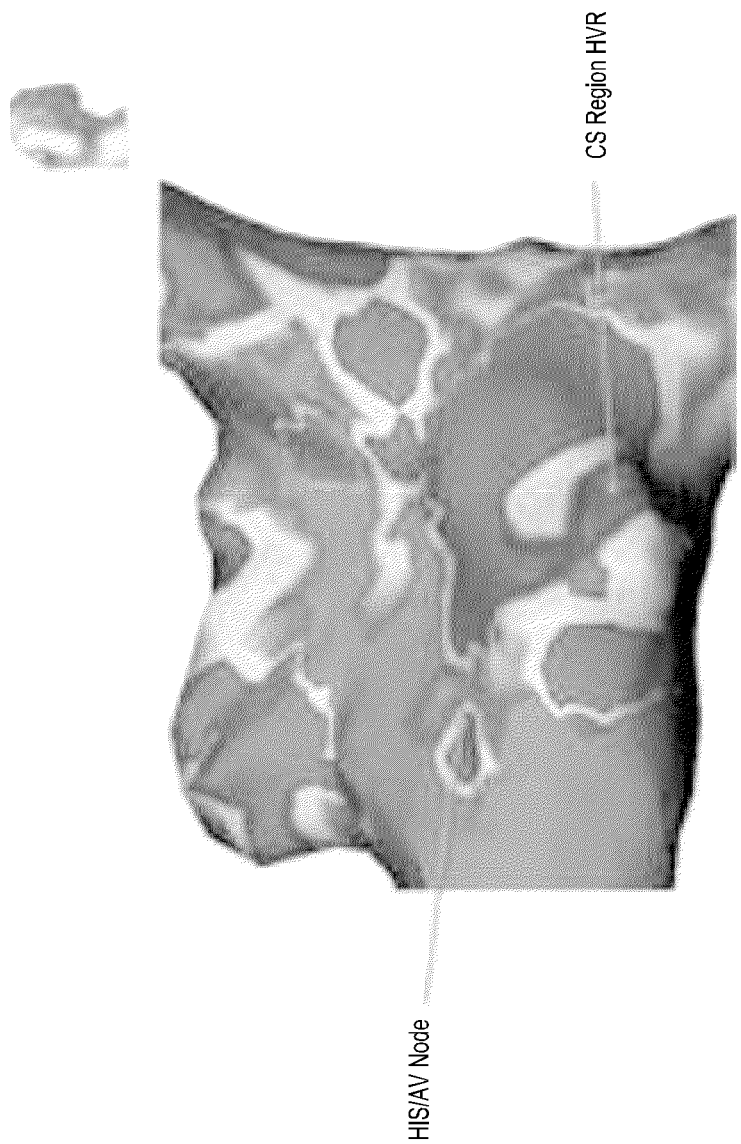
FIG. 3E illustrates that in patients without dual AV Nodal physiology, there is only one voltage tract from the CS Os to the AV Node.

To properly identify the slow pathway associated low voltage bridge, the anatomic relationship to the AV Node is helpful to clearly understand. The AV node is found at the apex of Koch's triangle, formed by the CS Os at the floor, the septal leaflet of the tricuspid valve at the medial margin, and the tendon of Todaro at the lateral margin (FIG. 1A). The AV node appears as a low voltage bridge at the anterior superior tricuspid annulus in the expected anatomic position (FIG. 3E). This low voltage bridge should not be identified as a slow pathway associated low voltage bridge. In contrast, the slow pathway associated low voltage bridge is observed to connect the high voltage region at the CS Os to the AV nodal region. This is usually in the form of a discrete low voltage bridge just superior and anterior to the CS Os (type I). However, in some patients, the slow pathway low voltage bridge is a narrow band between adjacent high voltage regions, rather than existing as an isolated low voltage bridge (type II).

In this example study, low voltage bridges were observed within the triangle of Koch and were consistent with the location of the slow pathway previously described clinically. Regardless of baseline voltage characteristics, following successful ablation, the connection between the region surrounding the CS Os and the AV node are significantly modified and demonstrate an absence of low voltage bridging between the regions.

The fluoroscopic location of the slow pathway identified by voltage gradient mapping conforms to conventional ablation strategies previously described. However, in some patients, the voltage gradient map directed location was outside the usual expected location, as previously noted (FIGS. 4A and 4B). In such cases, conventional anatomic or electrophysiologic criteria may not successfully identify the correct slow pathway location and result in treatment failure or complication.

In patients where there is a documented history of tachycardia, but an inability to induce AVNRT in the electrophysiology lab, conventional ablation techniques cannot accurately predict success unless there is absence of slow pathway function. However, as previously noted, the presence of dual physiology and isolated AV nodal echos is also considered an endpoint for successful ablation, albeit, less certain long term success. Because the voltage gradient mapping can be used to determine the success of the ablation procedure, the underlying atrial substrate can be assessed, and therefore long-term success can be better achieved and objectively documented.

The value of the voltage gradient mapping can be greatly influenced by the ability to obtain sufficient sampling of electrograms within the areas of interest (triangle of Koch). Errors can be introduced by inadequate voltage data sampling within the triangle of Koch, reducing the utility of this method for identifying critical slow pathway low voltage bridges. Also, the data in certain embodiments should be reviewed in order to validate the data sampled and eliminate any ventricular voltage recordings or artifact. Although accurate, creating a voltage gradient map may add additional time for successful ablation of AVNRT.

The morphology of the slow pathway low voltage bridge may be quite varied. These may appear as long low voltage bridge fibers (Type I), or as short connections between high voltage regions within the triangle of Koch, connecting the CS Os to the AV Nodal region (Type II). As a result, the slow pathway related low voltage bridge may be challenging to identify. Review of the data points within the low voltage bridge provides a way to identify low voltage bridges that should be targeted for ablation by the presence of slow pathway potentials.

Example Study 2

Voltage gradient mapping (VGM) within the cardiac chambers can be used to image cardiac substrate and identify focal fiber inputs that connect cardiac endocardium. For example, low voltage bridges (LVB) are found consistently within cardiac tissue. When LVBs connect high voltage regions (HVR), they are associated with specific electrophysiologic effects, attributable to both normal and abnormal myocardial conduction. VGM can be used in certain embodiments to create a global substrate map, identifying selective fiber inputs, enhances the understanding of basic electrophysiology, and facilitates successful identification of appropriate ablation targets.

In another study, all patients underwent consent for electrophysiology studies including mapping and ablation. Voltage Gradient Maps (VGM) were created using an Ensite (St. Jude Medical) with NAVX and either an HD mapping catheter (St. Jude Medical) or a Constellation (Boston Scientific). Three-dimensional (3D) geometries were constructed and utilizing a P-P analysis, voltage limits were adjusted between 1.5 and 1.2 mV high with the low voltage adjusted until bridging was observed between high voltage regions (HVR). These low voltage bridges (LVB) constituted regions of interest in evaluating substrate links within the chamber. Criteria for defining important LVBs were the presence of a voltage gradient within the LVB, connection to isolated HVRs, and the ability to demonstrate a narrow connection from one region to another. Abnormal LVBs were ablated using either radiofrequency energy (60 W/60 degrees) or cryoablation (Freezor Max CryoCath). Repeat VGMs were created and compared to pre ablation maps. Confirmation of successful ablation was defined by inability to induce the clinical arrhythmia following ablation therapy.

In all patients, substrate was clearly identified and ablation of LVBs resulted in termination of the arrhythmia or inability to re-induce the tachycardia. One patient with an automatic atrial tachycardia had no associated LVB at the site of earliest activation. However, in another patient with an automatic atrial tachycardia, an LVB was associated with the site of earliest activation. This finding suggests there may be several mechanisms for the initiation of automatic atrial tachycardia (see, Cox, J. L., "The surgical treatment of atrial fibrillation,"

Figure 8A:
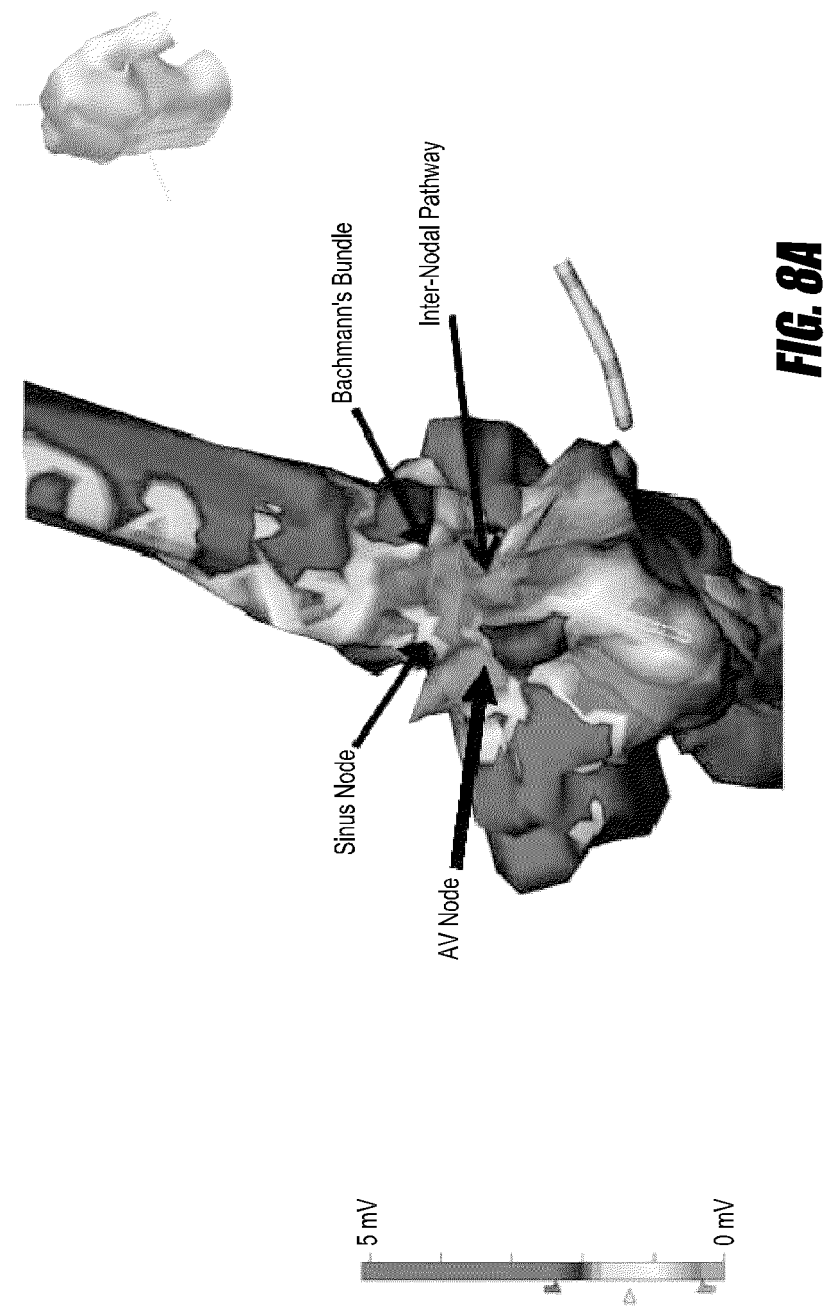
FIG. 8A illustrates fibers from the Sinus Node cross the atrial roof and forming Bachmann's Bundle and the intermodal pathways.
Figure 8B:
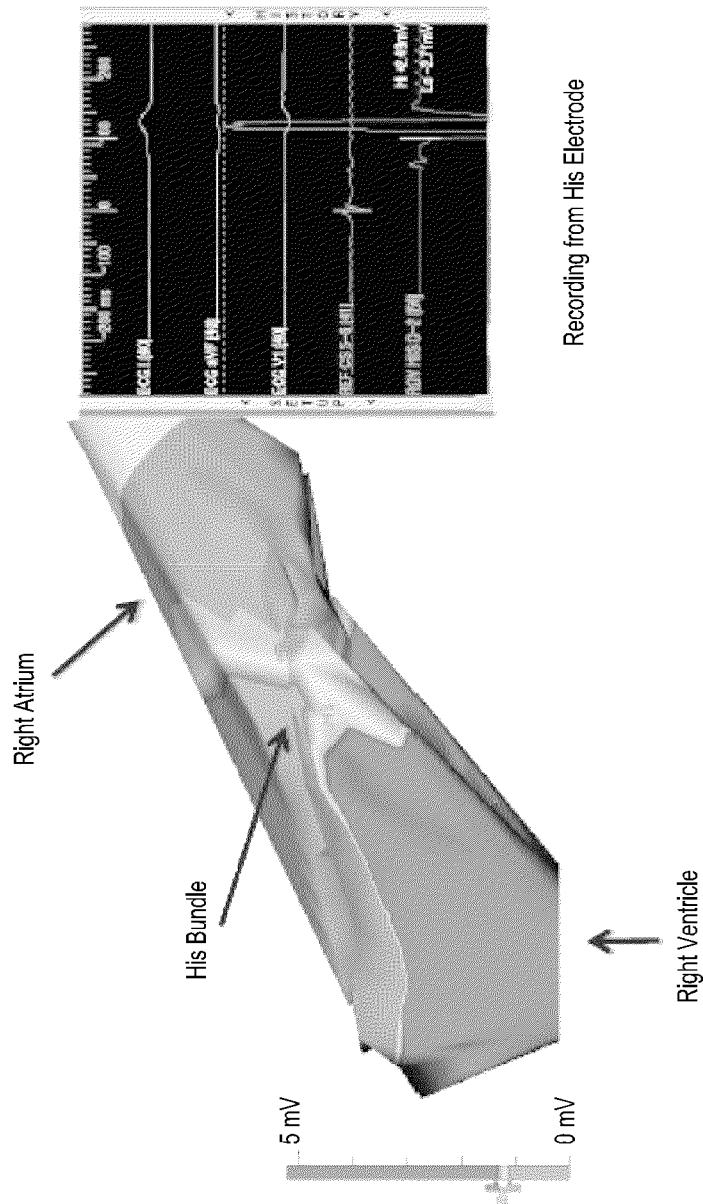
FIG. 8B illustrates the AV Node and His Bundle which appears as a LVB connecting the Right Atrium and the Right Ventricle.

J. Thorac. Cardiovasc. Surg., 1991 April; 101 (4):584-92, IV. Surgical technique). Normal conduction structures were also identified with this method, including the AV Node, Internodal pathways, and Bachmann's Bundle (FIGS. 8A and 8B). Table 1 lists the structures identified via VGM.

TABLE 1

| Rhythm | Structure | Associated LVB | Figures |
|---|---|---|---|
| Sinus | AVN/His | Yes | 8B |
|  | Inter Nodal Pathway | Yes | 8A |
|  | Bachmann's Bundle | Yes | 8A |
| AV Nodal Re Entry Tachycardia | Slow Pathway | Yes | 9A and 9B |
| Accessory Connection Tachycardia | Kent Bundle | Yes | 10 |
| Atrial Fibrillation | PV input | Yes | 11A and 11B |
|  | Atrial Chamber | Yes | 12A and 12B |
|  | SVC | Yes | 13A and 13B |
| Atrial Flutter | Isthmus-Caval | Yes | 14A |
| Atypical Flutter | Postero-Lateral Wall | Yes | 14B |
| Ventricular Tachycardia | Regions of Slow Conduction | Yes | 15 |
| Automatic Atrial Tachycardia | Micro-reentry Circuit | Observed but not Consistent * | 16A and 16B |
| Automatic Ventricular Tachycardia/PVCs | Micro-reentry Circuit | Observed but not Consistent | 17 |
| Ventricular Fibrillation | Fractionated Conduction | ? | — |

FIGS. 9A, 9B, 10, 11A, 11B, 12A, 12B, 13A, 13B, 14A, 14B, 15, 16A, 16B, and 17 demonstrate examples of LVBs involved in tachycardia propagation. In all cases, ablation of focal LVBs resulted in profound changes in the underlying cardiac substrate. Loss of LVB function correlated with the clinical success observed in the post ablation VGMs.

Case Studies

Voltage gradient mapping was successful in identifying critical connections in a number of cardiac arrhythmias in the aforementioned studies. Voltage settings were adjusted as previously described and were individualized based upon the actual voltage recorded.

AV Nodal Re-Entry Tachycardia

Figure 9A:
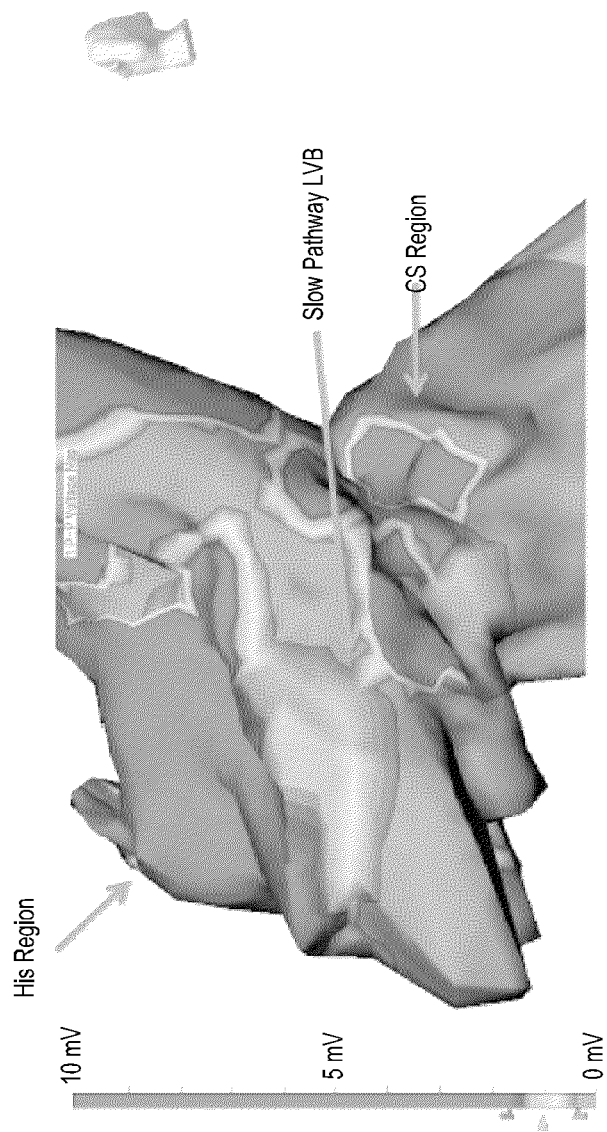

Most ablation techniques utilized for slow pathway ablation focus on anatomic and electrophysiologic criteria. (See, e.g., Lee et al., "Atrioventricular node anatomy and physiology: implications for ablation of atrioventricular nodal reentrant tachycardia," Curr. Opin. Cardiol., 2009 March, 24 (2): 105-12; Lee et al., "Catheter modification of the atrioventricular junction with radiofrequency energy for control of atrioventricular nodal reentry tachycardia," Circulation, 1991 March, 83 (3):827-35.) However, in patients with unusual anatomy or multiple inputs, ablation of the slow pathway can be challenging. Direct visualization of the slow pathway would facilitate successful ablation and enhance the safety. FIGS. 9A and 9B demonstrate the appearance of the slow pathway, before ablation, and after ablation. Ablation of the connecting LVB results the loss of the HVR connected to the AV nodal region, and correlates with inability to re-induce tachycardia.

Accessory Pathway Mediated Tachycardia

Figure 10:
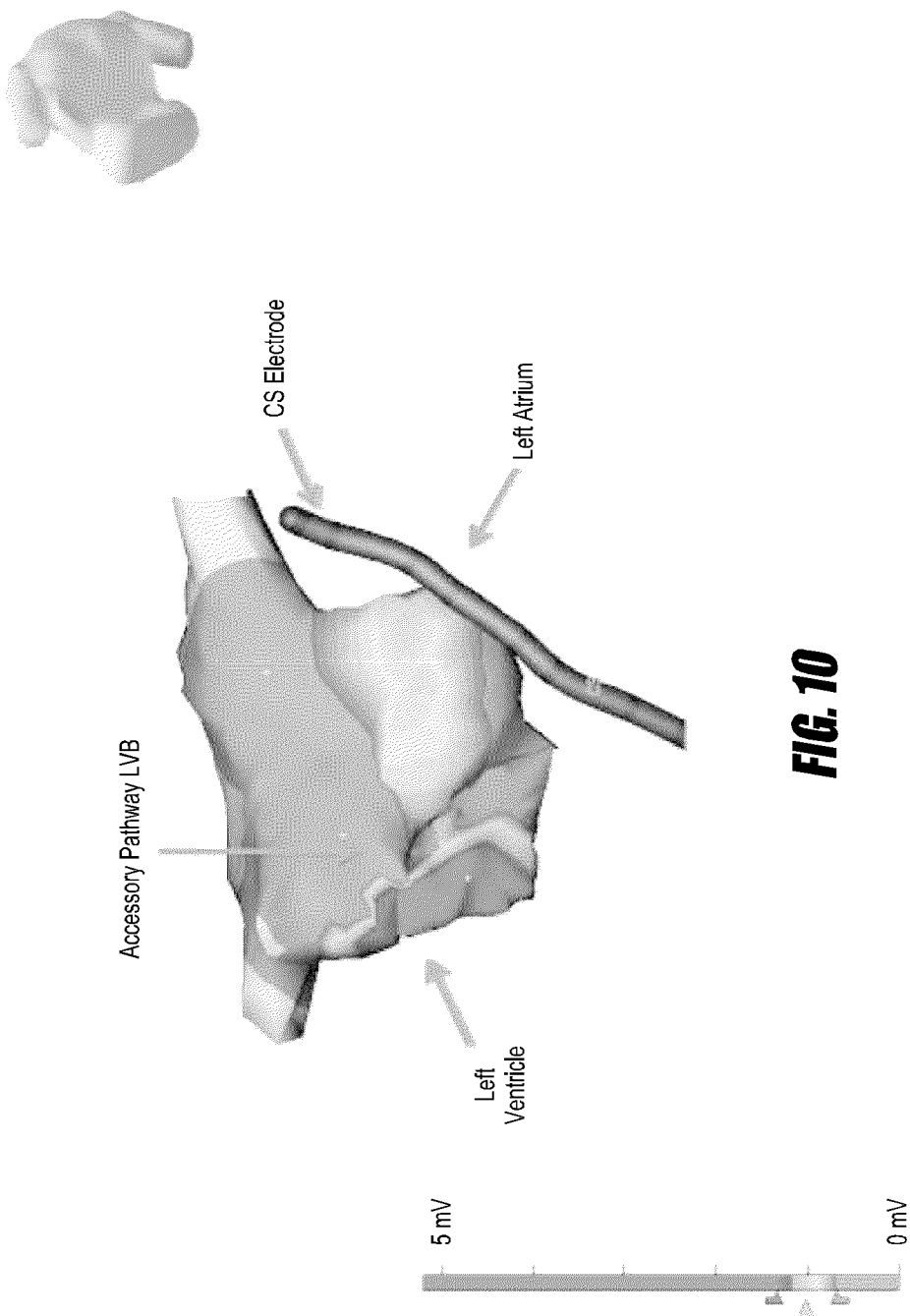
FIG. 10 illustrates the accessory connection associated with Wolf-Parkinson-White Syndrome (Pre-excitation) of the LA Mitral annulus, demonstrating the presence of a LVB connecting the LV and LA. Ablation at this site terminated tachycardia and pre-excitation was no longer observed.

Localization of the site of pathway insertion is advantageous for successful ablation of pre-excitation and accessory pathway mediated tachycardia. In FIG. 10, mapping at the mitral annulus reveals a connection between the left ventricle and left atrium. Recordings from within this LVB, demonstrate a short AV interval consistent with an excellent ablation target. Energy applied at this site resulted in loss of pre-excitation.

Atrial Fibrillation

Figure 11A:
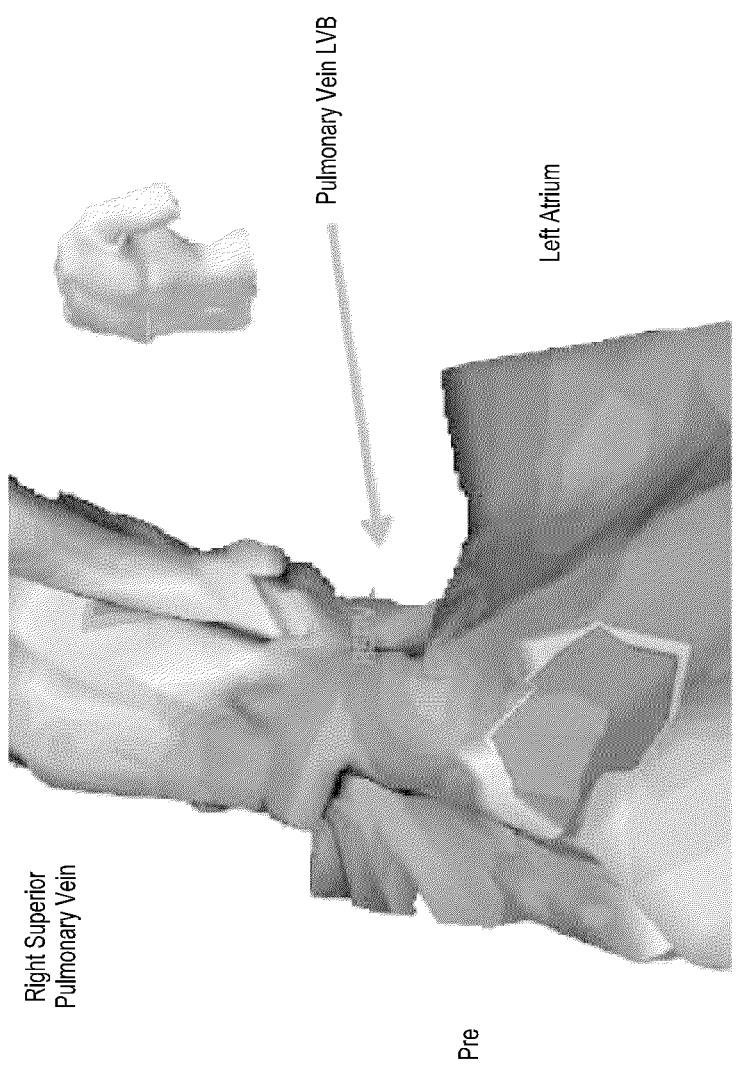
FIGS. 11A and 11B illustrate the Pulmonary Vein LVB Input, before and after ablation, respectively. The pulmonary veins are electrically connected to the LA via LVBs. These may be singular connections, or associated with multiple fiber inputs. Typically, the LVB origin is within the LA, and isolation can be accomplished by ablation outside the vein. Following ablation of the LVB, the pulmonary vein is isolated.
Figure 11B:
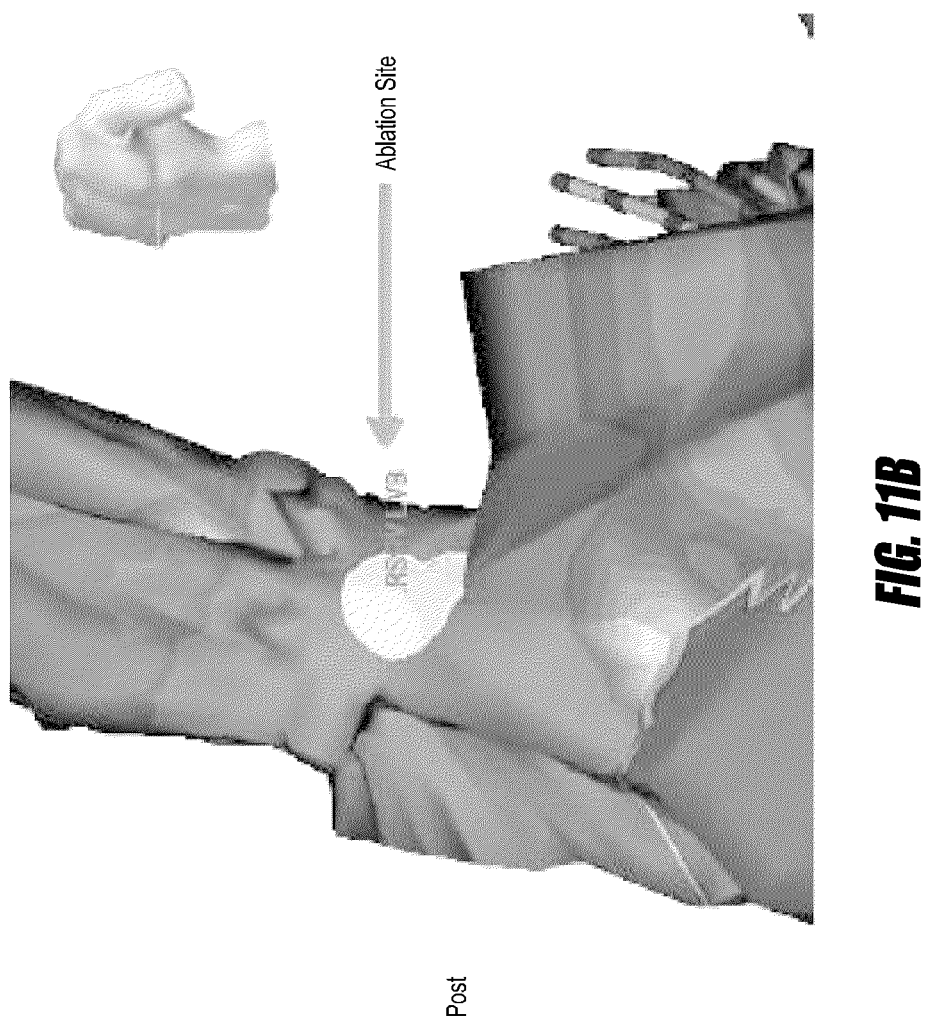
Figure 12B:
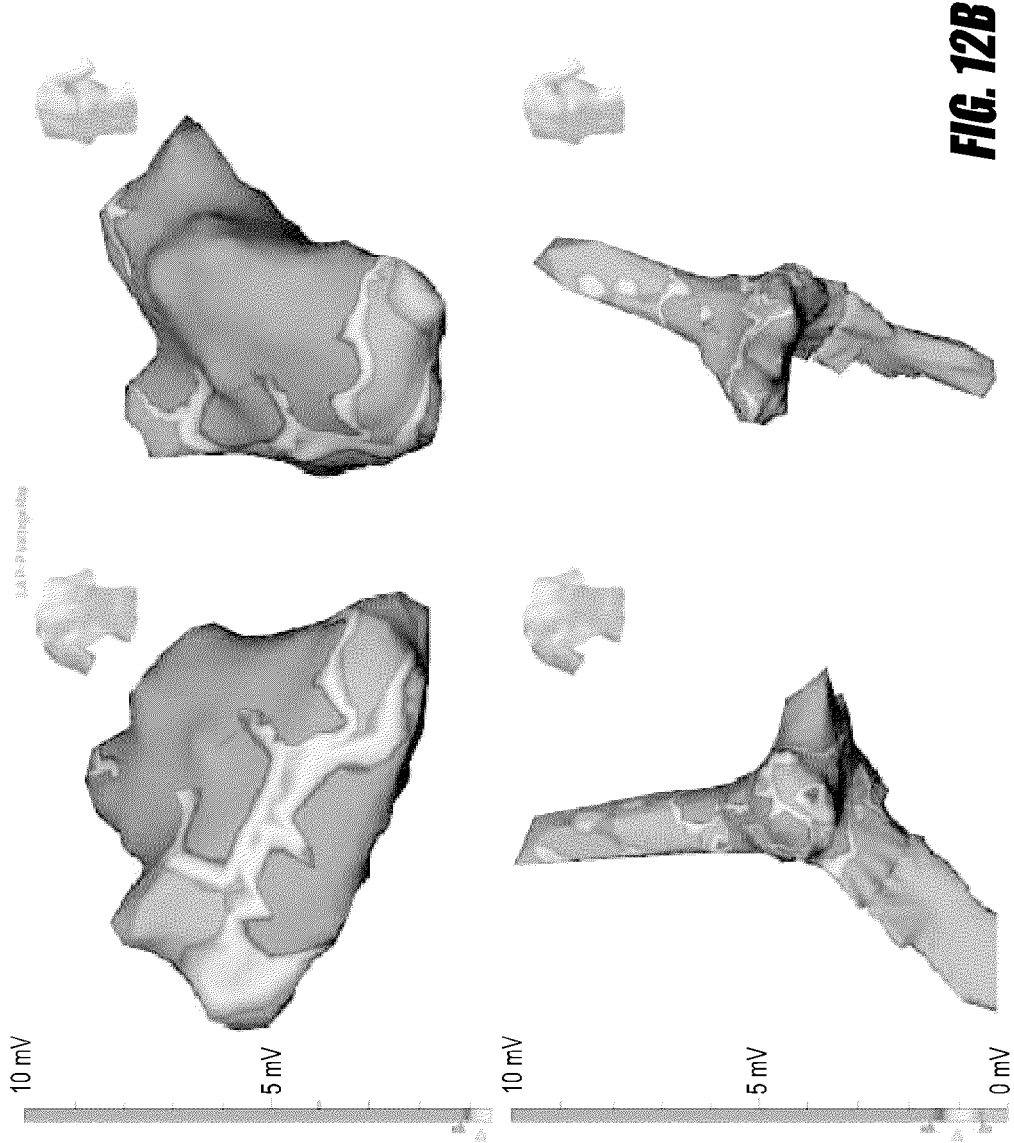
FIG. 12B illustrates a VGM from a patient without a history of AF. Note large HVRs and few LVBs compared to the patient with AF in FIG. 12A.
Figure 13B:
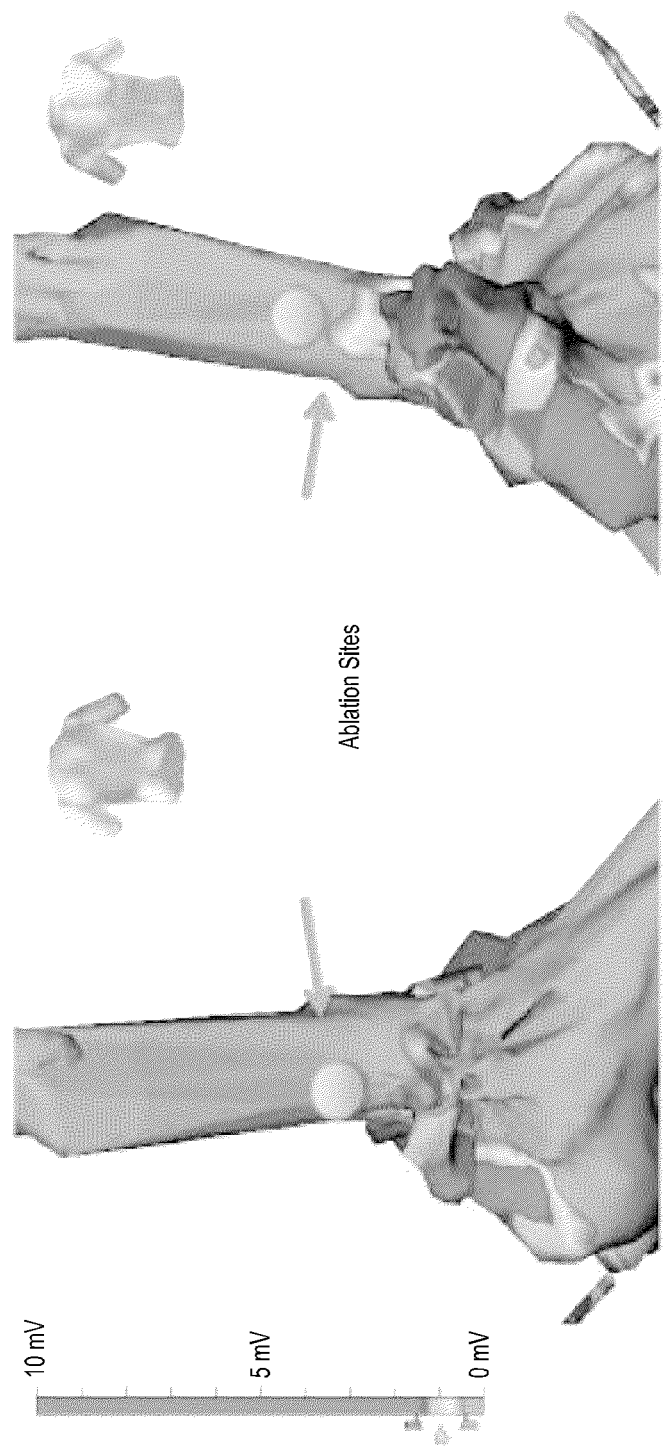
Figure 14A:
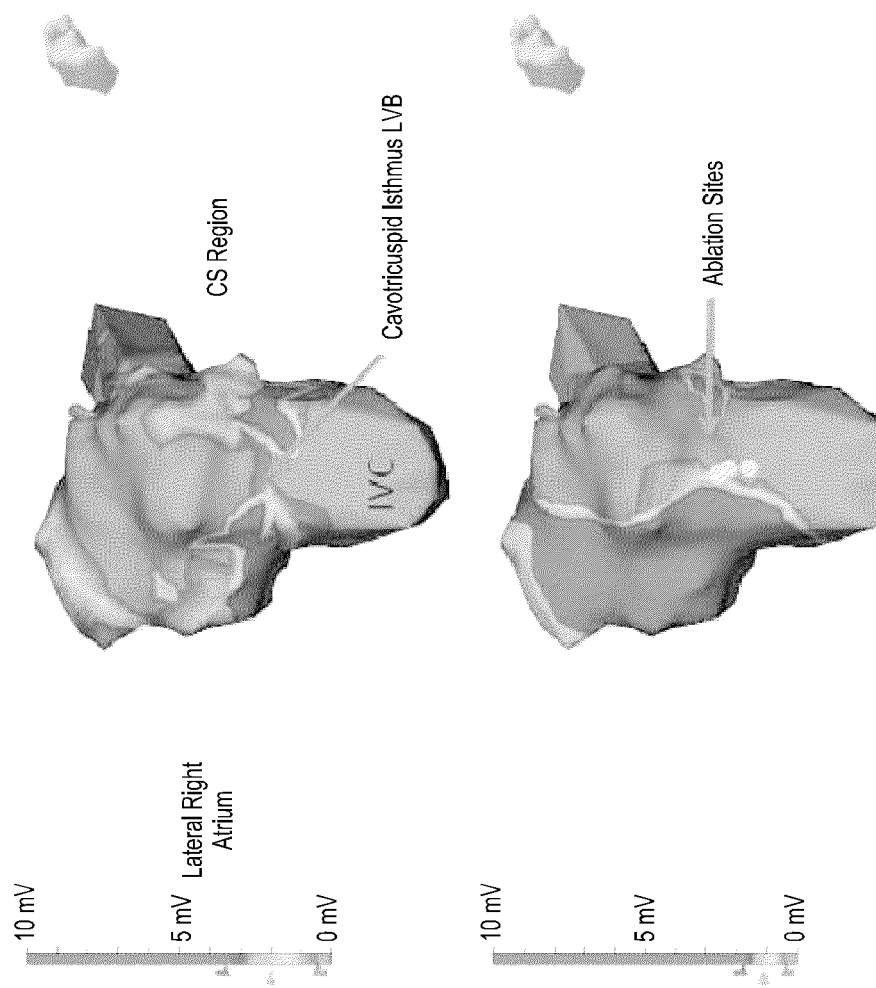
FIG. 14A illustrates a LVB at the Cavotricuspid Isthmus, pre-ablation and post-ablation, where isthmus dependent atrial flutter can be recognized by the presence of a LVB within the cavotricuspid isthmus region.
Figure 14B:
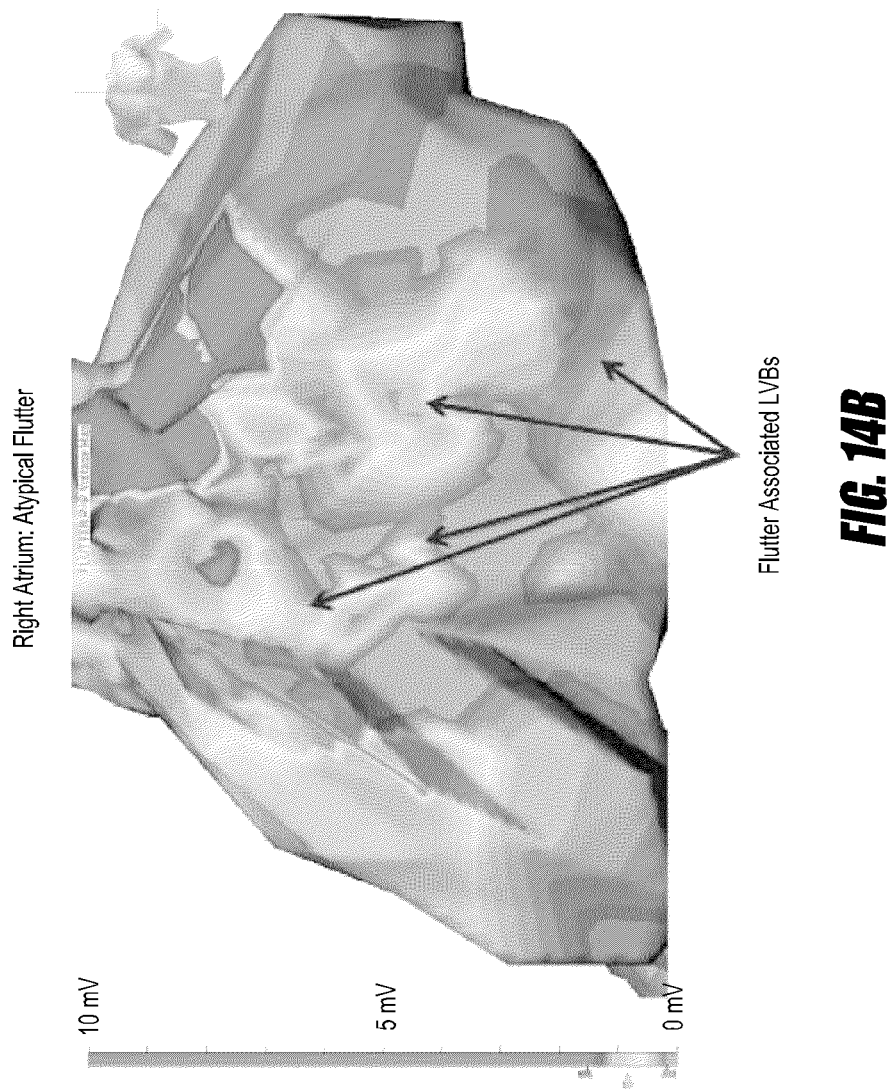
FIG. 14B illustrates LVBs observed along the lateral posterior Right Atrium toward the Right Atrium Cristea. The LVBs at the Postero-Lateral Wall are associated with an Atypical Atrial Flutter, with numerous LVBs noted in the lateral wall of the right atrium. Ablation of these bridges resulted in flutter termination.

Numerous studies have demonstrated the clinical utility of ablation therapy for atrial fibrillation (AF). (See, e.g., O'Neill et al., "Catheter ablation for atrial fibrillation," Circulation, 2007 Sep. 25; 116 (13):1515-23; Shawnee et al., "Five-year outcomes after segmental pulmonary vein isolation for paroxysmal atrial fibrillation," Am. J. Cardiol., 2009 Aug. 1; 104 (3):366-72.) Current approaches are based on the belief that AF can be treated by ablation of initiating foci. The exact mechanism for propagation and maintenance of AF remains largely unknown. As a result, the clinical outcome of ablation therapy cannot be predicted, nor can the mechanisms for ablation failure be precisely determined. Histological evidence suggests that progressive fibrosis and loss of intercellular connections is associated with progressive disease. (See, e.g., Kourliouros et al., "Current concepts in the pathogenesis of atrial fibrillation," Am. Heart J., 2009 February; 157 (2): 243-52.) Visualization of the underlying atrial substrate would shed light on the fundamental pathophysiology in AF and facilitate successful ablation therapy. FIGS. 11A and 11B demonstrate LVB connecting the Pulmonary Veins and following LVB ablation, the PV is shown to be successfully isolated. FIG. 12A shows multiple LVBs connecting multiple HVRs within both the right and left atrium. Ablation of these LVBs results in striking changes within the atrial endocardium. The VGM from a patient without atrial fibrillation atrium is seen in FIG. 12B. Note that the normal atrium demonstrates relatively homogeneous voltage compared to the atrium of patient with atrial fibrillation. This voltage fractionation shows HVR linked by LVBs. As seen in FIGS. 13A and 13B, LVBs also link the right atrium and the SVC. Ablation of these LVBs results in SVC isolation.

Atrial Flutter

The mechanism for reentry in atrial flutter has been well described. (See, e.g., Sawhney et al., "Diagnosis and management of typical atrial flutter," Cardiol. Clin., 2009 February; 27 (1):55-67, viii.) Ablation at the cavotricuspid isthmus terminates atrial flutter and the presence of bidirectional block predicts a favorable long-term outcome. (See, e.g., Földesi et al., "Atrial flutter: arrhythmia circuit and basis for radiofrequency catheter ablation," Ital. Heart J., 2003 June; 4 (6):395-403.) Despite this finding, anatomic variation or prior surgical intervention can complicate the ability to identify critical regions of the reentry circuit. VGM can identify LVBs, which are associated with propagation of the reentry tachycardia (see FIGS. 14A and 14B) in both typical and atypical atrial flutter. Ablation of these LVBs results in tachycardia termination, bidirectional block, and inability to re-induce the tachycardia.

Ventricular Tachycardia

Figure 15:
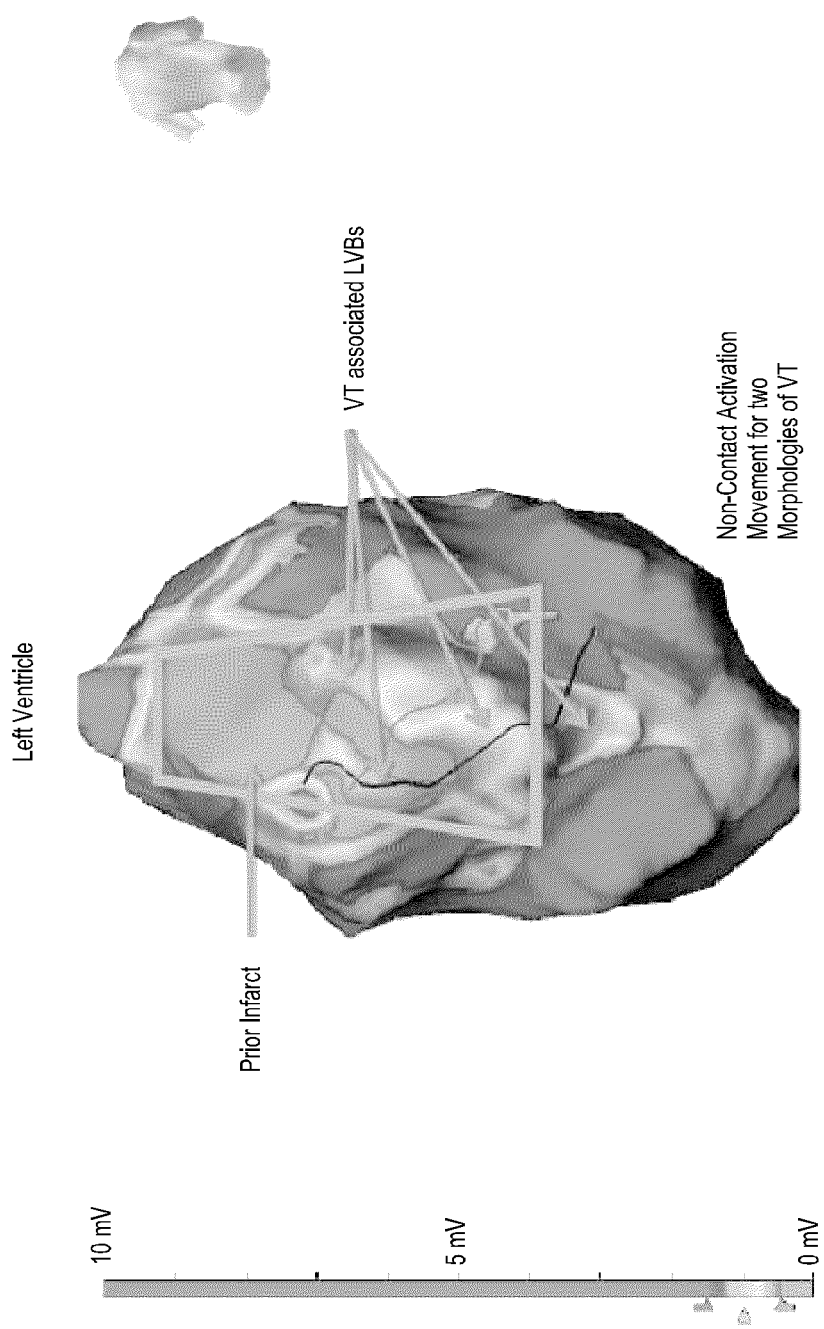
FIG. 15 illustrates LVBs associated with an Ischemic Ventricular Tachycardia, pre-ablation and post-ablation, with a non-contact map with an activation track of two VT morphologies overlay a VGM of the Left Ventricle. Both morphologies utilize a common LVB within the Left Ventricle scar. The ablation of the LVB terminated tachycardia.

Voltage substrate maps have been constructed to identify low voltage substrate within the ventricle. Ablation lines placed across viable tissue connecting adjacent substrate tissue has been effective in treatment of reentry ventricular tachycardia. (See, e.g., Klemm et al., "Catheter ablation of multiple ventricular tachycardias after myocardial infarction guided by combined contact and noncontact mapping," Circulation, 2007 May 29; 115 (21):2697-704; Hsia et al., "Characterization of endocardial electrophysiological substrate in patients with nonischemic cardiomyopathy and monomorphic ventricular tachycardia," Circulation, 2003 Aug. 12; 108 (6):704-10.) VGM provides functional information regarding focal fiber inputs in regions of slow conduction that are required for propagation of the tachycardia. FIG. 15 displays a VGM from a patient with multiple VT morphologies. Non-contact activation plot is traced over a VGM and demonstrates that LVBs are associated with tachycardia propagation.

Automatic Atrial and Ventricle Tachycardia

Figure 16B:
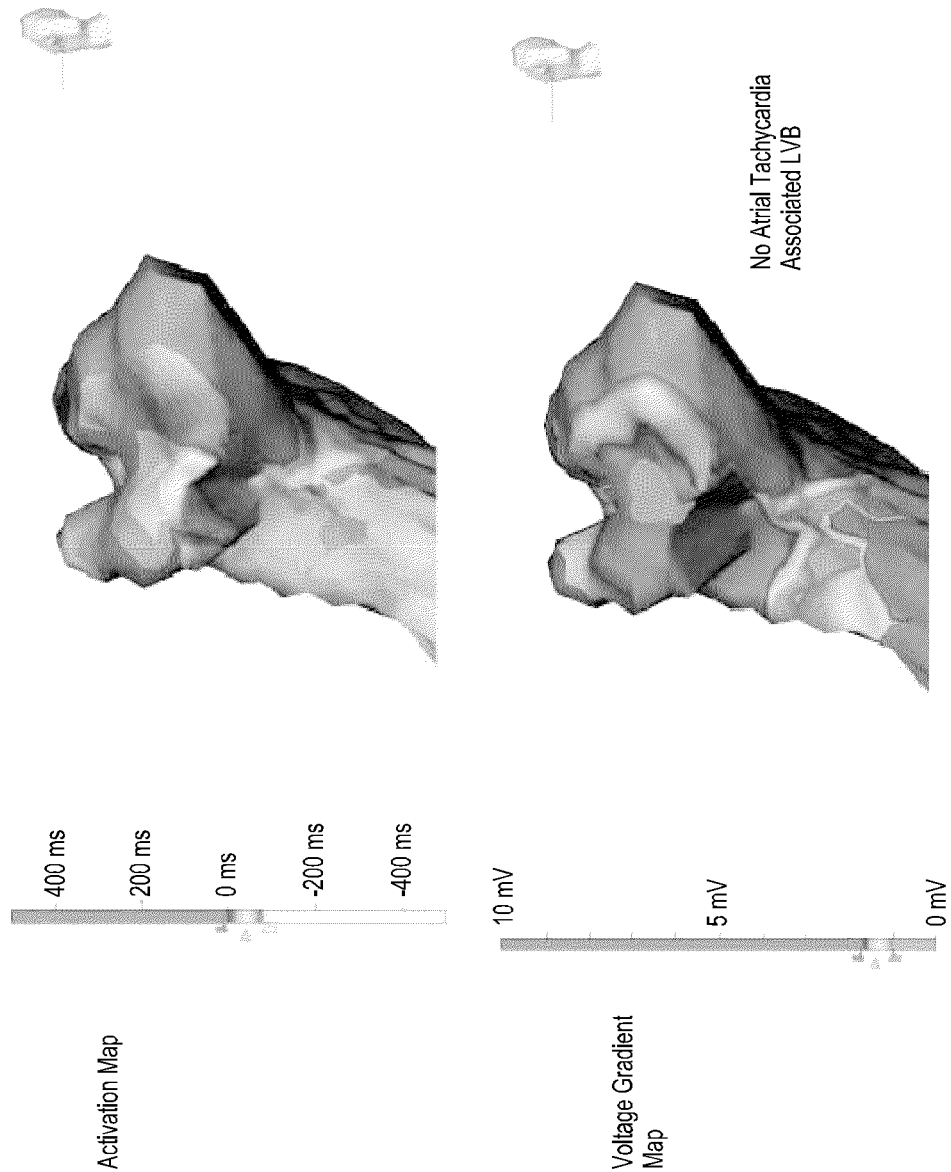
FIG. 16B illustrates an automatic atrial tachycardia not associated with an LVB, with both an activation map and VGM.
Figure 17:
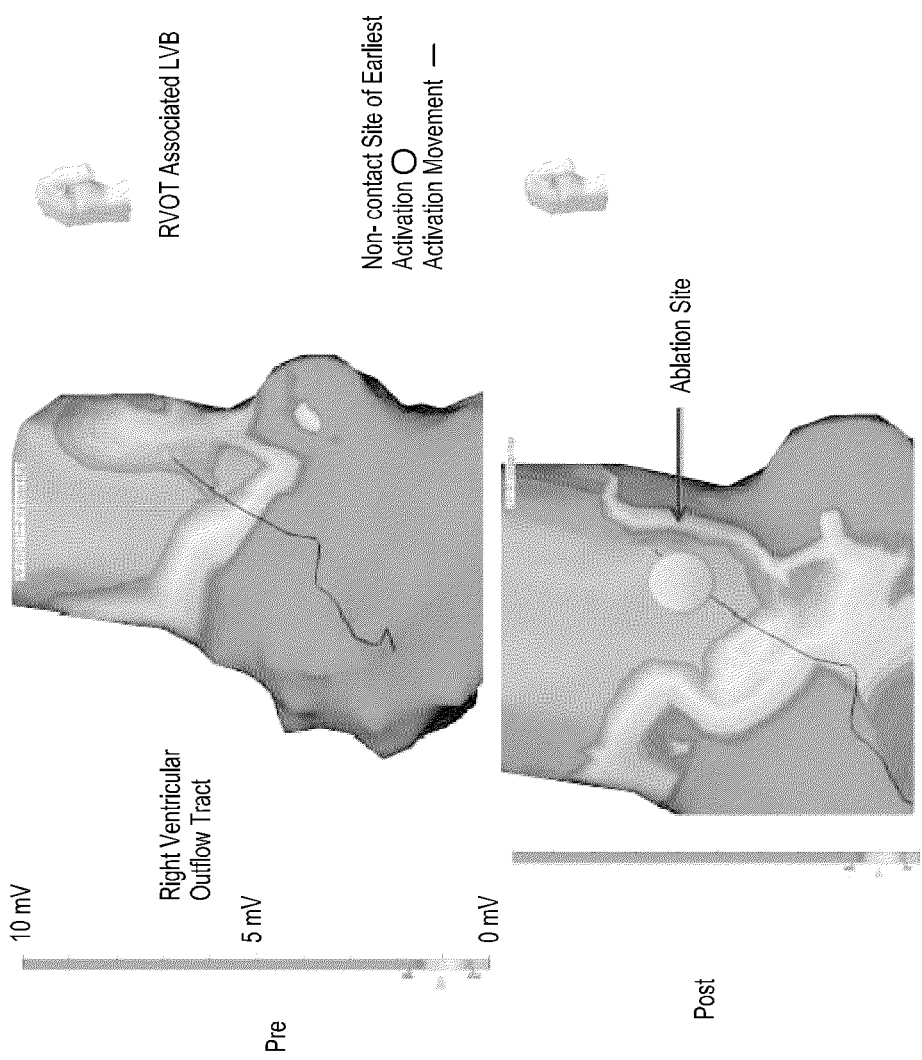
FIG. 17 illustrates an automatic Ventricular Tachycardia/PVCs (RVOT Tachycardia), with a non-contact activation track plotted and passing within a LVB. This tachycardia was catecholamine sensitive and was terminated by ablation of the LVB. Post ablation, the LVB is absent and the VGM is significantly altered.

One surprising observation is that some automatic tachycardias are associated with LVBs. When found, these LVBs correspond to the site of earliest endocardial activation confirmed by contact activation mapping. This observation suggests that in such cases, the tachycardia may be mediated by micro reentry within the tissue. In a study by Markowitz et al. ("Adenosine-Insensitive Focal Atrial Tachycardia: Evidence for De Novo Micro—Re-Entry in the Human Atrium," J. Am. Coll. Cardiol., 2007; 49:1324-1333), it was found that adenosine sensitive tachycardias appear to be consistent with micro reentry, while non-adenosine sensitive tachycardias have focal origins. FIG. 16A shows an LVB associated atrial tachycardia and FIG. 16B shows a non-LVB associated atrial tachycardia, both with corresponding activation maps. FIG. 17 shows an example of LVB associated RVOT tachycardia. Both contact and non-contact mapping revealed the origin and activation pathway of the tachycardia. VGM demonstrated the presence of a LVB corresponding to both the early activation site and the activation tract within the right ventricle. Ablation at this site terminated tachycardia and repeat mapping demonstrates absence of a LVB.

Discussion

Several considerations are important in evaluating the validity of the VGM methodology. Obtaining a sufficient sampling of local voltages within the geometry is important to develop reliable substrate maps. If insufficient points are obtained, the voltage map accuracy is severely impaired. When sufficient voltage points are obtained, the substrate VGM ceases to demonstrate significant changes despite increased sampling. Second, a reliable geometry can be created and the reference point can remain stable. Catheter points sampled outside the geometry impair the accuracy of the map. For example, external points that are greater than 5 mm off the geometry can be excluded. Additionally, internal projection can be minimized and interpolation adjusted to the lowest acceptable level.

This example study presents methodology with validation, and provides proof of concept that an accurate substrate map can be created and utilized for analysis of a variety of clinical arrhythmias.

In certain embodiments, VGM offers significant advantages over contemporary approaches to arrhythmia mapping. By visualizing the cardiac substrate directly, critical links in the propagation and maintenance of the arrhythmia may be easily and successfully targeted for ablation. Additionally, since the VGM represents underlying tissue substrate, it is independent of the underlying rhythm and activation mechanism. Therefore, mapping can proceed in the absence of the clinical arrhythmia, something not possible when creating activation maps.

This mapping approach represents a departure from traditional mapping techniques. It permits evaluation of the cardiac substrate and identifies the ablation target without resorting to activation maps. By direct LVB visualization, selective fiber inputs can be identified, making successful ablation targets easier and more precisely recognized. This should improve overall ablation success in a wide variety of clinical settings.

Without being bound by theory, it is thought that LVBs represent focal fiber inputs linking HVRs together. This observation offers insights into the mechanisms of arrhythmia propagation within the cardiac chambers. When the LVBs are ablated within the atria, HVRs are often converted to LVRs or have no voltage recorded at all. The latter suggests that these HVRs have protected input, and the loss of activation within that region occurs when its LVB is severed. This is seen in slow pathway ablation, Pulmonary Vein Isolation, and LVB ablation in atrial fibrillation. Therefore, LVBs likely represent focal fiber inputs that uniquely connect endocardial LVRs and HVRs.

The concept that LVBs represent underlying cardiac substrate and critical fiber linkages is confirmed by the observation that ablation of the appropriate LVB results in termination of the tachycardia, e.g., AVNRT, AVRT, or atrial flutter. Additionally, the absence of LVBs is associated with non-inducibility. We can categorize these LVBs the following way:

Anatomic LVBs are associated with normal conduction fibers such as the His bundle, the Inter-nodal fibers between the Sinus Node and the AV Node, and Bachmann's Bundle.

Reentry LVBs represent "normal" focal fibers that participate macro re-entry circuits such as the slow pathway in AV nodal reentry, or accessory pathways in reciprocating tachycardia.

Pathologic LVBs represent abnormal substrate such as damaged endocardial fibers observed in ventricular arrhythmias, atrial flutter, automatic tachycardia with micro re-entry, or atrial fibrillation.

Although the finding that LVBs are ubiquitous in cardiac physiology may seem surprising, it is also consistent with our understanding of cardiac arrhythmias. For example, it is not surprising that LVBs act as regions of slowed conduction. Local electrograms collected within LVRs demonstrate decreased activation slopes (dv/dt) and slow conduction as visualized by activation loops. Pacing within LVBs at the cavotricuspid isthmus, demonstrates concealed entrainment (see, Stevenson et al., "Identification of reentry circuit sites during catheter mapping and radiofrequency ablation of ventricular tachycardia late after myocardial infarction," Circulation, 1993 October; 88 (4 Pt 1):1647-70), the hallmark of identifying a site for successful atrial flutter ablation. As singular connections, LVBs create protected inputs that provide a mechanism for classical reentry to occur.

In atrial fibrillation, multiple LVBs provide endocardial linkage to create an atrial syncytium. Such a structure would act as a wavelet reservoir, sustaining and propagating atrial fibrillation. AF ablation targeting LVBs can be an effective treatment for AF, since ablation of LVBs results in "delinking" the endocardium, thereby preventing wavelet propagation. Such a postulate would explain both the high rate of success enjoyed by the full surgical Cox MAZE procedure (see, e.g., Cox J. L., "The surgical treatment of atrial fibrillation," J. Thorac. Cardiovasc. Surg., 1991 April; 101 (4):584-92. IV. Surgical technique; Cox J. L. et al., "An 8½-year clinical experience with surgery for atrial fibrillation," Ann. Surg., 1996 September, 224 (3):267-73), which creates extensive division of the atrium, as well as, the moderate level of failure using current catheter based AF solutions. (See, e.g., Bertaglia et al., "Does catheter ablation cure atrial fibrillation? Single-procedure outcome of drug-refractory atrial fibrillation ablation: a 6-year multicentre experience," Europace, 2009 Nov. 3; Katritsis et al., "Long-term follow-up after radiofrequency catheter ablation for atrial fibrillation," Europace, 2008 April, 10 (4):419-24; Cheema et al., "Long-term single procedure efficacy of catheter ablation of atrial fibrillation," J. Interv. Card. Electrophysiol., 2006 April, 15 (3): 145-55.) Failures associated with anatomic directed ablations may result from inadequate LVB disruption. In patients with chronic AF, successful catheter based ablations have proven even more elusive. (See, e.g., Sanders et al., "Complete isolation of the pulmonary veins and posterior left atrium in chronic atrial fibrillation. Long-term clinical outcome," Eur. Heart J., 2007 August, 28 (15):1862-71; Elayi et al., "Ablation for longstanding permanent atrial fibrillation: results from a randomized study comparing three different strategies," Heart Rhythm, 5 (12): 1658-1664.) This likely reflects extensive substrate disease and greater fractionation of the endocardium within the atrium of these patients compared to patients with paroxysmal forms of AF. As demonstrated in FIGS. 11A and 11B, patients with AF have significant endocardial fractionation and multiple LVBs compared to patients without a history of AF. LVBs and endocardial fraction can be observed in increasing frequency in normal hearts as people age, and the number of LVBs observed in patients with AF should correlate with the chronicity of the AF. Targeting atrial substrate with LVB ablation should be a successful approach in patients with AF.

VGM represents a fundamental measurement of tissue substrate that has remarkable consistency with our understanding of both reentrant and traditionally non-reentrant rhythms. It represents a new tool for understanding cardiac substrate and how it influences the development of cardiac arrhythmias. VGM offers significant advantages over activation or routine voltage mapping. By evaluating voltage gradient map within the cardiac chamber, the underlying tissue substrate becomes apparent. Understanding the relationship between the underlying tissue substrate and its role in arrhythmogenisis is advantageous for the development of successful outcomes for ablation therapy. VGM is particularly useful in evaluating rhythms that are not amenable to conventional mapping techniques.

Example Study 3

Atrial Fibrillation

As discussed above, understanding the mechanisms for maintenance and propagation of atrial fibrillation has been elusive. Histology studies have demonstrated the presence of progressive fibrosis and loss of intercellular connections due to gap junction regression. These changes become more pronounced as the AF changes from paroxysmal to chronic forms, e.g., persistent and permanent (PPAF) forms. In 1959, Moe proposed that AF is maintained by wavelets that are in constant collision within the atrium. AF can be maintained as long as there is sufficient tissue mass to maintain multiple wavelets.

Current ablation approaches are primarily anatomic and concentrate on isolation of the pulmonary veins, with successful outcomes thought to be associated with eliminating triggering foci. Initial curative treatment pioneered by Cox, cited above, demonstrated that division of atrial tissue into segments via a "MAZE" procedure prevented AF and offered long-term cures. More recently, electrophysiologists have focused on eliminating triggering foci within the left atrium residing in, or around the pulmonary veins. Regardless of the technology used, ablation therapy is empiric and anatomical. Unfortunately, our understanding of the reasons ablations succeed or fail is unknown, because we have no method for evaluating the underlying atrial substrate and criteria for success. Most reports suggest that patients with paroxysmal forms of AF have better outcomes than patients with persistent or chronic forms of AF, but the reasons for failure are obscure.

Another line of thought has been to map either high frequency low amplitude sites, CFAE mapping, or to target autonomic ganglia found in the left atrial epicardium. Both of these approaches have not demonstrated efficacy similar to anatomic ablation with isolation of the pulmonary veins. More commonly, they are used as adjunct therapy, but their utility is uncertain.

Because of the chaotic nature of the arrhythmia, conventional surface activation mapping has not proved useful. While high density patch mapping of AF has indicated that chaos theory may be applicable, no clear methodology for atrial substrate mapping has been described. Additionally, frequency domain mapping has demonstrated regions of low amplitude and high frequency that were seen as important in perpetuating AF (CFE mapping); however to date, results using selective CFE ablation have been disappointing. Despite continued improvements in catheter and mapping technology, a significant proportion of patients will require multiple procedures, and clinical results in patients with chronic AF have been discouraging.

Ideally, a method to identify abnormal atrial substrate would offer the best chance to understand the underlying atrial disease, as well as, offer the best chance to intervene with ablation. For example, dynamic voltage mapping would be advantageous to use to guide ablation in patients with atrial fibrillation. If it were possible to map atrial substrate, the fundamental structures necessary to maintain and propagate AF would become apparent. Such a model would have implications for the mechanism of AF progression from PAF to chronic AF (PPAF), would be quantifiable, would be measurable in any rhythm, and would be able to define targets for ablation therapy.

In certain embodiments described herein, Voltage Gradient Mapping is used within the left and right atrium to observe high voltage regions (HVRs) that are connected by low voltage bridges (LVBs). These LVBs represent abnormal atrial substrate caused by atrial fibrosis and loss of gap junctions seen in the atrium of AF patients. Targeting these LVB by ablation can eliminate the endocardial fragmentation associated with AF and allow a methodology for successful ablation therapy.

In certain embodiments, VGM and identification of HVR and LVB as described herein provides an easy way to assess underlying atrial substrate. In certain embodiments, isolation of HVR by LVB ablation as described herein results in termination of AF. In certain embodiments, mapping obtained in SR was not different from mapping obtained in AF. In certain embodiments, use of VGM can increase understanding of the atrial substrate, and can offer a rational method to approach atrial fibrillation therapy.

In this example study, we have observed that mapping voltages within the Pulmonary veins and Atrium can provide a map of atrial substrate. Patients undergoing atrial fibrillation ablation had voltage gradient mapping performed. Ablation was targeted to the LVB. Atrial Fibrillation was terminated in these patients following LVB ablation in both the Right and Left atrium. Large areas of low voltage regions became electrically silent following HVR isolation and residual HVR were isolated from other HVR. Importantly, LVBs were observed in all patients and were independent of the rhythm during mapping.

Fifty-four consecutive patients undergoing AF ablation underwent bi-atrial VGM. Following consents, all patients had a complete EP study if in sinus rhythm at the start of the study. Using EnSite NavX™ Navigation and Visualization Technology (St. Jude Medical) and a standard quadrupolar ablation catheter, and a Reflexion™ HD 20 polar catheter (St. Jude Medical) or a Constellation® catheter (Boston Scientific), three-dimensional anatomy was constructed using VGM and voltages obtained in either sinus rhythm (SR) or AF, utilizing a P-P analysis, adjusting voltage limits between 1.5 and 1.2 mV high with the low voltage adjusted until bridging was observed between high voltage regions (HVR). CFE mapping and peak to peak mapping was performed. Regions were then determined to be High Voltage Regions (HVRs) or Low Voltage Regions (LVRs). By adjusting the sensitivity (peak low voltage adjustment), defined regions of low voltage were observed connecting HVR. These low voltage bridges (LVBs) constituted regions of interest in evaluating critical substrate links within the chamber. Criteria for defining important LVBs were the presence of a low voltage gradient within the LVB, connection to isolated HVRs, and the ability to demonstrate a narrow connection from one region to another.

These LVBs were then targeted for cryogenic ablation using a CryoAblation catheter (Cryocath-Medtronic) for 120 seconds, or radiofrequency ablation using a Safire TX 8 mm catheter (St. Jude Medical) or EPT Blazer 8 mm (Boston Scientific) set at 60 W/60 degrees for 10-20 seconds or until the loss of endocardial voltage was observed from the distal ablation electrode. VGMs were reconstructed following ablation of all LVBs. Ablation endpoint was absence of observable LVB between 2 or more HVR. Because the atrial voltage decreases following ablation, the high and low voltage levels were adjusted lower to assure the absence of LVB connections. Ablation endpoints were defined as termination of AF in patients with PPAF or inducible sustained AF; completion of the substrate guided ablation until there was an absence of LVB including pulmonary vein isolation, and non-inducibility of AF or atrial tachycardia despite aggressive atrial burst pacing.

All patients had routine clinical follow-up including EKGs, holters or event monitors as clinically indicated. Additionally, a 30 day event monitor was obtained 4 months following final ablation, with clinical follow-up including device interrogations, EKGs, and monitoring.

Demographic data and ablation summaries are provided in Table 1:

|  | All | Paroxysmal | Chronic | P value |
|---|---|---|---|---|
| Number | 54 | 28 | 26 |  |
| Age |  | 59.5 | 58.1 | NS |
| M/F |  | 20/9 | 21/5 |  |
| LA Size |  | 44.7 | 45.1 | NS |
| LV EF |  | 59 | 54.8 | NS |
| Number of Lesions |  | 135 | 167 | 0.04 |
| Fluoroscopy Time (minutes) |  | 67 | 91 | 0.007 |
| Total Procedure Time (room entrance to room exit) (minutes) |  | 293 | 318 | NS |

Mapping of the atrium and veins could be performed in SR or in AF, since the VGM is determined by the absolute voltage recorded and is individually adjusted to reveal the connecting low voltage bridges. The high and low voltage levels were recorded at baseline and following completion of targeted LVB ablation. The voltage settings at baseline were significantly different from those obtained during the last VGM in the left atrium when comparing the starting high voltage cut-off between PAF and CAF, 1.4 mV vs. 1.3 mV (p=0.003), but was otherwise not significantly different comparing groups including final high voltage setting (see Table 2). Additionally, the total number of pulses delivered was higher in patients with PPAF compared to patients with PAF: 167 vs. 135 (p=0.04). Fluoroscopy time was also longer for PPAF compared to PAF patients, 91 vs. 67 minutes (p=0.007). This reflects the greater degree of endocardial fragmentation observed in patients with PPAF compared to PAF. Table 2 provides the high and low voltage set points for the first and final voltage maps:

|  | LVLA Base | LVLA Post | HVLA Base | HVLA Post |
|---|---|---|---|---|
| PAF | 0.33 ± 0.18 | 0.17 ± 0.12 | 1.44 ± 0.36 | 0.95 ± 0.47 |
| PPAF | 0.23 ± 0.2 | 0.15 ± 0.08 | 0.99 ± 0.4 | 0.23 ± 0.19 |
| P Value | NS | NS | 0.003 | NS |

|  | LVRA Base | LVRA Post | HVRA Base | HVRA Post |
|---|---|---|---|---|
| PAF | 0.27 ± 0.11 | 0.21 ± 0.14 | 1.3 ± 0.08 | 1.3 ± 0.41 |
| PPAF | 0.23 ± 0.2 | 0.18 ± 0.15 | 1.17 ± 0.35 | 1.2 ± 0.09 |
| P Value | NS | NS | NS | NS |

Figure 18A:
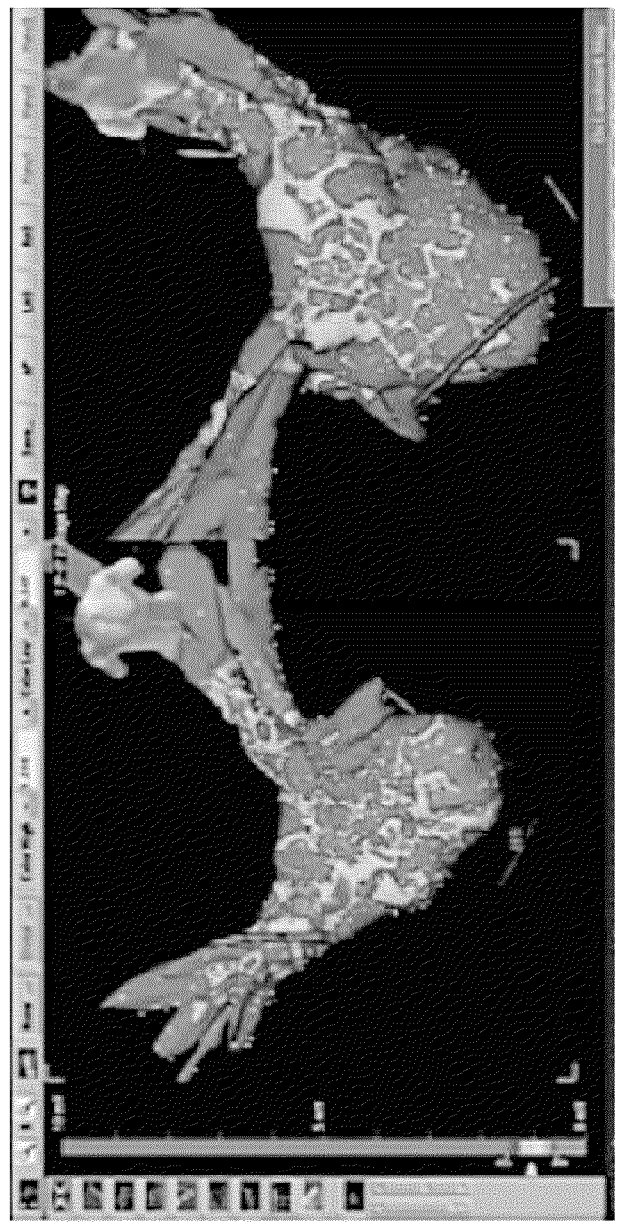
FIG. 18A illustrates example voltage gradient maps created at baseline and following radiofrequency ablation of low voltage bridges for patients with PAF.
Figure 18B:
FIG. 18B illustrates example voltage gradient maps created at baseline and following radiofrequency ablation of low voltage bridges for patients with PPAF.
Figure 18C:
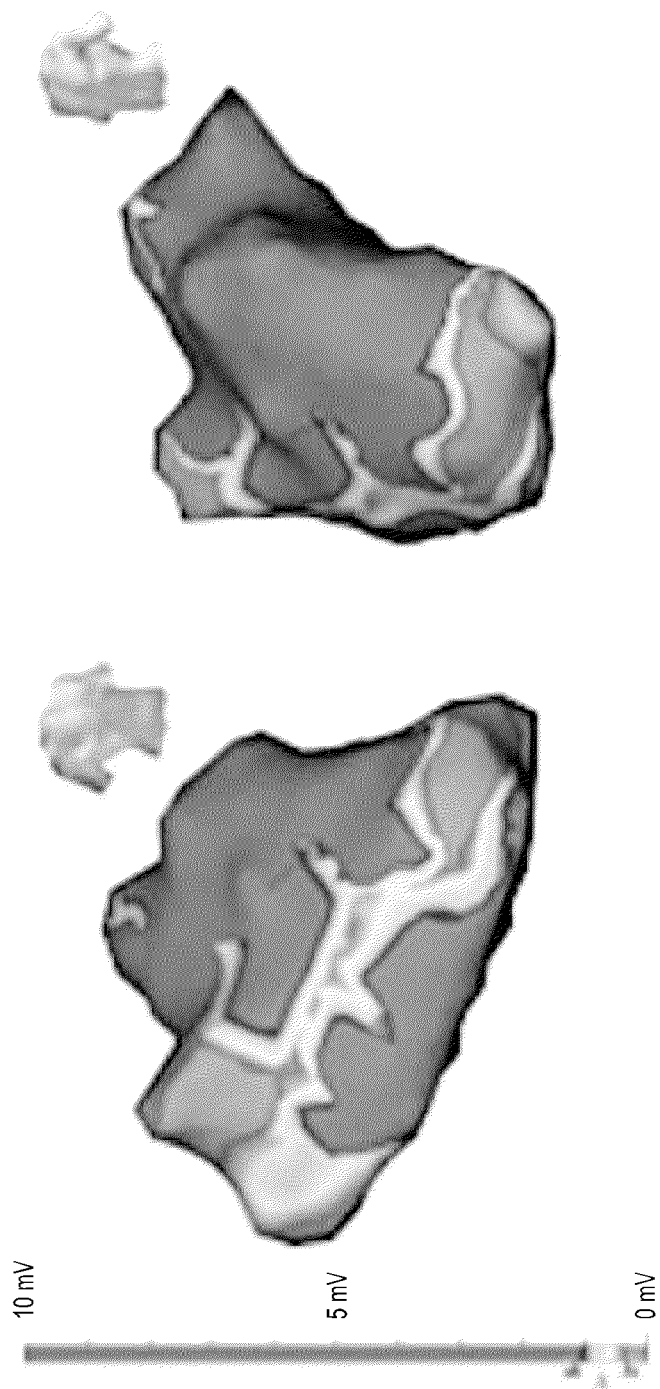
FIG. 18C illustrates example voltage gradient maps for a patient without a history of AF.

Detailed voltage mapping data was obtained in all patients and LVBs were observed in all patients connecting venous structures throughout the atrium, anterior, posterior, septal, lateral walls, and along the left atrial roof, such as the pulmonary veins (PV), coronary sinus (CS), and superior vena cava (SVC). Voltage gradient maps were created at baseline and following radiofrequency ablation of low voltage bridges. Following adequate endocardial voltage sampling, the resulting map was made by adjustment of voltage levels, to permit visualization of low voltage connections linking high voltage regions. FIG. 18A shows a characteristic image of LVB seen in patients with paroxysmal AF. The average number of voltage points collected was 1755 (888-3188) for the left atrium (example shown in FIG. 18A), and 1699 (242-5280) in the right atrium. The position of these bridge connections was not consistent between patients. Total procedure time, measured from the time the patient entered the room to the time the patient exited the room was 305 minutes (180-455), subdivided 293 minutes for PAF and 318 minutes for CAF (NS). The overall voltage is higher and fewer LVB are observed compared to patients with PPAF, as shown in FIG. 18B. Not only are the voltage settings lower in patients with PPAF, the number of LVBs are increased compared to patients with PAF. The progressive substrate changes, which occur in AF, are readily apparent. A young patient without a history of atrial fibrillation, as shown in FIG. 18C, demonstrates coherent and homogenous voltage with few LVB.

Figure 19:
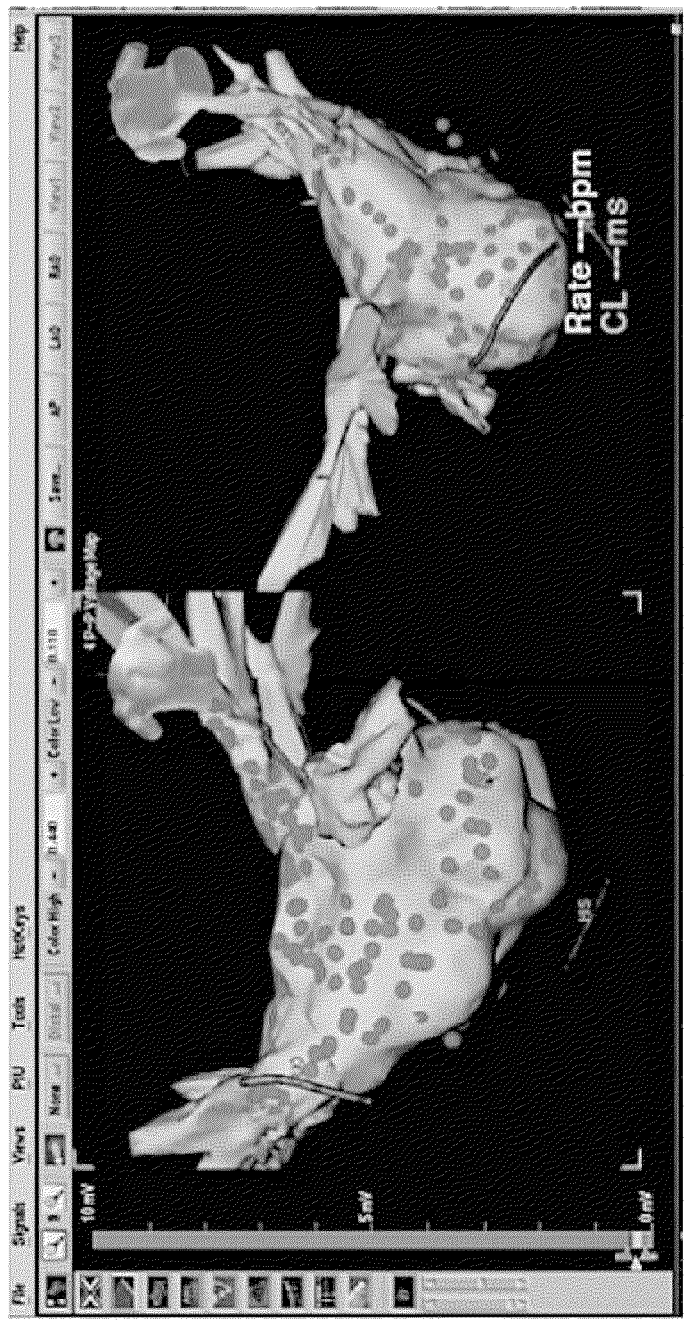
FIG. 19 illustrates example positions of ablations.
Figure 20:
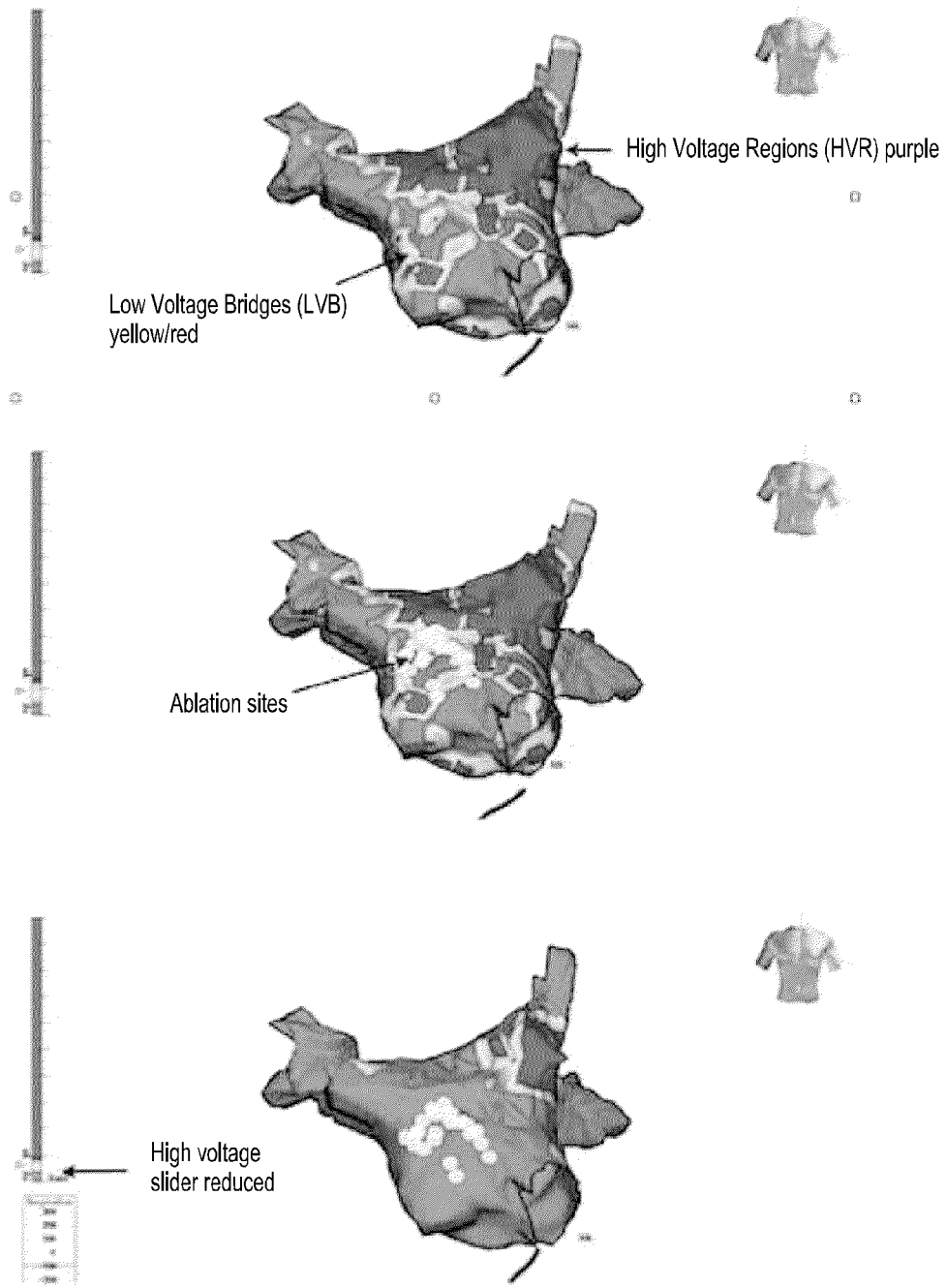
FIG. 20 illustrates changes in the VGM between before and after ablation, and the ablation sites

In all cases, PVs could be isolated outside the vein by finding LVB connecting them to the atrium. These LVB were seen when mapping in SR or in AF. FIG. 19 illustrates example positions of ablations. Radiofrequency energy was delivered to LVBs within the atrium. The position of the LVBs varied greatly between patients, and as a result, no consistent pattern for ablation emerged. Rather ablations were tailored to target regions of abnormal substrate indicated by the presence of LVBs. The lesions were not intended to be transmural nor linear. PPAF patients required more energy applications then patients with PAF. The average lesion time was 18 seconds and non-irrigated radiofrequency energy application was used. However, extensive changes in endocardial voltage were recorded, as shown in FIG. 20. The ablation of LVBs results in dramatic changes in endocardial voltage. As seen in FIG. 20, LVBs are observed along the anterior septum. Ablation targeted to these few LVBs resulted in a significant collapse of voltage on the anterior atrial wall.

The dynamic ratio of voltage was assessed at baseline and following targeted LVB ablation. Of note, the average voltage was significantly decreased for maps obtained following ablation therapy. Ablation of these LVBs resulted in PV isolation, e.g., as shown in FIG. 20. When compared to patients without a history of AF, LVBs were less frequent.

Figure 21:
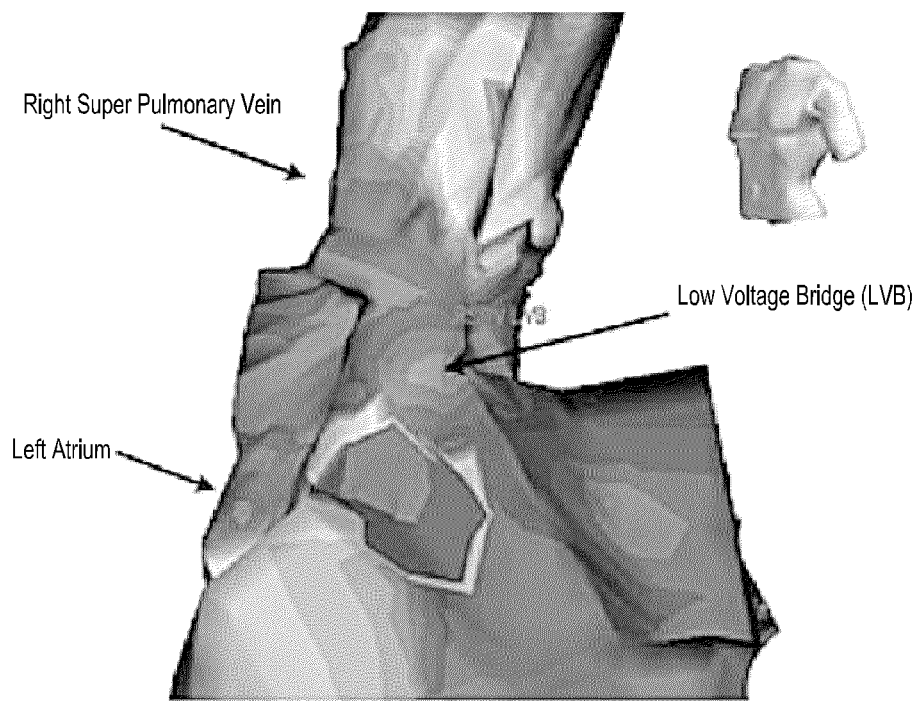
FIG. 21 illustrates example ablation of an LVB connecting the left atrium to the right superior PV.
Figure 21:
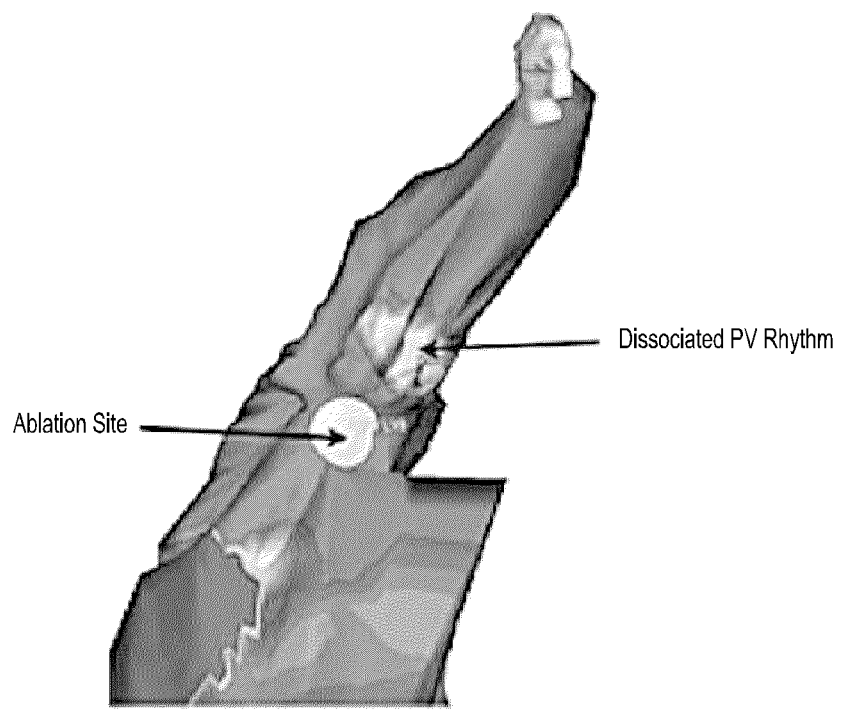

The PVs were successfully isolated in all patients by ablating the LVB connecting the PV to the atrium, e.g., as shown in FIG. 21. Following ablation, the PV is electrically isolated, both antegrade and retrograde. As is noted, an isolated PV potential may sometimes be observed, but without a connecting LVB, it cannot communicate to the left atrium. Isolation does not require circumferential lesions. Isolation was confirmed by repeat contact mapping. In patients where sustained AF was present or induced (n=46), LVB ablation resulted in conversion to sinus rhythm in 43/46 patients (93%). The remaining three patients had termination of AF to an organized atrial tachycardia, which required cardioversion.

AF was not inducible following substrate modification in all patients despite atrial burst pacing from the right atrial appendage and CS, limited by atrial loss of capture (~180 to 160 ms) at high output (10V at 10 mA). If a residual atrial tachycardia was inducible, further mapping and ablation was performed. In two patients with left persistent superior vena cava (LSVC), both AT and AF were inducible until isolation of Coronary Sinus was performed. In these patients, the coronary sinus VGM revealed multiple LVB connections to the right atrium, left atrium, and muscle cuff extending into the left superior vena cava. Atrial tachycardia associated with LSVC has been reported previously in a young patient with atrial tachycardia from the proximal coronary sinus.

The average follow-up time from final procedure was 317 (127-514) days in PAF patients; 359 (174-568) days in PPAF patients. Procedure success was determined by 30 day monitoring at least 4 months following the last procedure. Single procedure success overall was 61% (33/54), with 72% single procedure success for patients with PAF compared to 48% in patients with PPAF. Average number of procedures per patient was 1.1 for PAF and 1.4 for PPAF patients. Following a second procedure, the overall success rate was 78% (42/54) with PAF patients having success 86% vs. 68% for PPAF patients (see Table 2).

The primary endpoint was absence of recurrent AF. Recurrent PPAF was observed in 4/54 (7%) of all patients in the study, and was observed only in patients with PPAF. PAF was observed in 11% of patients with PAF and PPAF. 12% of PPAF patients converted to PAF during follow-up.

The secondary endpoint was arrhythmia free. Atrial tachycardia was seen transiently within the first month following ablation in both patients with PAF and PPAF, but was persistent in 10 patients. Atrial tachycardia was observed in both patient populations (PPAF 5; PAF 5). Thus, 10/54 patients had persistent atrial tachycardia following a single procedure (19%) and only 2/54 (4%) following a second procedure.

Prior to ablation, patients were treated with an average of 1.6 anti-arrhythmic drugs. Post ablation the average number of drugs per patient was 0.4. Treatment was continued because of frequent premature beats or non-sustained rhythms.

Post ablation atrial tachycardia had a cycle length of between 230 and 320 ms. The majority had an upright P wave in V1 and the inferior leads and represented macro-circuits around the mitral valve or septum. Repeat VGM and entrainment mapping confirmed this mechanism. Overall, successful termination of the recurrent AT was achieved in 8/10 (80%) patients (1 patient is scheduled for second procedure).

The impact of atrial fibrillation ablation upon p wave duration has been previously reported. Most studies demonstrated that p wave duration is shorter post ablation than baseline. There was a significant decrease in P wave duration in patients with PAF 134.5±20.3 ms pre-ablation to 113.3±26.4 ms post-ablation (p=0.03). Following ablation and conversion to sinus rhythm, PPAF patients had an average P wave duration of 118. This finding may be explained by elimination of regions of endocardial slow conduction (LVB) and elimination of endocardial fragmentation.

Figure 22:
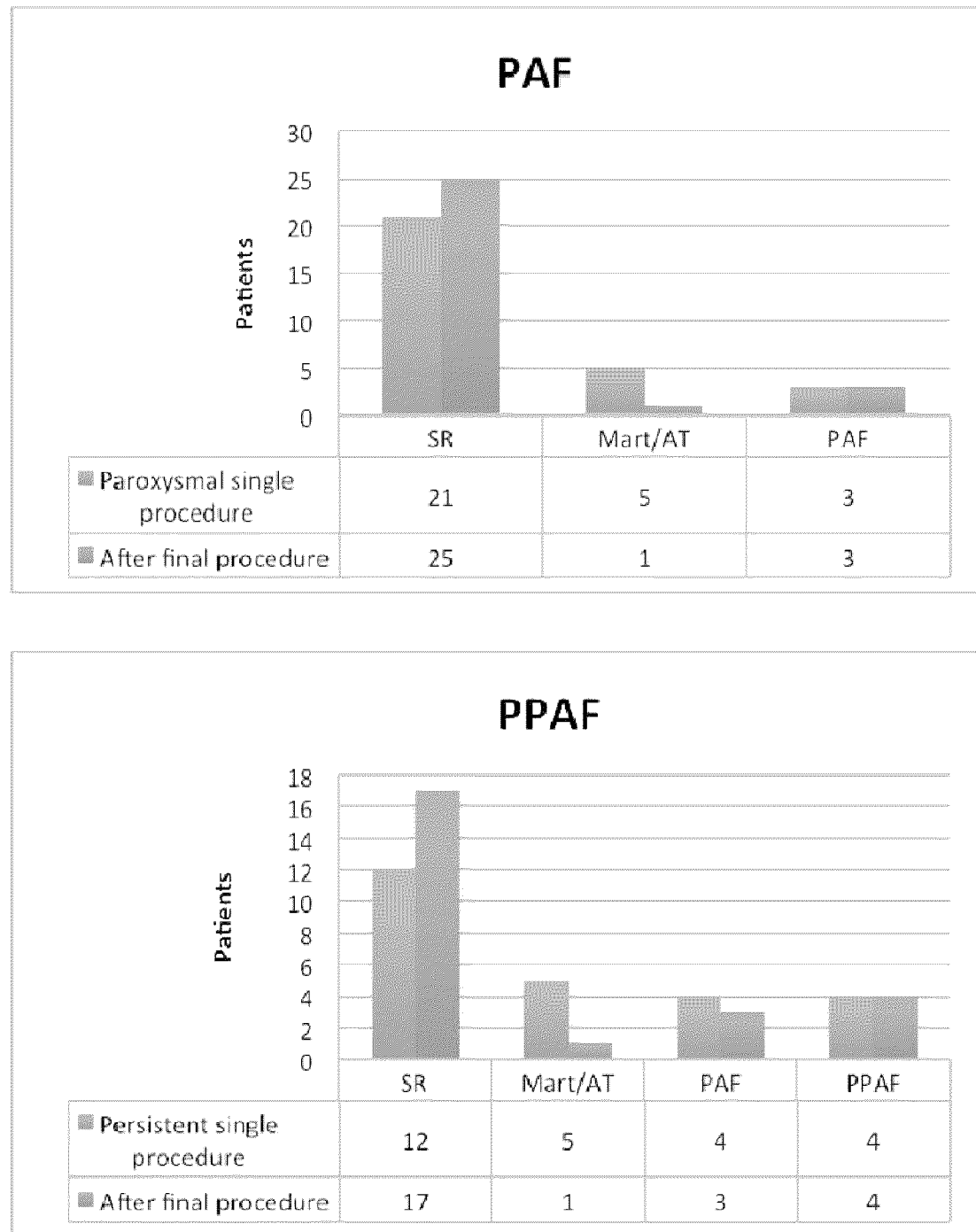
FIG. 22 illustrates a summary of the single procedure outcomes associated with substrate based AF ablation guided by VGM.

Complications were uncommon in these patients. Two patients had tamponade (3%). Pleuretic chest pain requiring extended non-steroidal anti-inflammatory therapy was observed in 5 patients (7.5%). A summary of the single procedure outcomes associated with substrate based AF ablation guided by VGM is shown in FIG. 22, which summarizes the outcome data in the 54 patients followed in this study. The single procedure and second procedure outcomes are displayed. Patients with PAF tended to have better single procedure success than patients with PPAF; however, both groups benefited from repeat ablation if used. Of note, in the PPAF group, the conversion to PAF was observed in 3 patients who had rare episodes that were >30 seconds. Macro reentry AT was the usual recurrent arrhythmia rather than AF.

Figure 24A:
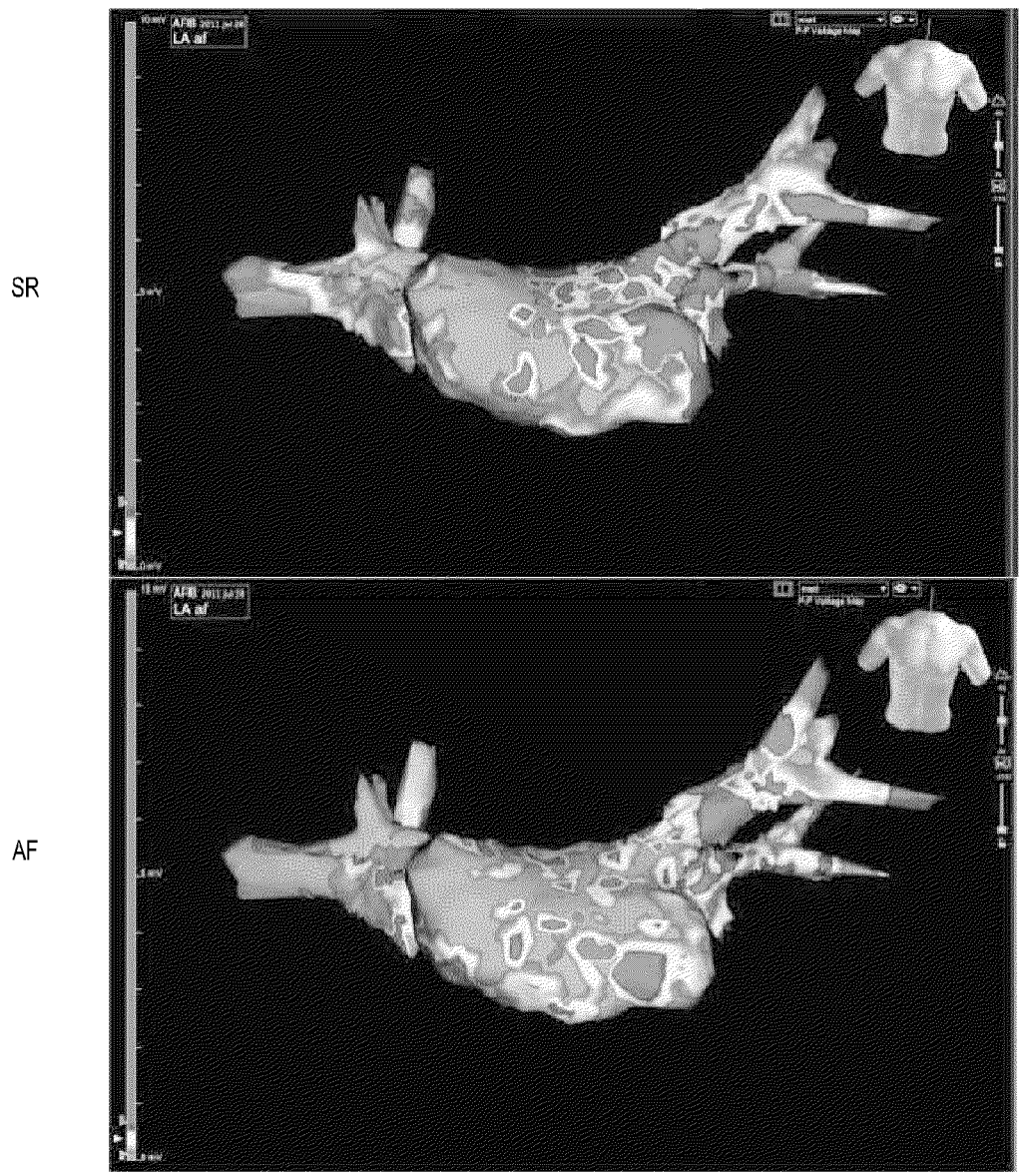
FIG. 24A illustrates voltage gradient maps created in sinus rhythm and atrial fibrillation for the same patient.
Figure 24B:
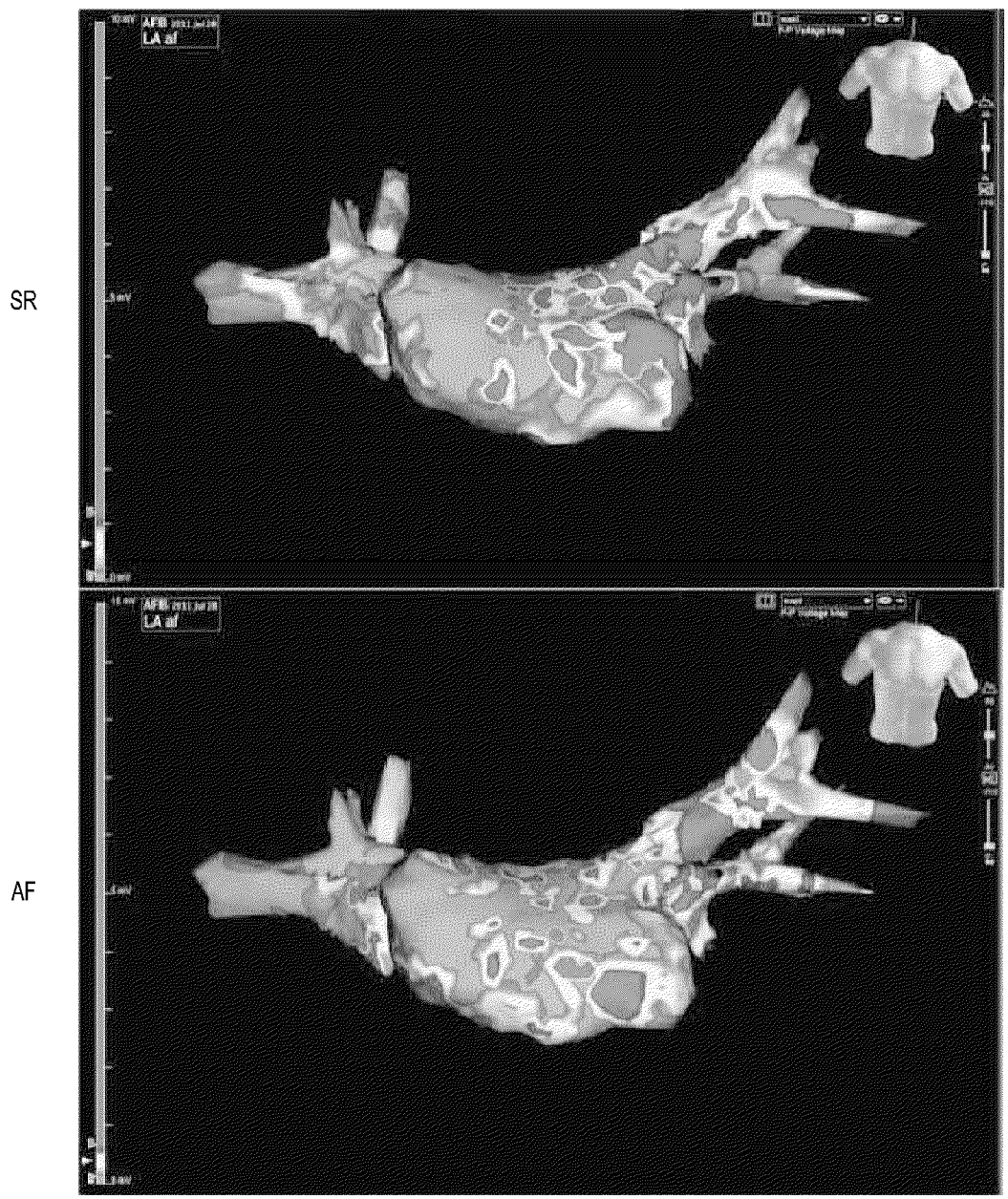
FIG. 24B illustrates the voltage gradient maps of FIG. 24A, with low voltage areas converted to white, while high voltage regions converted to black.

This study provided the following evidence that atrial endocardial substrate is visualized by VGM. First, as noted above, MRI determined fibrosis is increased in patients with PPAF compared to patients with PAF. VGM demonstrates similar changes such as a significant decrease in high voltage level settings and greater endocardial fragmentation with predominance of LVBs, in patients with PPAF vs. PAF (see FIG. 18A-18C). Second, if VGM represents an accurate depiction of endocardial substrate, then the resulting voltage map should be similar whether it is obtained in sinus rhythm or during AF. While the absolute voltage will be different, the relative voltage and resultant gradient map should reflect the same substrate variations. FIGS. 24A and 24B demonstrate VGM obtained in sinus rhythm and in AF from the same patient. In FIG. 24A, the overall voltage was adjusted demonstrating lower voltage observed during AF. Low voltage bridges are observed in similar locations regardless of the underlying rhythm. In FIG. 24B, low voltage areas are converted to white, while high voltage regions are black. In this example, lines are placed through low voltage bridges observed in the voltage gradient map created in sinus rhythm. These lines are then superimposed over the voltage gradient map obtained in AF. As can be seen, both recordings demonstrate similar ablation strategies based on targeting low voltage bridges, despite being obtained during different rhythms. The underlying substrate remains remarkably similar.

This study provided the following evidence that low voltage bridges are important endocardial connections:

1. Low Voltage Bridges are Markers for Selective Activation Inputs to Venous Structures, Such as the Pulmonary Veins and SVC:

Identification and selective ablation of low voltage connections resulted in electrical isolation of the venous structures (see FIG. 21). Therefore, focal inputs can be targeted without requiring circumferential ablation.

2. Low Voltage Bridges Activate Atrial Endocardium Selectively and Ablation of the Bridge Results in a Regional Loss of Voltage within the Atrium:

A disproportionally large area of atrial voltage was lost when the low voltage bridge serving that region was ablated, suggesting that atrial endocardial activation is not homogenous and multi-directional. Rather, endocardial activation is regional with inputs, dependent upon only a few endocardial low voltage connections. Despite short duration of radiofrequency pulses, typically 10 to 15 seconds, ablation of the low voltage bridge resulted in a collapse of atrial voltage distal to the lesion (see FIG. 20).

3. Ablation of the Low Voltage Bridge Creates an Irreversible Endocardial Voltage Drop and Leads to Permanent Regional Isolation:

The persistence of endocardial voltage change was observed in twelve patients restudied 6 to 12 months following the initial ablation. Reestablishment of endocardial activation does not appear to be common following LVB ablation.

Figure 23:
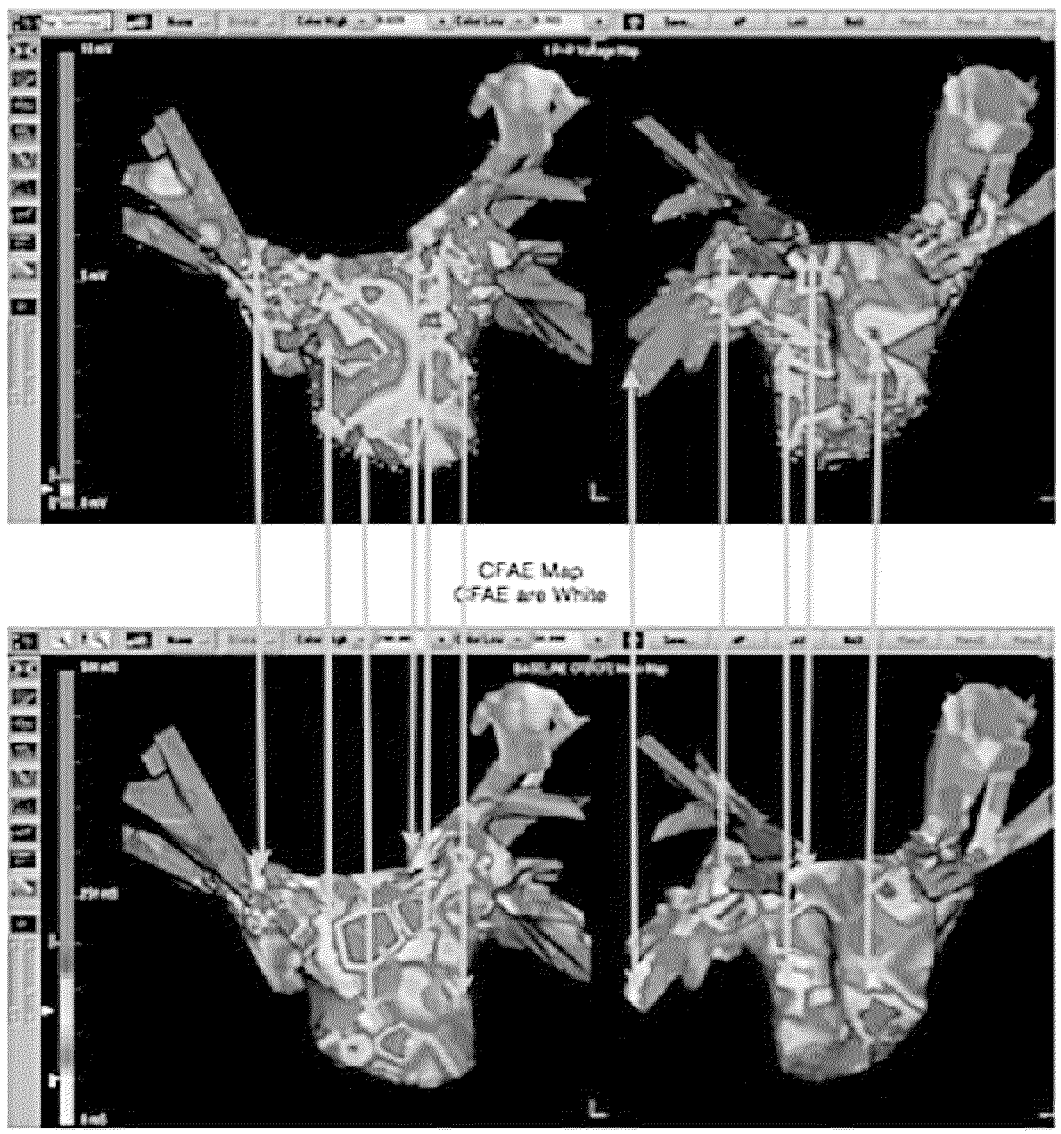
FIG. 23 illustrates CFAE sites associated with high voltage regions, rather than LVBs.

4. High Frequency Chaotic Regions (CAFÉ) are Located in High Voltage Regions. Ablation of the Associated Low Voltage Bridges Results in Loss of the CAFÉ without Direct Ablation of the CAFÉ:

Ablation of the associated low voltage bridge is associated with ablation of the CAFÉ. It is likely that these low voltage bridges serve as a conduit from high voltage regions containing the high frequency and fractionated activation. These structures then interact as an atrial syncytium propagating the fibrillatory waves within the atrium. The relationship between HVRs/CFAEs and LVBs is depicted in FIG. 23. Roberts-Thompson, et al., reported that CFAEs increase with age and are associated with regions of low voltage and slowed conduction ("Fractionated atrial electrograms during sinus rhythm: Relationship to age, voltage, and conduction velocity," Heart Rhythm 2009; 6:587-591). It has also been noted that patients with persistent AF have more CFAEs compared to PAF patients (Solheim et al., "Characteristics and distribution of complex fractionated atrial electrograms in patients with paroxysmal and persistent atrial fibrillation," J. Interv. Card. Electrophysiol. 2010, 28:87-93).

5. The Development of Low Voltage Bridges is Associated with Progression of the Atrial Disease:

Normal atria without atrial fibrillation consist of generally uniform atrial voltage with few low voltage bridges. While they can be observed near the venous structures, they are not a prominent feature. As atrial fibrillation progresses from the paroxysmal to chronic forms, the development of endocardial voltage fractionation becomes apparent. Larger numbers of low voltage bridges are created. The development of low voltage bridges correlates to the severity of clinical disease and is a marker for substrate changes within the atrial endocardium (see FIGS. 18A-18C).

6. Termination of Atrial Fibrillation and Inability to Induce Tachycardia was Associated with the Absence of Low Voltage Bridges:

In patients presenting or with inducible sustained atrial fibrillation, conversion to sinus rhythm was successful in 43/46 (93%) of patients with ablation alone. Repeat voltage gradient mapping confirmed absence of further low voltage bridges (see FIG. 20). Burst pacing in the atrium following successful substrate modification failed to re-initiate atrial fibrillation. When an AT was induced, a residual atrial circuit was observed during repeat mapping and was subsequently ablated.

In follow-up, only one patient presented with recurrent atrial fibrillation (1/66 or 1.5%). Eight patients presented with persistent atrial tachycardia (8/66 or 12%) with a cycle length of 230 to 320 ms (see FIG. 21). Two p wave morphologies were observed in these recurrent atrial tachycardias: upright inferior and anterior precordial leads (7), and negative inferior and upright in the anterior precordial leads (1). Of these 8 patients, 2 patients remained asymptomatic with rate control and declined further intervention. Three other patients had repeat studies that demonstrated residual low voltage bridges involving the posterior septum by the right inferior pulmonary vein and posteroseptal mitral valve; persistent low voltage bridge between the left atrial appendage and left superior pulmonary vein, or LAA and anterior mitral valve. These atrial tachycardias represent macro-circuits around the mitral valve or vein of Marshall. The negative p wave tachycardia was terminated within a branch of the great cardiac vein. The remaining 5 patients were observed during the 1 month blanking period, 2 spontaneously resolved; the remaining 3 were awaiting evaluation following the 2 month visit.

In patients with inducible atrial tachycardia post ablation, anti-tachycardia pacing was successful for tachycardia conversion, suggesting that in such cases, consideration for implantation of a pacemaker with anti-tachycardia programmability may be an alternative to drug therapy or repeat ablation. Complications were uncommon in these patients. X tamponade was observed.

In certain embodiments, accurate data collection is advantageous to achieve valid voltage gradient maps. Unfortunately, such accurate data collection can involve a point by point assessment of the endocardial recording (e.g., 800 or more points per map), with these data points excluding electrical noise or inadvertent ventricular recordings. Such invalid data skews the voltage map, rendering it less reliable. It is particularly important to evaluate the data points when assessing low voltage bridges. Additionally, remapping with subsequent adjustment of the voltage values is advantageous to exclude residual low voltage connections. This was observed upon restudy of patients with inducible atrial tachycardia following the initial LVB ablation. Therefore, in certain embodiments, the voltage settings are decreased following each ablation session during the remap. Despite this effect, residual atrial circuits are observed around the mitral valve or atrial septum and a second ablation targeting of these sites was used.

It is reasonable that some patients will have refractory tachycardia despite successful substrate modification. Epicardial circuits are not assessed in certain embodiments described herein, while in certain other embodiments, epicardial circuits are assessed.

As discussed above, current approaches to ablation of atrial fibrillation have had moderate success for paroxysmal forms of atrial fibrillation and modest success for persistent or chronic forms. Single procedure success varies greatly in the literature. A meta-analysis of Calkins et al. found the single procedure success was 57% and with multiple procedures the success increases to 71% ("Treatment of Atrial Fibrillation With Antiarrhythmic Drugs or Radiofrequency Ablation: Two Systematic Literature Reviews and Meta-Analyses," Circ. Arrhythm. Electrophysiol, 2009 (2,3) pp. 49-361). In patients with persistent or permanent AF, the single procedure results range from 40 to 50% (see, e.g., Cheema et al., "Long-term single procedure efficacy of catheter ablation of atrial fibrillation," J. Interv. Card. Electrophysiol., 2006, 15:145-155; Cheema et al., "Long-Term Safety and Efficacy of Circumferential Ablation with Pulmonary Vein Isolation," J. Cardiovasc. Electrophysiol., Vol. 17, pp. 1080-1085, October 2006).

Ablation based upon anatomic approaches to isolate atrial segments has become the standard for therapy. The underlying rationale is that these segments contain automatic atrial foci that trigger atrial fibrillation. Whether the isolation is achieved by open surgery or via catheter based systems, the primary goal is the isolation of the pulmonary veins. Successful isolation, therefore, prevents triggering events from initiating atrial fibrillation.

However, isolation of pulmonary vein segments is likely insufficient in 20-30% of patients with paroxysmal and a majority of patients with persistent or chronic forms of atrial fibrillation. Indeed, Miyazaki, et al., reported that 87% of late recurrences of AF are from non-PV triggers ("Long-term clinical outcome of extensive pulmonary vein isolation-based catheter ablation therapy in patients with paroxysmal and persistent atrial fibrillation," Heart, published online Aug. 18, 2010). As a result, in order to improve outcomes, many centers place empiric ablation lines on the atrial roof or along the mitral annulus (Gaita et al., "Long-Term Clinical Results of 2 Different Ablation Strategies in Patients With Paroxysmal and Persistent Atrial Fibrillation," Circ. Arrhythm. Electrophysiol., 2008; 1; 269-275), or include mapping of high frequency foci. Whether circumferential PV isolation, antral PV isolation, or combined with CFAE mapping, single procedure success remains uncertain. Biase, et al., found no benefit from antral isolation vs. antral isolation followed by CFAE ablation in patients with PAF ("Atrial fibrillation ablation strategies for paroxysmal patients: Randomized comparison between different techniques," Circ. Arrhythmia Electrophysiol., 2009; 2:113-119). H Oral et al. reported no benefit of CFAE ablation following antral PV isolation in patients with chronic or persistent AF ("Randomized Assessment of the Incremental Role of Ablation of Complex Fractionated Atrial Electrograms After Antral Pulmonary Vein Isolation for Long-Lasting Persistent Atrial Fibrillation," J. Am. Coll. Cardiol., 2009; 53:782-9). Others have reported improved outcomes when a combination of antral isolation and CFAE ablation was performed in patients with persistent or chronic AF (40 vs. 61%) (Callans D, "Comparison of different ablation strategies for persistent atrial fibrillation: Beyond casual observations," Heart Rhythm, Vol. 5, No 12, December 2008). Still others have targeted the left atrial ganglionated plexi in addition to antral isolation in PAF, or circumferential isolation in chronic or persistent AF, with varying results (80% single vs. 60% multiple procedures) (Lin et al. "Efficacy of Additional Ablation of Complex Fractionated Atrial Electrograms for Catheter Ablation of Nonparoxysmal Atrial Fibrillation," J. Cardiovasc. Electrophysiol., Vol. 20, pp. 607-615).

For such patients, empiric ablation lines are placed on the atrial roof or along the mitral annulus, or mapping of high frequency foci is performed. Still, these methods do not define the underlying substrate for atrial fibrillation propagation, nor do they offer a uniform approach to treatment of AF regardless of whether it is paroxysmal or long-standing. Thus, the mechanisms for atrial fibrillation propagation and the reasons for both success and failure remain uncertain. Progress for improved outcomes in treatment of atrial fibrillation depends upon developing a strategy for ablation that is based upon the underlying substrate necessary for sustaining atrial fibrillation.

Histologic evaluation of atrial tissue in patients with AF has demonstrated progressive structural changes that occur with aging as well as in association with the presence of AF. These changes include fibrosis (see, e.g., Nguyen et al., "Histopathological Substrate For Chronic Atrial Fibrillation in Humans." Heart Rhythm, 2009 April; 6 (4): 454-460; Pellman et al., "Extracellular matrix remodeling in atrial fibrosis: Mechanisma and implications in atrial fibrillation," Journal of Molecular and Cellular Cardiology 48 (2010) 461-467; Pan et al., "Unique Histological Features of the Left Atrial Posterior Wall," Journal of International Medical Research 2009; 37: 392-399) and loss of myocyte gap junction connections (see, e.g., Laurent et al., "Effects of Chronic Gap Junction Conduction Enhancing Antiarrhythmic Peptide GAP-134 Administration on Experimental Atrial Fibrillation in Dogs," Circ. Arrhythm. Electrophysiol. 2009; 2; 171-178). The latter has also been reported as a genetic mutation in lone AF (Thibodeau et al., "Paradigm of Genetic Mosaicism and Lone Atrial Fibrillation Physiological Characterization of a Connexin 43—Deletion Mutant Identified From Atrial Tissue," Circulation, 2010; 122:236-244). Indeed, Lui, et al., reported that decreased Connexin 43 was associated with fibrosis and the presence of atrial CFAE sites ("Decreased Connexin 43 and Increased Fibrosis in Atrial Regions Susceptible to Complex Fractionated Atrial Electrograms," Cardiology 2009; 114:22-29). It is clear: AF is not just a disease of unfortunately timed premature beats, but instead, represents a constellation of structural changes within the atrial myocardium. Therefore, one can postulate that the atrial substrate should demonstrate progressive changes as the disease state progresses. Recent MRI data from patients with PAF and PPAF demonstrate progressive fibrosis that correlates with ablation outcomes (Daccarett et al., "MRI of the left atrium: predicting clinical outcomes in patients with atrial fibrillation," Expert Rev. Cardiovasc. Ther., 2011 January; 9 (1): 105-11). The initiation, propagation, and maintenance of AF depends upon regions containing both normal and abnormal tissue. We postulate that the progression of histological changes parallel progressive endocardial fragmentation and the development of greater numbers of LVB that have been observed in this study. Patients without AF have few LVBs, while patients with AF demonstrate progressively both lower atrial voltages, a greater number of LVBs with resultant endocardial fragmentation that correlates to the severity and chronicity of the AF.

Global measurements of atrial voltage and conduction velocity have been found to be reduced in both PAF and long-lasting AF (Park et al., "The Relationship Between Endocardial Voltage and Regional Volume in Electroanatomical Remodeled Left Atria in Patients with Atrial Fibrillation: Comparison of Three-Dimensional Computed Tomographic Images and Voltage Mapping," J. Cardiovasc. Electrophysiol, Vol. 20, pp. 1349-1356, December 2009; Chang et al., "Biatrial Substrate Properties in Patients with Atrial Fibrillation," J. Cardiovasc. Electrophysiol., Vol. 18, pp. 1134-1139, November 2007). By mapping regional voltage variations, normal tissue may be seen as HVR, while LVRs are consistent with diseased tissue. Electrograms from LVBs frequently demonstrate complex morphologies and have slower conduction velocities than the surrounding HVR. The nature of the interactions between normal and diseased tissues offers insight into the mechanisms for AF propagation.

A relationship exists between the presence of CFAE and HVRs that have electroanatomic connections with associated LVBs, as shown in FIG. 23. As demonstrated, certain regions correlated well with the CFAE mapped simultaneously in patients with sustained AF (PPAF or induced AF). In patients with AF, regions of diseased tissue interdigitate with normal tissue. By mapping regional voltage variations, normal tissue may be seen as HVR, while LVRs are consistent with diseased tissue. The nature of these interactions between normal and diseased tissues offers insight into the mechanisms for AF propagation. The syncytium of tissue creates a wavelet reservoir and by disruption of the LVB connections, the wavelet propagation is terminated. The present study tested the hypothesis that ablation of the LVB connections, disrupts wavelet propagation, terminates AF acutely, and provides improved outcomes in patients with both PAF and PPAF.

In the absence of substrate based ablation, long term success in PAF patients treated with PV isolation alone, or with various combinations of adjuvant therapy may be in doubt. Indeed, in recently published data, Weerasooriya et al. reported the single procedure success in patient with AF decreases significantly over time, from 40% at 1 year to 29% at 5 years, with most of the recurrences appearing within the first 6 months ("Catheter ablation for atrial fibrillation: are results maintained at 5 years of follow-up?" J. Am. Coll. Cardiol. 2011 Jan. 11; 57 (2):160-6). Short-term success may represent interruption of sufficient LVBs by isolation of PVs in patients with minimal fragmentation. Because the disease process continues over time, diffuse and progressive atrial endocardial fragmentation of residual HVRs occurs with subsequent AF recurrence. Therefore long-term success may be facilitated by substrate mapping in all patients with AF, whether PAF or PPAF. In our patients, the initial success has been stable with longest follow-up to 568 days.

Interestingly, PVs act as such a structure and because PV isolation is most successful in patients with PAF, who may have less disease burden, and possibly less LVB burden. It is also likely, AF ablation failures, whether in patients with PAF or chronic forms, may be attributable to inadequate LVB ablation that occurs with WAKA and limited surgical MAZE procedures. Further studies will be informative in this regard.

Selective targeting of LVBs offers distinct advantages over traditional AF ablation approaches. First, by targeting substrate, healthy tissue can be avoided. Second, because lower energies can be used for shorter time periods, since transmural lesions are not required, collateral tissue damage is minimized. Third, termination of sustained AF is commonly observed during LVB ablation (91%), but is less frequently seen using other techniques (53% with PV isolation+linear ablation, +CFAE ablation) (Rostock et al., "Chronic Atrial Fibrillation Is a Biatrial Arrhythmia: Data from Catheter Ablation of Chronic Atrial Fibrillation Aiming Arrhythmia Termination Using a Sequential Ablation Approach," Circ. Arrhythm. Electrophysiol. 2008; 1; 344-353). Both termination of AF and non-inducibility of AF have been reported to have better long-term outcomes (Li et al., "Predictive Value of Early Recurrence and Delayed Cure After Catheter Ablation for Patients With Chronic Atrial Fibrillation," Circ. J. 2008; 72: 1125-1129). Substrate mapping with LVB ablation achieved both of these favorable outcome predictors. Finally, the methodology provides a means to assess the underlying atrial substrate such that elimination of LVBs creates a defined and measurable endpoint for AF ablation.

It may be argued that these LVB do not represent atrial substrate; however, this construct for substrate analysis creates several testable hypotheses. If the LVB represent diseased atrium, then patients without a history of AF should have less LVB than patients with AF. Further, the number of LVBs should correlate to the severity and chronicity of AF. Ablation of LVB commonly terminates AF, suggesting that these structures are important in the propagation and maintenance of AF. Clinical studies regarding patient's outcomes will be informative in illustrating the utility of this method. Finally, this finding has implications for long term success in PAF patients treated with PV isolation/WAKA. If atrial disease is a progressive process in AF, then HVR in patients with little AF burden may fractionate over time, creating new LVR and LVBs. Ironically, long term success may be better in patients with more advanced, and hence, larger number of atrial LVBs.

In certain embodiments, voltage gradient mapping, which evaluates dynamic voltage changes within the atria, can be used to directly assess the underlying atrial substrate. Variations in atrial voltage can be observed in normal atria, however, as patients exhibit atrial fibrillation, these voltage variations become more frequent and diffuse and patients with atrial fibrillation exhibit progressive fragmentation of the endocardial voltage that correlate to the chronicity of atrial fibrillation. It has been previously reported that patients with atrial fibrillation have lower atrial voltages than patients without atrial fibrillation (Fiala et al., "Left Atrial Voltage during Atrial Fibrillation in Paroxysmal and Persistent Atrial Fibrillation Patients," PACE 2010; 541-548). These studies did not evaluate local voltages, but rather average voltages. By creating 3D electroanatomic maps in certain embodiments described herein, the regional differences can be defined and can provide localization of the regional variations of atrial voltage. In certain embodiments, using voltage gradient mapping can define the precise connections between high voltage areas and low voltage areas can become clear.

These connections are low voltage bridges, the number of which increase proportionally with the severity of the atrial fibrillation. They are the electrical equivalent of the increase in scaring and fibrosis observed histologically and associated with the presence of atrial fibrillation. Functionally, these low voltage bridges are characterized by slow conduction and wide and complicated potentials compared to recordings from normal voltage areas. For this reason, they may act as functional reservoirs for wavelet propagation. Indeed, they are observed connecting CFE foci which are found in regions of high voltage. Thus, CFE sites may integrate multiple low voltage bridge connections. It is important to note, that previous studies have shown selective ablation of CFE sites are not sufficient to terminate or prevent recurrent atrial fibrillation, although they may improve outcomes when associated with standard pulmonary vein isolation.

Because this method does not require contiguous linear transmural lesion creation, it has several advantages over standard approaches. Because targeting of low voltage bridges does not require contiguous lesions for success, skip lesions and resultant micro reentry tachycardias are avoided. Iatrogenic atrial tachycardias have been well described in the literature (Ning et al., "Mechanisms of organized atrial tachycardia during catheter ablation of chronic atrial fibrillation by stepwise approach," Chin. Med. J., 2010; 123 (7):852-856) and are typically related to breaks in the lines of block created with antral lines. Daubert reviewed iatrogenic left atrial tachycardias providing insight into the EKG findings ("Iatrogenic Left Atrial Tachycardias: Where Are We?" J. Am. Coll. Cardiol. 2007; 50; 1788-1790). These atrial tachycardias may be difficult to map and represent up to 50% of recurrent tachycardias seen following linear ablation procedures (Lim et al., "Atrial Arrhythmias After Single-Ring Isolation of the Posterior Left Atrium and Pulmonary Veins for Atrial Fibrillation: Mechanisms and Management," Circ. Arrhythm. Electrophysiol. 2008; 1; 120-126). Additionally, linear lesion sets have lead to complications such as left atrial isolation (Ning et al., "Left atrium electrical isolation as a complication of catheter ablation of persistent atrial fibrillation," Acta Cardiol. 2010; 65 (2): 271-273), and may not offer significant clinical benefit (Mikhaylov et al., "Additional left atrial septal line does not improve outcome of patients undergoing ablation for long-standing persistent atrial fibrillation," Acta Cardiol. 2010; 65 (2): 153-160). In contrast, in certain embodiments described herein, atrial tachycardia associated with substrate-based ablation is a macro-reentry circuit around the Mitral Valve and septum. As a result, the mapping of these residual atrial circuits is greatly simplified.

By applying a consistent methodology to the mapping and ablation of atrial fibrillation, in certain embodiments, both paroxysmal and chronic atrial fibrillation can be viewed as a continuum of the same process of scaring and electronic myocyte delinking, rather than distinct clinical entities. Voltage gradient mapping in certain embodiments permits direct visualization of the progressive electrical endocardial fragmentation that creates the substrate for atrial fibrillation propagation and maintenance. Meaningful outcomes use individualization of therapy based upon the underlying substrate, and documentation of successful modification of the atrial endocardium.

In this example study, targeting low voltage bridges resulted in ablation of the CFE site. The finding that selective ablation of low voltage bridges results in a loss of voltage and electrical activation in regions remote from the actual ablation site is remarkable. The implication of this finding suggests that endocardial atrial tissue is not electrically homogenous, but rather, composed of regional segments that are uniquely activated. Thus ablation of the low voltage bridge collapses the endocardial voltage of the region it serves. In this example study, patients undergoing atrial fibrillation ablation had electroanatomic voltage mapping performed within the left and right atrium, including the pulmonary veins, superior vena cava, and inferior vena cava. Ablation of low voltage bridges to the pulmonary veins, superior vena cava, and regions within the atria proper, resulted in successful isolation of the tissue without requiring circumferential lesions. In fact, these endocardial connections do not require excessive energy for successful ablation. The low voltage bridges can be successfully ablated without using RF delivered by irrigated catheters or prolonged energy application times.

Several conclusions are suggested by these findings. The critical atrial substrate being mapped represents an endocardial tissue connection that acts as interconnected atrial syncytium. Also, these endocardial connections are extremely sensitive to disruption and do not require transmural energies. In addition, endocardial isolation results in inability to maintain and propagate atrial fibrillation, as evidenced by the success at AF termination in patients with chronic AF (75%), in the ability to induce sustained AF at the end of the study, and in the remarkable absence of AF during clinical follow-up.

Because certain embodiments of this method do not use or require contiguous transmural lesion creation, it has several advantages over standard approaches. Such embodiments advantageously permit the application of lower RF energies and therefore collateral tissue damage is minimized. Additionally, the shorter lesion times of certain embodiments advantageously decrease the likelihood of char formation at the ablation catheter tip. Because targeting of low voltage bridges does not require contiguous lesions for success, skip lesions and resultant micro atrial reentry tachycardias are advantageously avoided in certain embodiments. Unfortunately, residual bridges or epicardial circuits may present with arrhythmia recurrence in these patients, so rate control, repeat mapping and ablation, or consideration for anti-tachycardia pacing should be considered during clinical follow-up.

While 12% of the patients had persistent atrial tachycardia, unlike atrial arrhythmias associated with standard WAKA procedures, these residual arryhytmias appear to be macro-rentry and are related to anatomic substrate, rather than an artifact of the ablation procedure itself. As a result, the mapping of these atrial tachycardias is greatly simplified, and when used, ablation has been successful. Because of the consistency observed in the mechanism of post ablation atrial tachycardia, additional energy at these sites in certain embodiments may prevent occurrence of these tachycardias in follow-up.

By applying a consistent methodology to the mapping and ablation of atrial fibrillation in certain embodiments, both paroxysmal and chronic atrial fibrillation can be viewed as a continuum of the same process of scaring and electronic myocyte delinking, rather than distinct clinical entities. Voltage gradient mapping in certain embodiments permits direct visualization of the progressive electrical endocardial fractionation that creates the atrial substrate for atrial fibrillation propagation and maintenance. Meaningful outcomes advantageously utilize individualization of therapy based upon the underlying substrate, and documentation of successful modification of the atrial endocardium.

In certain embodiments described herein, VGM can be a successful method to evaluate critical structures within the atrial substrate of patients with AF. Use of VGM can enable further study of the underlying mechanisms of atrial fibrillation and offer greater opportunities to modify the atrial substrate. By targeting low voltage bridges, the atrial endocardium is significantly modified in certain embodiments, such that the mechanism of propagation and maintenance of AF fatally interrupted. Atrial substrate mapping through the technique of voltage gradient mapping in certain embodiments offers a rational method to approach atrial fibrillation ablation regardless of the clinical severity of AF. By unifying the atrial histopathology with endocardial variations observed within the atrium, patients receive tailored therapy designed to improve success in PAF and PPAF as well as decrease future recurrences by prevention of further endocardial fragmentation as the disease progresses. It addresses the desire to tailor therapy for each patient, and offers the ability to define an objective clinical end-point. In contrast to current anatomic driven methods, VGM can be used to explain both success and failure of present approaches to AF ablation. Use of VGM should enable further study of the underlying mechanisms of atrial fibrillation and offer greater opportunities to provide patients improved therapeutic outcomes.

Various embodiments of the present invention have been described herein. Although this invention has been described with reference to these specific embodiments, the descriptions are intended to be illustrative of the invention and are not intended to be limiting. Various modifications and applications may occur to those skilled in the art without departing from the true spirit and scope of the invention.

What is claimed is:

1. A method of displaying an image of the location of one or more low voltage structures in tissue, the method comprising:
receiving electrical mapping data corresponding to voltages measured from a portion of the tissue being mapped;
generating an image of the tissue being mapped using the electrical mapping data such that electrical mapping values within at least one voltage range comprising two endpoints that bound the upper and lower limits of the voltage range are distinguishable from electrical mapping values outside the at least one voltage range, wherein the two endpoints are selected to distinguish the one or more low voltage structures of the tissue being mapped from other structures of the tissue being mapped;
determining at least one endpoint of the two endpoints in response to one or more of the following voltages: an average voltage of the tissue being mapped, a maximum voltage of the tissue being mapped, and a minimum voltage of the tissue being mapped; and
displaying the generated image of the tissue being mapped.

2. The method of claim 1, wherein the electrical mapping data comprises voltage gradient mapping data.

3. The method of claim 2, wherein the voltage gradient mapping data comprises contact voltage mapping data.

4. The method of claim 1, wherein the image is a three-dimensional image.

5. The method of claim 1, wherein said determining at least one endpoint of the two endpoints is performed in response to the average voltage of the tissue being mapped.

6. The method of claim 1, wherein the tissue comprises cardiac tissue, and the one or more low voltage structures comprise one or more low voltage bridges that are indicative of a region for electrical propagation in the cardiac tissue.

7. The method of claim 6, wherein the region for electrical propagation comprises a slow pathway in the cardiac tissue or the atrial endocardial portion of the cardiac tissue.

8. The method of claim 6, wherein the one or more low voltage bridges are within the atrial septum of the cardiac tissue.

9. The method of claim 6, wherein the two endpoints are equal to or between 0.1 mV and 0.6 mV.

10. The method of claim 6, wherein the two endpoints are equal to or between 0.6 mV and 1.2 mV.

11. The method of claim 6, wherein the two endpoints are equal to or between 1 mV and 5 mV.

12. A general-purpose computer comprising a non-transitory computer-readable medium having instructions stored thereon which cause the general-purpose computer to perform a method comprising:
receiving electrical mapping data corresponding to voltages measured from a portion of the tissue being mapped;
generating an image of the tissue being mapped using the electrical mapping data such that electrical mapping values within at least one voltage range comprising two endpoints that bound the upper and lower limits of the voltage range are distinguishable from electrical mapping values outside the at least one voltage range, wherein the two endpoints are selected to distinguish the one or more low voltage structures of the tissue being mapped from other structures of the tissue being mapped;
determining at least one endpoint of the two endpoints in response to one or more of the following voltages: an average voltage of the tissue being mapped, a maximum voltage of the tissue being mapped, and a minimum voltage of the tissue being mapped; and
displaying the generated image of the tissue being mapped.

13. A method for determining the location of one or more low voltage structures in tissue, the method comprising:
receiving electrical mapping data corresponding to voltages measured from a portion of the tissue being mapped;
distinguishing electrical mapping values of the electrical mapping data within at least one voltage range comprising two endpoints that bound the upper and lower limits of the voltage range from electrical mapping values of the electrical mapping data outside the at least one voltage range, wherein the two endpoints are selected to distinguish the one or more low voltage structures of the tissue being mapped from other structures of the tissue being mapped;
determining at least one endpoint of the two endpoints in response to one or more of the following voltages: an average voltage of the tissue being mapped, a maximum voltage of the tissue being mapped, and a minimum voltage of the tissue being mapped; and
displaying the electrical mapping data with the electrical mapping values within the at least one voltage range having a different appearance than the electrical mapping values outside the at least one voltage range.

14. The method of claim 13, wherein the electrical mapping data comprises voltage gradient mapping data.

15. The method of claim 14, wherein the voltage gradient mapping data comprises contact voltage mapping data.

16. The method of claim 13, wherein displaying the electrical mapping data comprises generating an image using the electrical mapping data.

17. The method of claim 16, wherein the image is a three-dimensional image.

18. The method of claim 13, further comprising determining at least one endpoint of the two endpoints dynamically based on one or more voltages of the tissue being mapped.

19. The method of claim 18, wherein the one or more voltages comprises the average voltage of the tissue being mapped.

20. The method of claim 18, wherein determining the at least one endpoint comprises determining both endpoints of the two endpoints dynamically based on the one or more voltages of the tissue being mapped.

21. The method of claim 13, wherein the tissue comprises cardiac tissue, and the one or more low voltage structures comprise one or more low voltage bridges that are indicative of a region for electrical propagation in the cardiac tissue.

22. The method of claim 21, wherein the region for electrical propagation comprises a slow pathway in the cardiac tissue.

23. The method of claim 21, wherein the portion of the cardiac tissue comprises the atrial endocardial portion of the cardiac tissue.

24. The method of claim 21, wherein the one or more low voltage bridges are within the atrial septum of the cardiac tissue.

25. The method of claim 21, wherein the two endpoints are equal to or between 0.1 mV and 0.6 mV.

26. The method of claim 21, wherein the two endpoints are equal to or between 0.6 mV and 1.2 mV.

27. The method of claim 21, wherein the two endpoints are equal to or between 1 mV and 5 mV.

28. A method of treating tissue, the method comprising:
receiving electrical mapping data corresponding to voltages measured from a portion of the tissue being mapped;
distinguishing electrical mapping values of the electrical mapping data within at least one voltage range comprising two endpoints that bound the upper and lower limits of the voltage range from electrical mapping values of the electrical mapping data outside the at least one voltage range, wherein the two endpoints are selected to distinguish the one or more low voltage structures of the tissue being mapped from other structures of the tissue being mapped;
determining at least one endpoint of the two endpoints in response to one or more of the following voltages: an average voltage of the tissue being mapped, a maximum voltage of the tissue being mapped, and a minimum voltage of the tissue being mapped;
displaying the electrical mapping data with the electrical mapping values within the at least one voltage range having a different appearance than the electrical mapping values outside the at least one voltage range; and
locating at least a portion of the tissue being mapped corresponding to one or more of the low voltage structures.

29. The method of claim 28, wherein the tissue is cardiac tissue and the located portion of tissue comprises the one or more of the low voltage structures comprises a slow pathway in the cardiac tissue.

30. The method of claim 29, wherein the method further comprises ablating at least a portion of the slow pathway.

31. The method of claim 28, wherein the tissue comprises skeletal muscle tissue, smooth muscle tissue, peristaltic tissue, retinal tissue, or neurological tissue in which the located portion of the tissue comprises seizure and/or trauma foci.

32. A general-purpose computer comprising a non-transitory computer-readable medium having instructions stored thereon which cause the general-purpose computer to perform a method comprising:
- receiving electrical mapping data corresponding to voltages measured from a portion of the tissue being mapped;
- distinguishing electrical mapping values of the electrical mapping data within a voltage range comprising two endpoints that bound the upper and lower limits of the voltage range from electrical mapping values of the electrical mapping data outside the voltage range, wherein the two endpoints are selected to distinguish the one or more low voltage structures of the tissue from other structures of the tissue being mapped;
- determining at least one endpoint of the two endpoints in response to one or more of the following voltages: an average voltage of the tissue being mapped, a maximum voltage of the tissue being mapped, and a minimum voltage of the tissue being mapped;
- displaying the electrical mapping data with the electrical mapping values within the voltage range having a different appearance than the electrical mapping values outside the voltage range.

\* \* \* \* \*